(12) United States Patent
Solar et al.

(10) Patent No.: US 7,867,242 B2
(45) Date of Patent: Jan. 11, 2011

(54) INSTRUMENT FOR GUIDING STAGE APPARATUS AND METHOD FOR USING SAME

(75) Inventors: Matthew S. Solar, Indialantic, FL (US); Thomas I. Miller, Palm Bay, FL (US); James G. Skakoon, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/349,657

(22) Filed: Jan. 7, 2009

(65) Prior Publication Data
US 2009/0118743 A1      May 7, 2009

Related U.S. Application Data

(62) Division of application No. 11/005,607, filed on Dec. 4, 2004, now Pat. No. 7,497,863.

(51) Int. Cl.
*A61B 19/00* (2006.01)
(52) U.S. Cl. .................................................... 606/130
(58) Field of Classification Search .................. 606/130
See application file for complete search history.

(56) References Cited

U.S. PATENT DOCUMENTS

| | | |
|---|---|---|
| 431,187 A | 7/1890 | Foster |
| 438,801 A | 10/1890 | Delehanty |
| 873,009 A | 12/1907 | Baxter |
| 1,129,333 A | 2/1915 | Clarke |
| 1,664,210 A | 3/1928 | Hall |
| 2,119,649 A | 6/1938 | Roosen |
| 2,135,160 A | 11/1938 | Beekhuis |
| 2,497,820 A | 2/1950 | Kielland |

(Continued)

FOREIGN PATENT DOCUMENTS

DE          3108766          9/1982

(Continued)

OTHER PUBLICATIONS

Vestavia Scientific, Product Information Hydraulic Microdrive, May 1, 2000, pp. 1-2.*

(Continued)

*Primary Examiner*—Gary Jackson
*Assistant Examiner*—Gregory Anderson
(74) *Attorney, Agent, or Firm*—Harness, Dickey & Pierce, PLC

(57) ABSTRACT

This documents describes among other things a normalizing stage apparatus, tools and methods. One example includes a base that defines a trajectory. A first stage is moveably coupled to the base and the first stage moves along the trajectory. A second stage is moveably coupled to the first stage and moves an instrument coupled thereto with respect to the base and the first stage. Before movement of the instrument, the first and second stages are in first positions desired (e.g. predetermined) distances from a target area in the body. Another example includes the first stage and a guide tube stop coupled with the first stage. A guide tube is coupled with the guide tube stop and extends through a guide tube stop lumen. The guide tubes outer perimeter is dimensioned and configured to snugly couple with the surface defining the guide tube stop lumen.

19 Claims, 35 Drawing Sheets

U.S. PATENT DOCUMENTS

| | | |
|---|---|---|
| 2,686,890 A | 8/1954 | Davis |
| 3,010,347 A | 11/1961 | Kron |
| 3,016,899 A | 1/1962 | Stenvall |
| 3,017,887 A | 1/1962 | Heyer |
| 3,055,370 A | 9/1962 | McKinney et al. |
| 3,055,371 A | 9/1962 | Kulick et al. |
| 3,115,140 A | 12/1963 | Volkman |
| 3,135,263 A | 6/1964 | Connelley, Jr. |
| 3,223,087 A | 12/1965 | Vladyka et al. |
| 3,262,452 A | 7/1966 | Hardy et al. |
| 3,273,559 A | 9/1966 | Evans |
| 3,282,152 A | 11/1966 | Myer |
| 3,402,710 A | 9/1968 | Paleschuck |
| 3,444,861 A | 5/1969 | Schulte |
| 3,457,922 A | 7/1969 | Ray |
| 3,460,537 A | 8/1969 | Zeis |
| 3,508,552 A | 4/1970 | Hainault |
| 3,672,352 A | 6/1972 | Summers |
| 3,760,811 A | 9/1973 | Andrew et al. |
| 3,817,249 A | 6/1974 | Nicholson |
| 3,893,449 A | 7/1975 | Lee et al. |
| 3,981,079 A | 9/1976 | Lenczycki |
| 4,013,080 A | 3/1977 | Froning |
| 4,026,276 A | 5/1977 | Chubbuck |
| 4,040,427 A | 8/1977 | Winnie |
| 4,131,257 A | 12/1978 | Sterling |
| 4,230,117 A | 10/1980 | Anichkov et al. |
| 4,265,252 A | 5/1981 | Chubbuck et al. |
| 4,312,337 A | 1/1982 | Donohue |
| 4,318,401 A | 3/1982 | Zimmerman |
| 4,328,813 A | 5/1982 | Ray |
| 4,341,220 A | 7/1982 | Perry |
| 4,345,606 A | 8/1982 | Littleford |
| 4,350,159 A | 9/1982 | Gouda |
| 4,355,645 A | 10/1982 | Mitani et al. |
| 4,386,602 A | 6/1983 | Sheldon et al. |
| 4,418,894 A | 12/1983 | Mailliet et al. |
| 4,448,195 A | 5/1984 | LeVeen et al. |
| 4,463,758 A | 8/1984 | Patil et al. |
| 4,475,550 A | 10/1984 | Bremer et al. |
| 4,483,344 A | 11/1984 | Atkov et al. |
| 4,571,750 A | 2/1986 | Barry |
| 4,572,198 A | 2/1986 | Codrington |
| 4,579,120 A | 4/1986 | MacGregor |
| 4,592,352 A | 6/1986 | Patil |
| 4,598,708 A | 7/1986 | Beranek |
| 4,608,977 A | 9/1986 | Brown |
| 4,617,925 A | 10/1986 | Laitinen et al. |
| 4,618,978 A | 10/1986 | Cosman |
| 4,629,451 A | 12/1986 | Winters et al. |
| 4,638,798 A | 1/1987 | Shelden et al. |
| 4,660,563 A | 4/1987 | Lees |
| 4,665,928 A | 5/1987 | Linial et al. |
| 4,699,616 A | 10/1987 | Nowak et al. |
| 4,705,436 A | 11/1987 | Robertson et al. |
| 4,706,665 A | 11/1987 | Gouda |
| 4,733,661 A | 3/1988 | Palestrant |
| 4,755,642 A | 7/1988 | Parks |
| 4,791,934 A | 12/1988 | Brunnett |
| 4,793,355 A | 12/1988 | Crum et al. |
| 4,798,208 A | 1/1989 | Faasse, Jr. |
| 4,805,615 A | 2/1989 | Carol |
| 4,805,634 A | 2/1989 | Ullrich et al. |
| 4,807,620 A | 2/1989 | Strul et al. |
| 4,809,694 A | 3/1989 | Ferrara |
| 4,824,436 A | 4/1989 | Wolinsky |
| 4,826,487 A | 5/1989 | Winter |
| 4,869,247 A | 9/1989 | Howard, III et al. |
| 4,883,053 A | 11/1989 | Simon |
| 4,896,673 A | 1/1990 | Rose et al. |
| 4,902,129 A | 2/1990 | Siegmund et al. |
| 4,922,924 A | 5/1990 | Gambale et al. |
| 4,955,891 A | 9/1990 | Carol |
| 4,957,481 A | 9/1990 | Gatenby |
| 4,986,280 A | 1/1991 | Marcus et al. |
| 4,986,281 A | 1/1991 | Preves et al. |
| 4,989,608 A | 2/1991 | Ratner |
| 4,991,579 A | 2/1991 | Allen |
| 4,998,938 A | 3/1991 | Ghajar et al. |
| 5,006,122 A | 4/1991 | Wyatt et al. |
| 5,024,236 A | 6/1991 | Shapiro |
| 5,027,818 A | 7/1991 | Bova et al. |
| 5,030,223 A | 7/1991 | Anderson et al. |
| 5,050,608 A | 9/1991 | Watanabe et al. |
| 5,052,329 A | 10/1991 | Bennett |
| 5,054,497 A | 10/1991 | Kapp et al. |
| 5,057,084 A | 10/1991 | Ensminger et al. |
| 5,057,106 A | 10/1991 | Kasevich et al. |
| 5,065,761 A | 11/1991 | Pell |
| 5,078,140 A | 1/1992 | Kwoh |
| 5,078,142 A | 1/1992 | Siczek et al. |
| 5,080,662 A | 1/1992 | Paul |
| 5,087,256 A | 2/1992 | Taylor et al. |
| 5,099,846 A | 3/1992 | Hardy |
| 5,102,402 A | 4/1992 | Dror et al. |
| 5,116,344 A | 5/1992 | Sundqvist et al. |
| 5,116,345 A | 5/1992 | Jewell et al. |
| 5,120,322 A | 6/1992 | Davis et al. |
| 5,125,888 A | 6/1992 | Howard et al. |
| 5,142,930 A | 9/1992 | Allen et al. |
| 5,143,086 A | 9/1992 | Duret et al. |
| 5,154,179 A | 10/1992 | Ratner |
| 5,154,723 A | 10/1992 | Kubota et al. |
| 5,163,430 A | 11/1992 | Carol |
| 5,166,875 A | 11/1992 | Machida et al. |
| 5,171,217 A | 12/1992 | March et al. |
| 5,174,297 A | 12/1992 | Daikuzono et al. |
| 5,186,174 A | 2/1993 | Schlondorff et al. |
| 5,201,742 A | 4/1993 | Hasson |
| 5,207,223 A | 5/1993 | Adler |
| 5,207,688 A | 5/1993 | Carol |
| 5,211,165 A | 5/1993 | Dumoulin et al. |
| 5,221,264 A | 6/1993 | Wilk et al. |
| 5,222,499 A | 6/1993 | Allen et al. |
| 5,230,338 A | 7/1993 | Allen et al. |
| 5,230,623 A | 7/1993 | Guthrie et al. |
| 5,242,415 A | 9/1993 | Kantrowitz et al. |
| 5,246,448 A | 9/1993 | Chang |
| 5,257,998 A | 11/1993 | Ota et al. |
| 5,263,939 A | 11/1993 | Wortrich |
| 5,263,956 A | 11/1993 | Nobles |
| 5,267,970 A | 12/1993 | Chin et al. |
| 5,269,305 A | 12/1993 | Corol |
| 5,279,309 A | 1/1994 | Taylor et al. |
| 5,279,575 A | 1/1994 | Sugarbaker |
| 5,280,427 A | 1/1994 | Magnusson et al. |
| 5,290,266 A | 3/1994 | Rohling et al. |
| 5,291,890 A | 3/1994 | Cline et al. |
| 5,300,080 A | 4/1994 | Clayman et al. |
| 5,305,203 A | 4/1994 | Raab et al. |
| 5,306,272 A | 4/1994 | Cohen et al. |
| 5,309,913 A | 5/1994 | Kormos et al. |
| 5,330,485 A | 7/1994 | Clayman et al. |
| 5,354,283 A | 10/1994 | Bark et al. |
| 5,361,763 A | 11/1994 | Kao et al. |
| 5,366,446 A | 11/1994 | Tal et al. |
| 5,375,588 A | 12/1994 | Yoon |
| 5,375,596 A | 12/1994 | Twiss et al. |
| 5,380,302 A | 1/1995 | Orth |
| 5,383,454 A | 1/1995 | Bucholz |
| 5,387,220 A | 2/1995 | Pisharodi |
| 5,394,457 A | 2/1995 | Leibinger et al. |
| 5,405,330 A | 4/1995 | Zunitch et al. |
| 5,423,832 A | 6/1995 | Gildenberg |

| | | | | | | |
|---|---|---|---|---|---|---|
| 5,423,848 A | 6/1995 | Washizuka et al. | 6,135,946 A | 10/2000 | Konen et al. | |
| 5,445,166 A | 8/1995 | Taylor | 6,179,826 B1 | 1/2001 | Aebischer et al. | |
| 5,452,720 A | 9/1995 | Smith et al. | 6,195,577 B1 | 2/2001 | Truwit et al. | |
| 5,464,446 A | 11/1995 | Dreessen et al. | 6,206,890 B1 | 3/2001 | Truwit | |
| 5,470,307 A | 11/1995 | Lindall | 6,210,417 B1 | 4/2001 | Baudino et al. | |
| 5,474,564 A | 12/1995 | Clayman et al. | 6,231,526 B1 | 5/2001 | Taylor et al. | |
| 5,483,961 A | 1/1996 | Kelly et al. | 6,236,875 B1 | 5/2001 | Bucholz et al. | |
| 5,494,034 A | 2/1996 | Schlondorff et al. | 6,238,402 B1 | 5/2001 | Sullivan, III et al. | |
| 5,494,655 A | 2/1996 | Rocklage et al. | 6,254,532 B1 | 7/2001 | Paolitto et al. | |
| 5,515,160 A | 5/1996 | Schulz et al. | 6,257,407 B1 | 7/2001 | Truwit et al. | |
| 5,517,990 A | 5/1996 | Kalfas et al. | 6,261,300 B1 | 7/2001 | Carol et al. | |
| 5,528,652 A | 6/1996 | Smith et al. | 6,267,769 B1 | 7/2001 | Truwit | |
| 5,541,377 A | 7/1996 | Stuhlmacher | 6,267,770 B1 | 7/2001 | Truwit | |
| 5,572,905 A | 11/1996 | Cook, Jr. | 6,273,896 B1 | 8/2001 | Franck et al. | |
| 5,572,999 A | 11/1996 | Funda et al. | 6,282,437 B1 | 8/2001 | Franck et al. | |
| 5,575,798 A | 11/1996 | Koutrouvelis | 6,290,644 B1 | 9/2001 | Green, II et al. | |
| 5,618,288 A | 4/1997 | Calvo et al. | 6,298,262 B1 | 10/2001 | Franck et al. | |
| 5,622,170 A | 4/1997 | Schulz | 6,315,770 B1 | 11/2001 | de la Torre et al. | |
| 5,638,819 A | 6/1997 | Manwaring et al. | 6,321,104 B1 | 11/2001 | Gielen et al. | |
| 5,639,276 A | 6/1997 | Weinstock et al. | 6,327,491 B1 | 12/2001 | Franklin et al. | |
| 5,643,286 A | 7/1997 | Warner et al. | 6,356,792 B1 | 3/2002 | Errico et al. | |
| 5,647,361 A | 7/1997 | Damadian | 6,368,329 B1 | 4/2002 | Truwit | |
| 5,649,936 A | 7/1997 | Real | 6,400,992 B1 | 6/2002 | Borgersen et al. | |
| 5,658,272 A | 8/1997 | Hasson | 6,457,963 B1 | 10/2002 | Tawara et al. | |
| 5,662,600 A | 9/1997 | Watson et al. | 6,482,182 B1 | 11/2002 | Carroll et al. | |
| 5,667,514 A | 9/1997 | Heller | 6,488,620 B1 | 12/2002 | Segermark et al. | |
| 5,695,501 A | 12/1997 | Carol et al. | 6,491,699 B1 | 12/2002 | Henderson et al. | |
| 5,713,858 A | 2/1998 | Heruth et al. | 6,529,765 B1 | 3/2003 | Franck et al. | |
| 5,755,697 A | 5/1998 | Jones et al. | 6,537,232 B1 | 3/2003 | Kucharczyk et al. | |
| 5,776,064 A | 7/1998 | Kalfas et al. | 6,546,277 B1 | 4/2003 | Frànck et al. | |
| 5,776,143 A | 7/1998 | Adams et al. | 6,546,279 B1 | 4/2003 | Bova et al. | |
| 5,776,144 A | 7/1998 | Leysieffer et al. | 6,547,795 B2 | 4/2003 | Schneiderman | |
| 5,788,713 A | 8/1998 | Dubach et al. | 6,556,857 B1 | 4/2003 | Estes et al. | |
| 5,807,033 A | 9/1998 | Benway | 6,609,020 B2 | 8/2003 | Gill et al. | |
| 5,809,694 A | 9/1998 | Postans et al. | 6,610,100 B2 | 8/2003 | Phelps et al. | |
| 5,810,712 A | 9/1998 | Dunn | 6,632,184 B1 | 10/2003 | Truwit | |
| 5,817,106 A | 10/1998 | Real | 6,655,014 B1 | 12/2003 | Babini | |
| 5,823,975 A | 10/1998 | Stark et al. | 6,662,035 B2 | 12/2003 | Sochor | |
| 5,833,627 A | 11/1998 | Shmulewitz et al. | 6,676,669 B2 | 1/2004 | Charles et al. | |
| 5,843,150 A | 12/1998 | Dreessen et al. | 6,706,050 B1 | 3/2004 | Giannadakis | |
| 5,851,183 A | 12/1998 | Bucholz | 6,726,678 B1 | 4/2004 | Nelson et al. | |
| 5,865,817 A | 2/1999 | Moenning et al. | 6,746,471 B2 | 6/2004 | Mortier et al. | |
| 5,865,842 A | 2/1999 | Knuth et al. | 6,752,812 B1 | 6/2004 | Truwit | |
| 5,871,445 A | 2/1999 | Bucholz | 6,765,122 B1 | 7/2004 | Stout | |
| 5,871,487 A | 2/1999 | Warner et al. | 6,773,443 B2 | 8/2004 | Truwit et al. | |
| 5,873,822 A | 2/1999 | Ferre et al. | 6,782,288 B2 | 8/2004 | Truwit et al. | |
| 5,891,034 A | 4/1999 | Bucholz | 6,802,323 B1 | 10/2004 | Truwit et al. | |
| 5,891,157 A | 4/1999 | Day et al. | 6,902,569 B2 | 6/2005 | Parmer et al. | |
| 5,927,277 A | 7/1999 | Baudino et al. | 6,913,478 B2 | 7/2005 | Lamirey et al. | |
| 5,950,629 A | 9/1999 | Taylor et al. | 6,944,895 B2 | 9/2005 | Truwit | |
| 5,954,687 A | 9/1999 | Baudino | 6,960,216 B2 | 11/2005 | Kolb et al. | |
| 5,957,933 A | 9/1999 | Yanof et al. | 7,204,840 B2 | 4/2007 | Skakoon et al. | |
| 5,957,934 A | 9/1999 | Rapoport et al. | 7,366,561 B2 * | 4/2008 | Mills et al. | 600/417 |
| 5,964,705 A | 10/1999 | Truwit et al. | 7,479,146 B2 | 1/2009 | Malinowski | |
| 5,980,535 A | 11/1999 | Barnett et al. | 2001/0014771 A1 | 8/2001 | Truwit et al. | |
| 5,984,930 A | 11/1999 | Maciunas et al. | 2001/0027271 A1 | 10/2001 | Franck et al. | |
| 5,993,463 A | 11/1999 | Truwit | 2001/0037524 A1 | 11/2001 | Truwit | |
| 5,997,471 A | 12/1999 | Gumb et al. | 2002/0010479 A1 | 1/2002 | Skakoon et al. | |
| 6,006,126 A | 12/1999 | Cosman | 2002/0019641 A1 | 2/2002 | Truwit | |
| 6,018,094 A | 1/2000 | Fox | 2002/0022847 A1 | 2/2002 | Ray et al. | |
| 6,021,343 A | 2/2000 | Foley et al. | 2002/0052610 A1 | 5/2002 | Skakoon et al. | |
| 6,024,729 A | 2/2000 | Dehdashtian et al. | 2002/0077646 A1 | 6/2002 | Truwit et al. | |
| 6,030,223 A | 2/2000 | Sugimori | 2002/0156372 A1 | 10/2002 | Skakoon et al. | |
| 6,039,725 A | 3/2000 | Moenning et al. | 2003/0079287 A1 | 5/2003 | Truwit | |
| 6,042,540 A | 3/2000 | Johnston et al. | 2003/0187351 A1 | 10/2003 | Franck et al. | |
| 6,044,304 A | 3/2000 | Baudino | 2003/0208122 A1 | 11/2003 | Melkent et al. | |
| 6,058,323 A | 5/2000 | Lemelson | 2004/0026161 A1 | 2/2004 | Takatsuka et al. | |
| 6,071,288 A | 6/2000 | Carol et al. | 2004/0059260 A1 | 3/2004 | Truwit | |
| 6,076,008 A | 6/2000 | Bucholz | 2004/0176750 A1 | 9/2004 | Nelson et al. | |
| 6,079,681 A | 6/2000 | Stern et al. | 2004/0243147 A1 | 12/2004 | Lipow | |
| 6,110,182 A | 8/2000 | Mowlai-Ashtiani | 2004/0255991 A1 | 12/2004 | Truwit et al. | |
| 6,117,143 A | 9/2000 | Hynes et al. | 2004/0260323 A1 | 12/2004 | Truwit et al. | |
| 6,120,465 A | 9/2000 | Guthrie et al. | 2004/0267284 A1 | 12/2004 | Parmer et al. | |

| | | |
|---|---|---|
| 2006/0122627 A1 | 6/2006 | Miller et al. |
| 2006/0192319 A1 | 8/2006 | Solar |
| 2006/0195119 A1 | 8/2006 | Mazzocchi et al. |
| 2007/0250078 A1 | 10/2007 | Stuart |
| 2007/0299427 A1 | 12/2007 | Yeung et al. |
| 2008/0004632 A1 | 1/2008 | Sutherland et al. |

FOREIGN PATENT DOCUMENTS

| | | |
|---|---|---|
| DE | 3937052 | 5/1990 |
| DE | 19726141 | 1/1999 |
| DE | 29612100 | 8/1999 |
| DE | 19808220 | 9/1999 |
| DE | 19820808 | 9/1999 |
| DE | 19826078 | 11/1999 |
| EP | 0386936 | 5/1990 |
| EP | 0427358 | 5/1991 |
| EP | 0724865 | 5/1991 |
| EP | 0609085 | 8/1994 |
| EP | 0832611 | 4/1998 |
| EP | 0904741 | 3/1999 |
| GB | 2237993 | 5/1991 |
| GB | 2329473 | 4/1998 |
| GB | 2346573 | 8/2000 |
| WO | WO-8809151 | 12/1988 |
| WO | WO-9721380 | 12/1988 |
| WO | WO-9522297 | 8/1995 |
| WO | WO-9610368 | 4/1996 |
| WO | WO-9633766 | 10/1996 |
| WO | WO-9703609 | 2/1997 |
| WO | WO-9742870 | 11/1997 |
| WO | WO-9817191 | 4/1998 |
| WO | WO-9825535 | 6/1998 |
| WO | WO-9851229 | 11/1998 |
| WO | WO-0001316 | 1/2000 |
| WO | WO-0018306 | 1/2000 |
| WO | WO-0124709 | 4/2001 |
| WO | WO-0149197 | 7/2001 |
| WO | WO-0176498 | 7/2001 |
| WO | WO-2004026161 A2 | 4/2004 |

OTHER PUBLICATIONS

Supplementary European Search Report mailed Oct. 26, 2009 for EP05852969 filed Dec. 6, 2005 claiming benefit of U.S. Appl. No. 11/005,907, filed Dec. 5, 2004.
"Cross-Hairs Kit", Elekta Instruction for Use Brochure, pp. 1-5.
"CRWTM—Tyco Healthcare Radionics", *Tyco Products Brochure*, pp. 1-7.
"Fathom Remote Introducer", *Image-Guided Neurologics, Inc.*, CNS Hynes Convention Center, (Oct. 30-Nov. 4, 1999), 2 pgs.
"Inomed Competence in Neurophysiologic Monitoring", http://www.inomed.com/english/index.htm, (observed Mar. 23, 2004), 2 pgs.
"Leksell Sterotatic System", *Elekta Products Brochure*, pp. 1-6.
"MicroTargeting® Precision Guidance Using Microelectrode Recording", (Aug. 15, 2003), 5 pgs.
"Possible Existence of Common Internalization Mechanisms among Arginine-rich Peptides", Suzuki, T. et al., Journal of Biological Chemistry, vol. 277, No. 4 (2002) pp. 2437-2443.
Allison, S., et al., "Microchannel Plate Intensifier Response in Traverse Magnetic Field", Electronic Letters, 26, (Jun. 7, 1990), 770-771.
Drake, J. M., et al., "ISG Viewing Wand System", *Neurosurgery*, 34 (6), (Jun. 1994), pp. 1094-1097.
Dyer, P. V., et al., "The ISG Viewing Wand: an application to atlanto-axial cervical surgery using the Le Fort I maxillary osteotomy", *British Journal of Oral and Maxillofacial Surgery*, 33, (1995), pp. 370-374.
Franck, Joel, et al., "microTargeting® Platform incorporating StarFix™ guidance", *microTargeting*, 3 pgs.
Franck, Joel, et al., "microTargeting® Platform System incorporating StarFix™ guidance", *microTargeting*, (2001-2002), p. 44.
Gehring, W. J., "Homeodomain Proteins", Annu. Rev. Biochem., vol. 63 (1997) pp. 487-526.

Gillies, G., et al., "Magnetic Manipulation Instrumentation for Medical Physics Research", Review of Scientific Instruments, 65 (3), Review Article, (Mar. 1994), 533-562.
Grady, M. S., "Magnetic Stereotaxis System for Neurosurgical Procedures", *Proceedings of the 37th International Instrumentation Symposium*, (May 5-9, 1991), pp. 665-675.
Grady, M. S., et al., "Initial Experimental Results of a New Stereotaxic Hyperthermia System", *American College of Surgeons, Surgical Forum*, vol. XXXIX, *Neurological Surgery*, (1988), pp. 507-509.
Grady, M. S., et al., "Magnetic Stereotaxis: A Technique to Deliver Stereotactic Hyperthermia", *Neurosurgery*, 27 (6), (1990), pp. 1010-1016.
Grady, M. S., et al., "Preliminary experimental investigation of in vivo magnetic manipulation: Results and potential application in hyperthermia", *Medical Physics*, 16 (2), (Mar./Apr. 1989), pp. 263-272.
Grady, M., et al., "Nonlinear Magnetic Stereotaxis: Three-Dimensional, in vivo Remote Magnetic Manipulation of a Small Object in Canine Brain", *Medical Physics*, 17 (3) (May/Jun. 1990), pp. 405-415.
Hata, N., et al., "Needle Insertion Manipulator for CT- and MR-Guided Stereotactic Neurosurgery", *Interventional MR: Techniques and Clinical Experience*, St. Louis : London : Mosby ; Martin Dunitz, F. Jolesz and I. Young, eds., (1998), pp. 99-106.
Hirschberg, H., et al., "Image-guided neurosurgery—MR compatible stereotactic equipment", http://www.medinnova.no/English/P51466ster.html, (Mar. 29, 2001), 1 pg. (viewed website on Mar. 29, 2001).
Hirschberg, Henry, et al., "Image-guided neurosurgery", stereotactic equipment for MR imaging, http://www.medinnova.no/English/P51466ster.html, (Observed Mar. 8, 2002), 1 page.
Howard III, M. A., et al., "Magnetic Neurosurgery: Image-Guided Remote-Controlled Movement of Neurosurgical Implants", *Clinical Neurosurgery*, (1995), pp. 382-391.
Howard III, M. A., et al., "Review of Magnetic Neurosurgery Research", *Journal of Image Guided Surgery*, 1 (6), (1995), pp. 295-299.
Howard, M. A., et al., "Magnetic Movement of a Brain Thermoceptor", *Neurosurgery*, 24 (3), (Mar. 1989), pp. 444-448.
Howard, M. A., et al., "Magnetic Neurosurgery", Proceedings of the Meeting of the American Society for Stereotactic and Functional Neurosurgery, (Mar. 8-11, 1995), pp. 102-107.
International Search Report and Written Opinion for PCT/US05/43651 mailed May 8, 2008.
Lawson, M. A., et al., "Near Real-Time Bi-planar Fluoroscopic Tracking System for the Video Tumor Fighter", *SPIE, vol. 1445 Image Processing*, (1991), pp. 265-275.
Leggett, W.B., et al., "Surgical Technology—The Viewing Wand: A New System for Three-Dimensional Computed Tomography-Correlated Intraoperative Localization", *Current Surgery*, (Dec. 1991), pp. 674-678.
Malison, R. T., et al., "Computer-Assisted Coregistration of Multislice SPECT and MR Brain Images by Fixed External Fiducials", Journal of Computer Assisted Tomography, 17 (6) (1993) pp. 952-960.
Mannervik, M., "Target genes of homeodomain proteins", BioEssays vol. 21.4 (Apr. 1999) pp. 267-270.
McNeil, R. G., et al., "Characteristics of an Improved Magnetic-Implant Guidance System", *IEEE Transactions on Biomedical Engineering*, 42 (8), (Aug. 1995), pp. 802-808.
McNeil, R. G., et al., "Functional Design Features and Initial Performance Characteristics of a Magnetic-Implant Guidance System for Stereotactic Neurosurgery", *IEEE Transactions on Biomedical Engineering*, 42 (8), pp. 793-801.
Meeker, D., et al., "Optimal Realization of Arbitrary Forces in a Magnetic Stereotaxis System," IEEE Transactions on Magnetics, 32 (2), (Mar. 1996), 320-328.
Molloy, J. A., et al., "Experimental Determination of the Force Required for Insertion of a Thermoseed Into Deep Brain Tissues", *Annals of Biomedical Engineering*, 18 (3), (1990), pp. 299-313.

Molloy, J. A., et al., "Thermodynamics of movable inductively heated seeds for the treatment of brain tumors", *Medical Physics*, 18 (4), (Jul./Aug. 1991), pp. 794-803.

Oliver, L., "Cup-And-Ball Chemopallidectomy Apparatus", (1958), p. 410.

Patikoglou, G. et al., "Eukaryotic Transcription Factor-DNA Complexes", Annual Review of Biophysics and Biomolecular Structure vol. 26 (1997) pp. 289-325.

Quate, E., et al., "Goniometric Motion Controller for the Superconducting Coil in a Magnetic Stereotaxis System", IEEE Transactions on Biomedical Engineering, 38 (9), (Sep. 1991), 899-905.

Ramos, P. A., et al., "Electro-optic imaging chain for a biplanar fluoroscope for neurosurgery: magnetic field sensitivity and contrast measurements", *Optical Engineering*, 32 (7), (Jul. 1993), pp. 1644-1656.

Ramos, P. A., et al., "Low-dose, magnetic field-immune, bi-planar fluoroscopy for neurosurgery", *SPIE Medical Imaging V: Image Physics*, vol. 1443, (1991), pp. 160-170.

Ramos, P. A., et al., "Microchannel Plate Image Intensifier Electron Dynamics in Magnetic Field", *Electronics Letters*, 27 (18), (Aug. 29, 1991), pp. 1636-1638.

Ritter, R. C., et al., "Magnetic Stereotaxis: An Application of Magnetic Control Technology to the Needs of Clinical Medicine", *Proc. of the MAG'95 Industrial Conf. and Exhibition, Technomic Pub. Co.*, Lancaster, PA., Allaire, P., ed., (1995), pp. 186-193.

Ritter, R. C., et al., "Magnetic Stereotaxis: Computer-Assisted Image-Guided Remote Movement of Implants in the Brain", *Computer-Integrated Surgery: Technology and Clinical Applications*, MIT Press, (1996), pp. 363-369.

Sandeman, D. S., et al., "Advances in image-directed neurosurgery: Preliminary experience with the ISG Viewing Wand compared with the Leksell G frame", *British Journal of Neurosurgery*, 8, (1994), pp. 529-544.

Stein, S. et al., "Checklist: Vertebrate homeobox genes", Mechanisms of Development, vol. 55, No. 1 (Mar. 1996) pp. 91-108.

Szikora, I., et al., "Endovascular Treatment of Experimental Aneurysms with Liquid Polymers: The Protective Potential of Stents", *Neurosurgery*, 38, (Feb. 1996), pp. 339-347.

Vollmer, J. et al., "Homeobox Genes in the Developing Mouse Brain", Journal of Neurochemistry, vol. 71, No. 1 (Jul. 1998) pp. 1-19.

Wolberger, C., "Homeodomain Interactions", Current Opinion in Structural Biology vol. 6, No. 1 (Feb. 1996) pp. 62-68.

Yeh, H.-S., et al., "Implantation of intracerebral depth electrodes for monitoring seizures usign the Pelorus stereotactic system guided by magnetic resonance imaging", *J. Neurosurg.*, 78, (1993), pp. 138-141.

Zinreich, S. J., et al., "Frameless Stereotaxic Integration of CT Imaging Data: Accuracy and Initial Applications", *Radiology*, 188 (3), (1993), pp. 735-742.

Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.

European Office Action mailed Jan. 22, 2010 for European Application No. 05 852 969.4.

* cited by examiner

INSTRUMENT FOR GUIDING STAGE APPARATUS AND METHOD FOR USING SAME

CROSS-REFERENCE TO RELATED APPLICATIONS

This application is a divisional of U.S. patent application Ser. No. 11/005,607 filed on Dec. 4, 2004. The entire disclosure of the above application is incorporated herein by reference.

This application also relates to Ser. No. 11/005,605 filed on Dec. 4, 2004, entitled "MULTI-LUMEN INSTRUMENT GUIDE," the disclosure of which is also incorporated herein by reference in its entirety.

FIELD

The present disclosure relates generally to a stage from which instruments are positioned and in particular to a stage that provides a known distance from the stage to a target.

BACKGROUND

This section provides background information related to the present disclosure which is not necessarily prior art.

Neurosurgery sometimes involves inserting an electrode such as a recording or stimulating electrode (for recording brain signals or providing stimulating pulses), or other instrument (for example, a catheter for fluid aspiration or drug infusion) through a burr hole or other entry portal into a subject's brain towards a target region of the brain. The present inventors have recognized an unmet need for normalizing stage devices, tools, and methods that provide a known distance between a stage and a target, such as to reduce or avoid physician and technician calculations and equipment adjustments.

DRAWINGS

The drawings described herein are for illustrative purposes only of selected embodiments and not all possible implementations, and are not intended to limit the scope of the present disclosure.

FIG. 10 B is a section view illustrating another example of the fluid inlet and syringe, as well as another example of the master cylinder and master piston.

FIG. 11 A is an exploded view of a fixture assembly illustrating a skull surface, instrument immobilizer, trajectory guide, and an alignment ring.

Figure 11A:
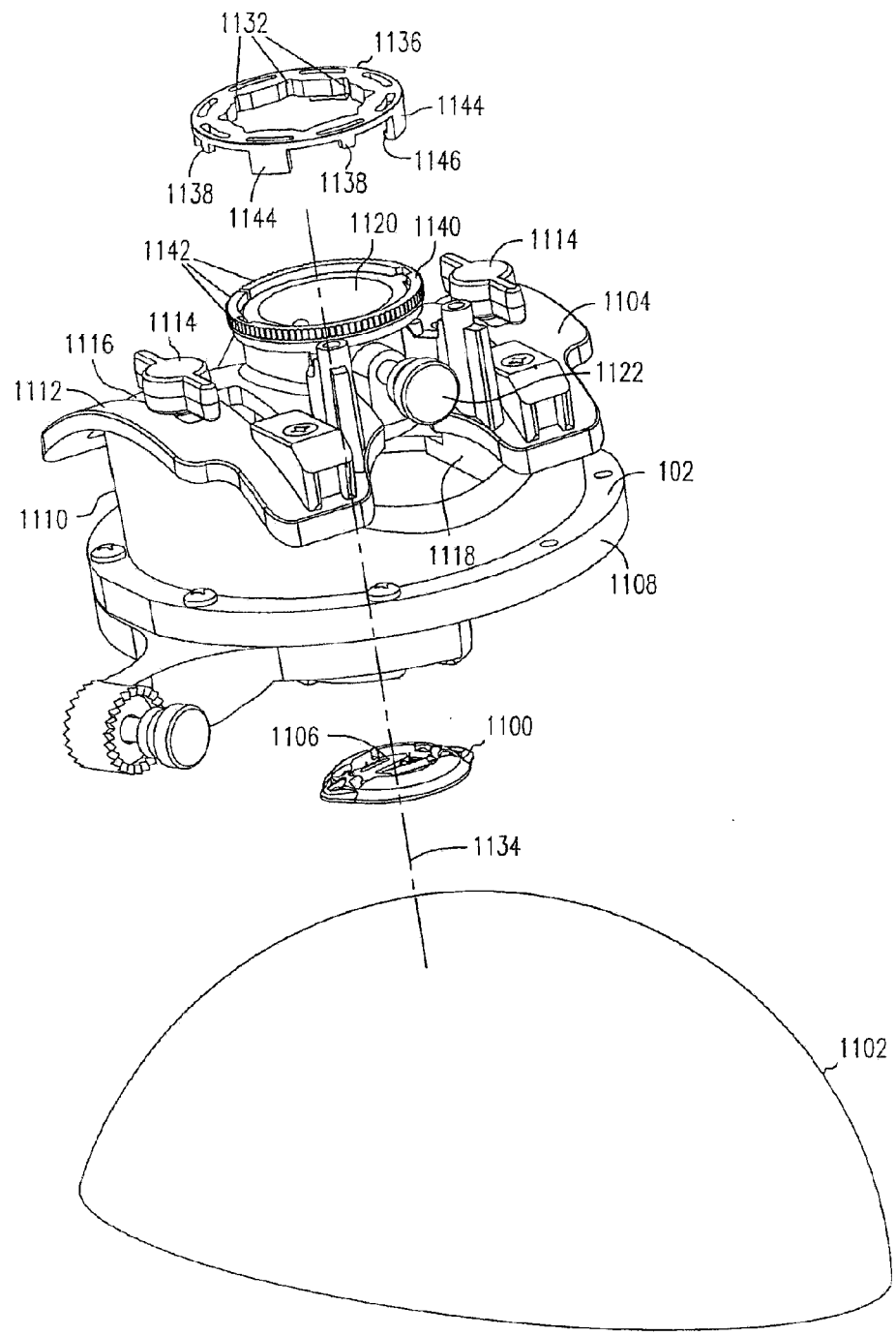
Figure 11B:
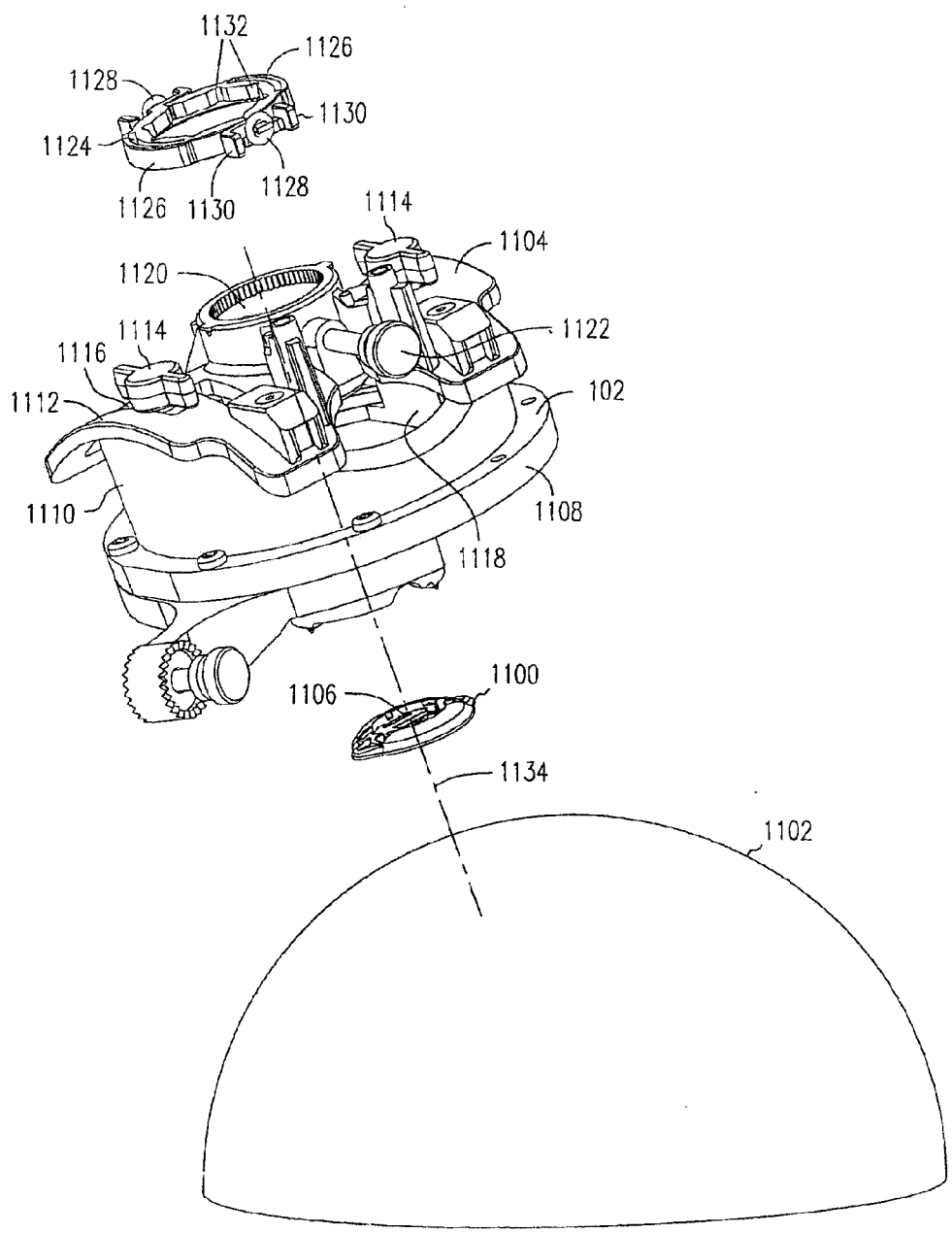

FIG. 11B is an exploded view of a fixture assembly illustrating a skull surface, instrument immobilizer, trajectory guide, and another example of an alignment ring.

Figure 12:
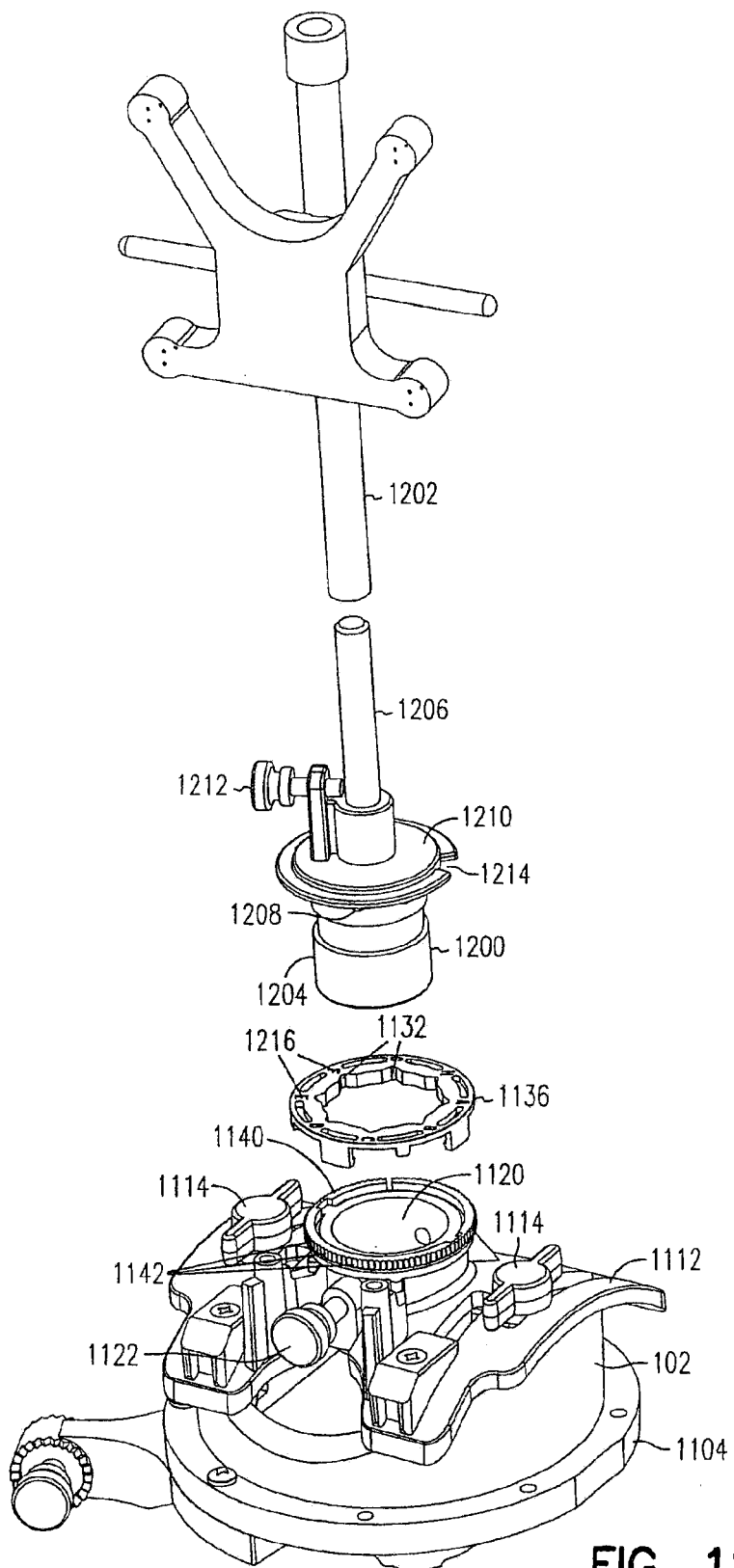

FIG. 12 is an exploded view of a fixture assembly including the trajectory guide, alignment ring, centered alignment guide, and orienting fixture.

Figure 13:
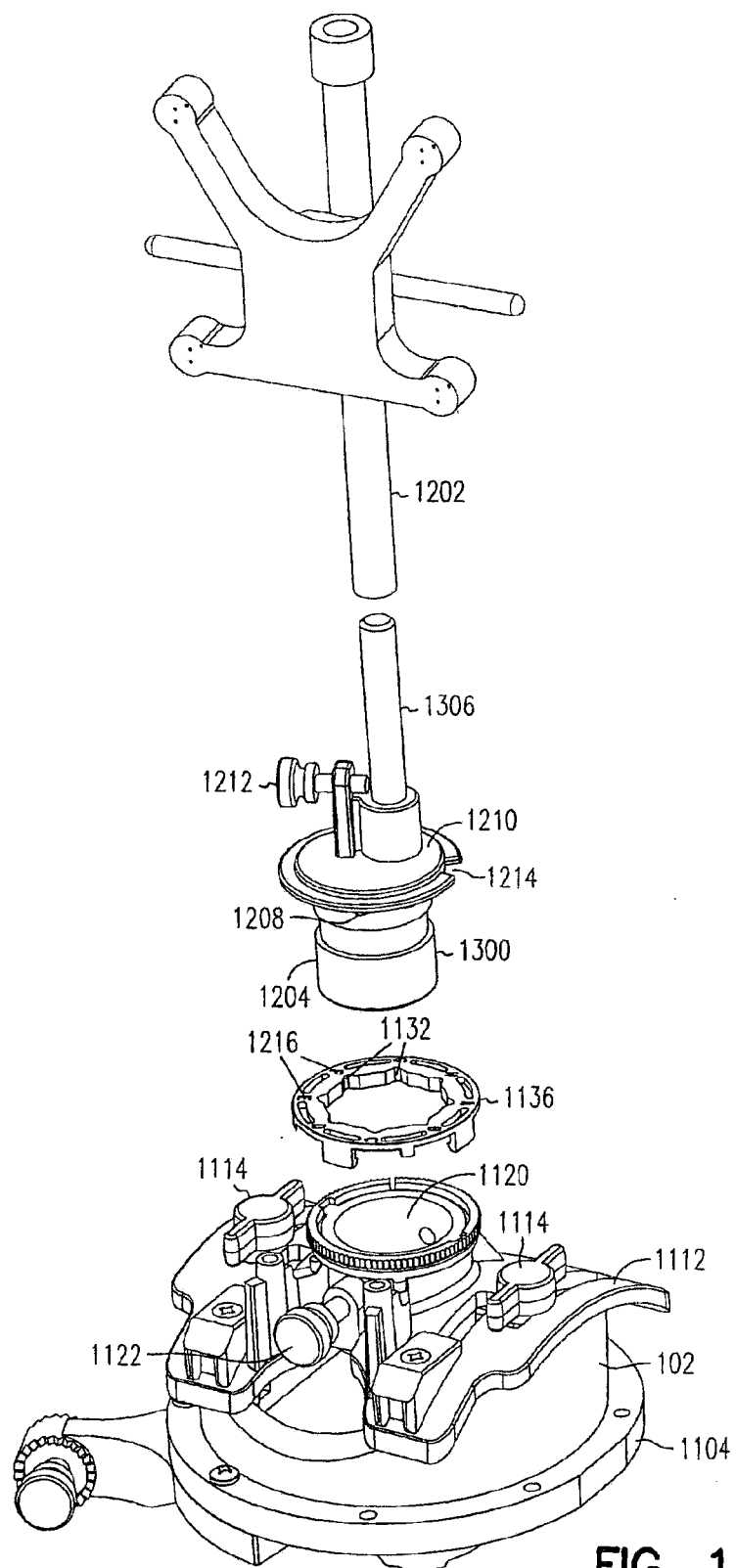

FIG. 13 is an exploded view of a fixture assembly including the trajectory guide, alignment ring, offset alignment guide, and the orienting fixture.

Figure 14:
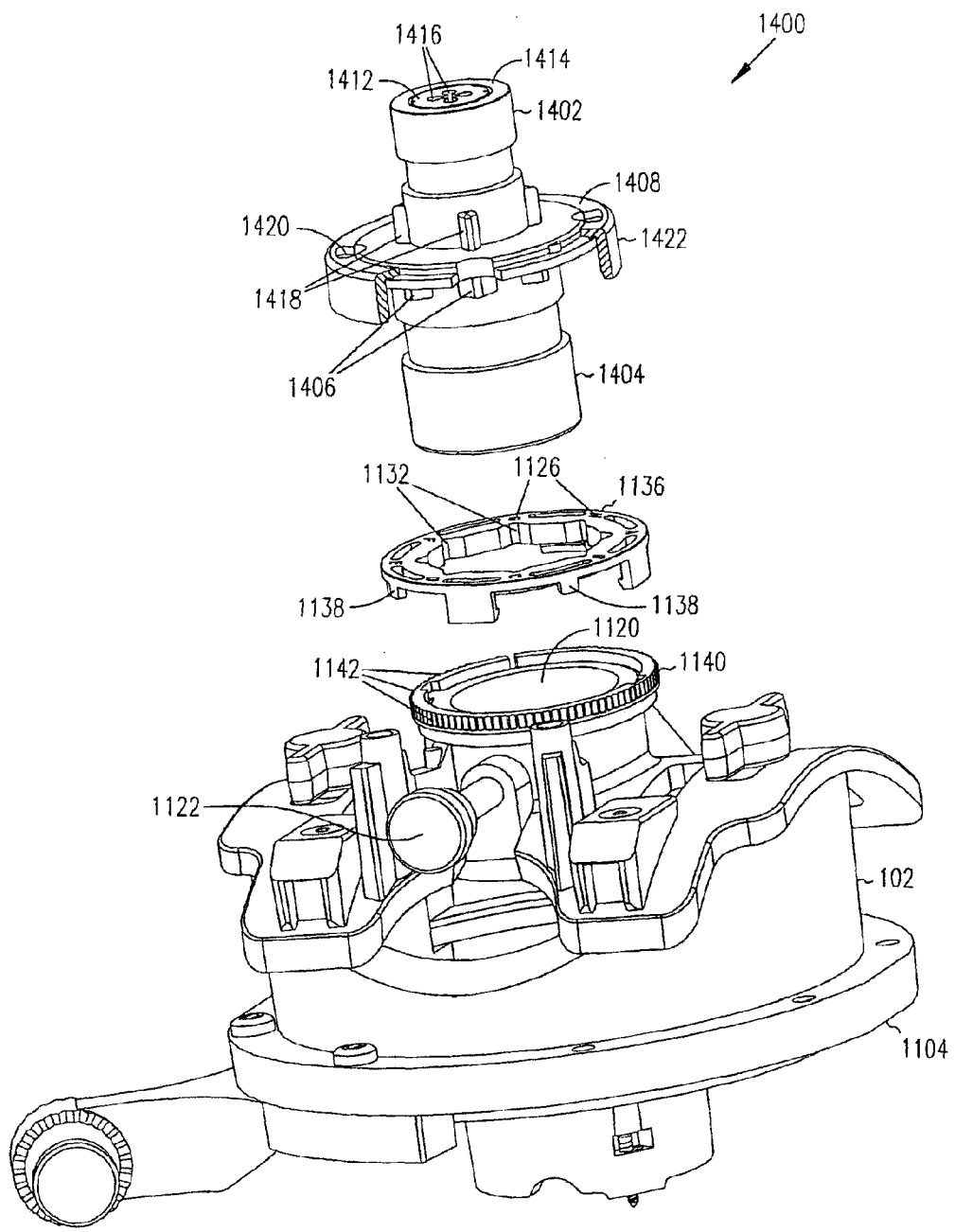

FIG. 14 is a partial section and exploded view of a fixture assembly including the trajectory guide, alignment ring, and centered instrument guide.

Figure 15:
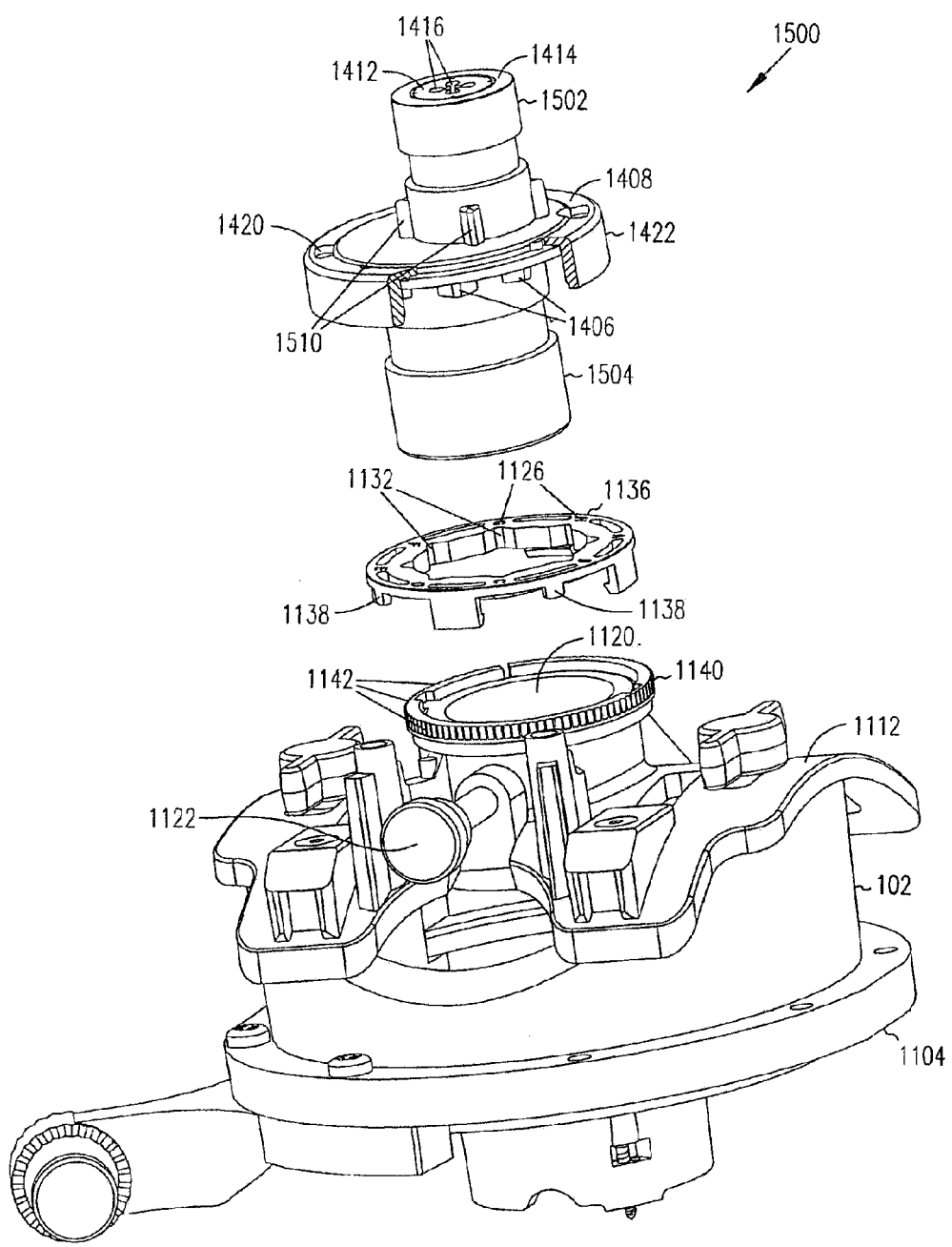

FIG. 15 is a partial section and exploded view of a fixture assembly including the trajectory guide, alignment ring, and offset instrument guide.

Figure 16A:
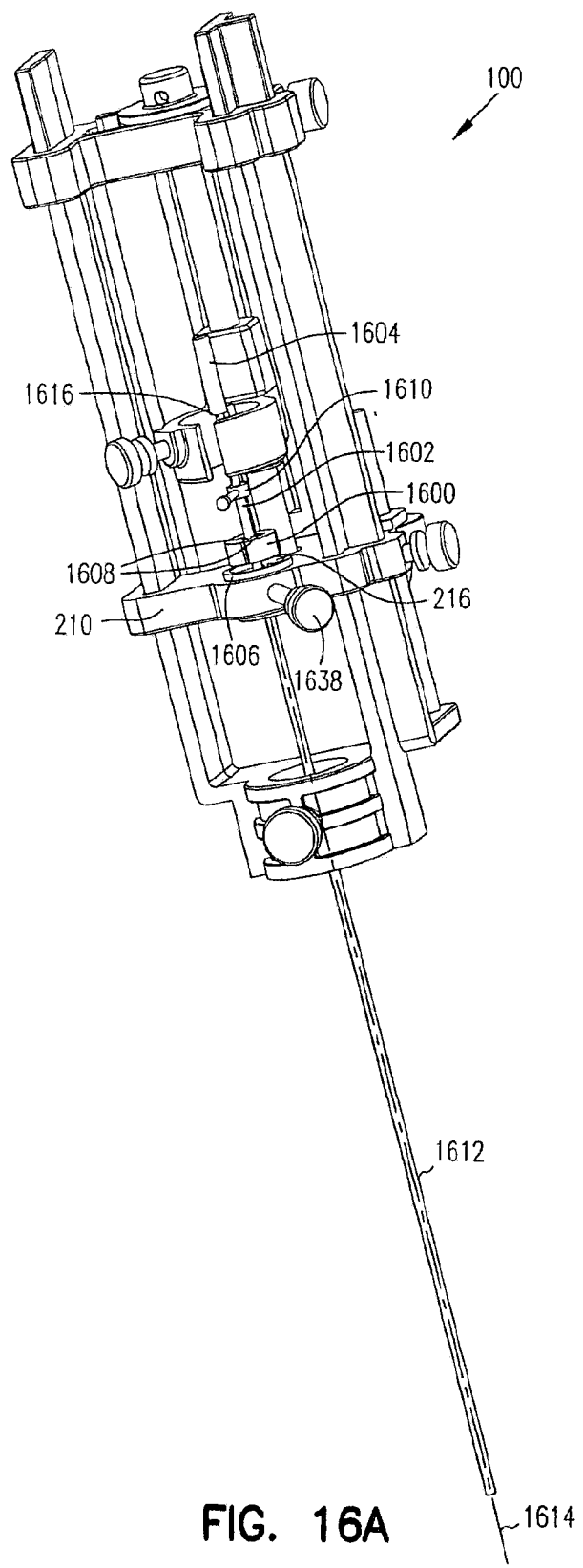

FIG. 16A is an exploded view showing the normalizing stage, guide tube stop, guide tube, and obturator.

Figure 16B:
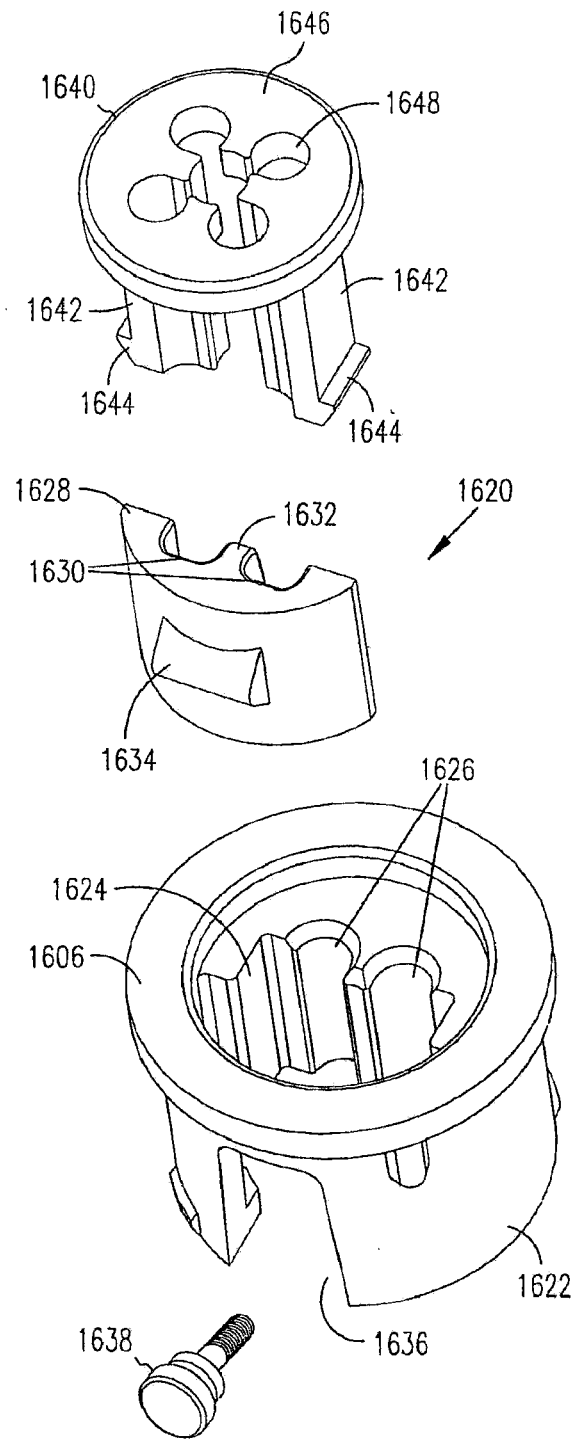

FIG. 16B is an exploded view of the guide tube stop.

Figure 17:
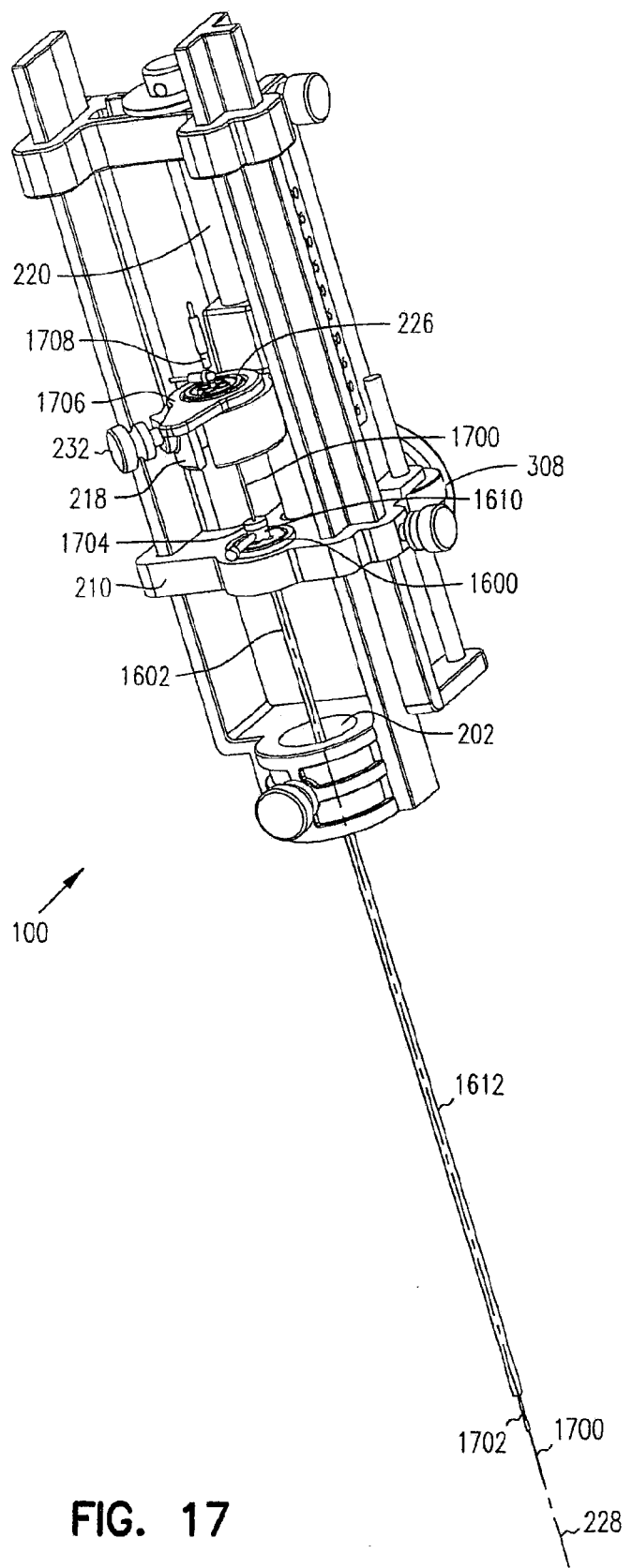

FIG. 17 is a perspective view showing the normalizing stage, guide tube stop, guide tube, spacer tube, instrument retaining assembly, and an instrument.

Figure 18:
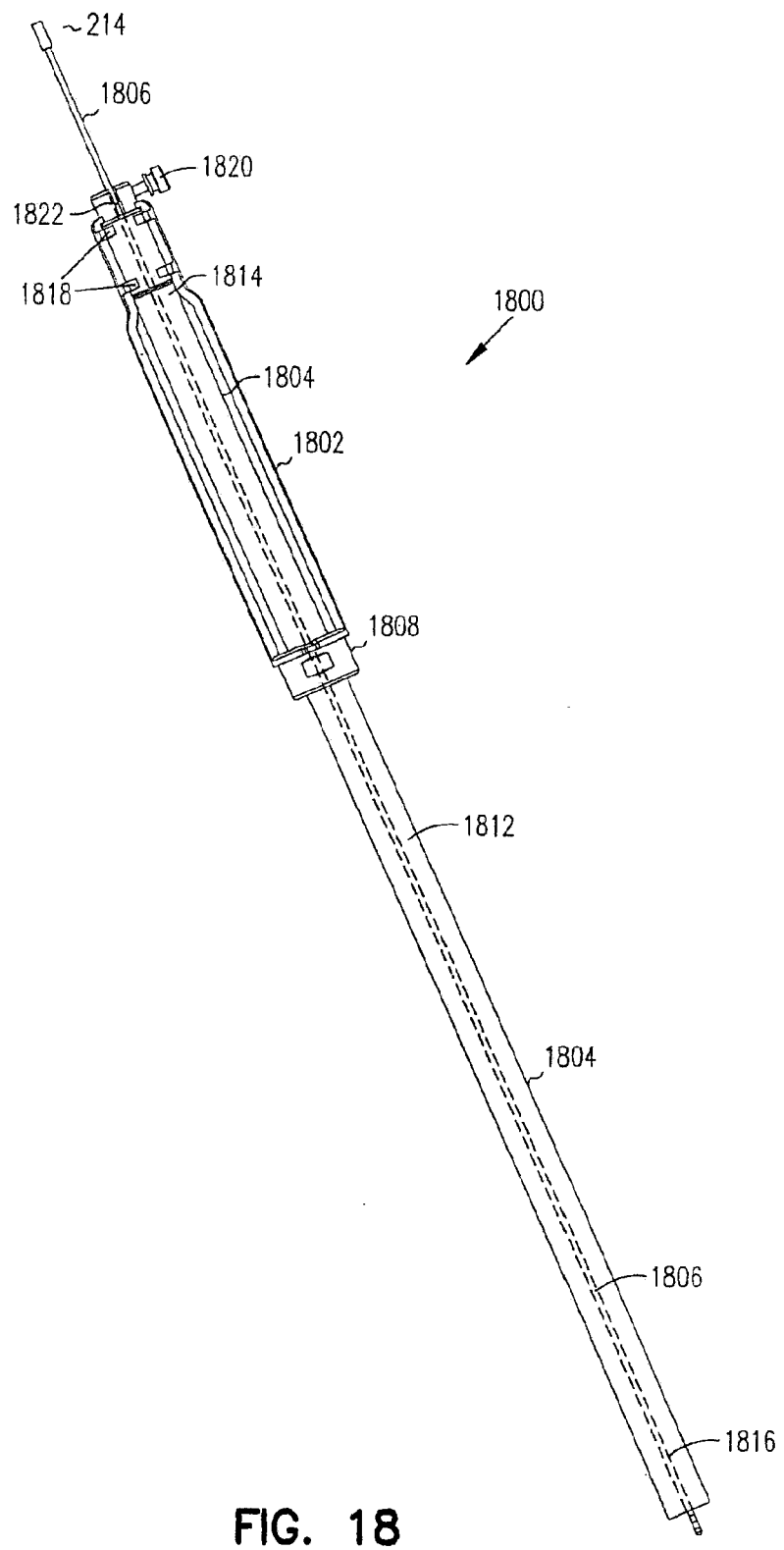

FIG. 18 is a front view of a bracket assembly including the bracket, measurement tube, and an instrument.

Figure 19:
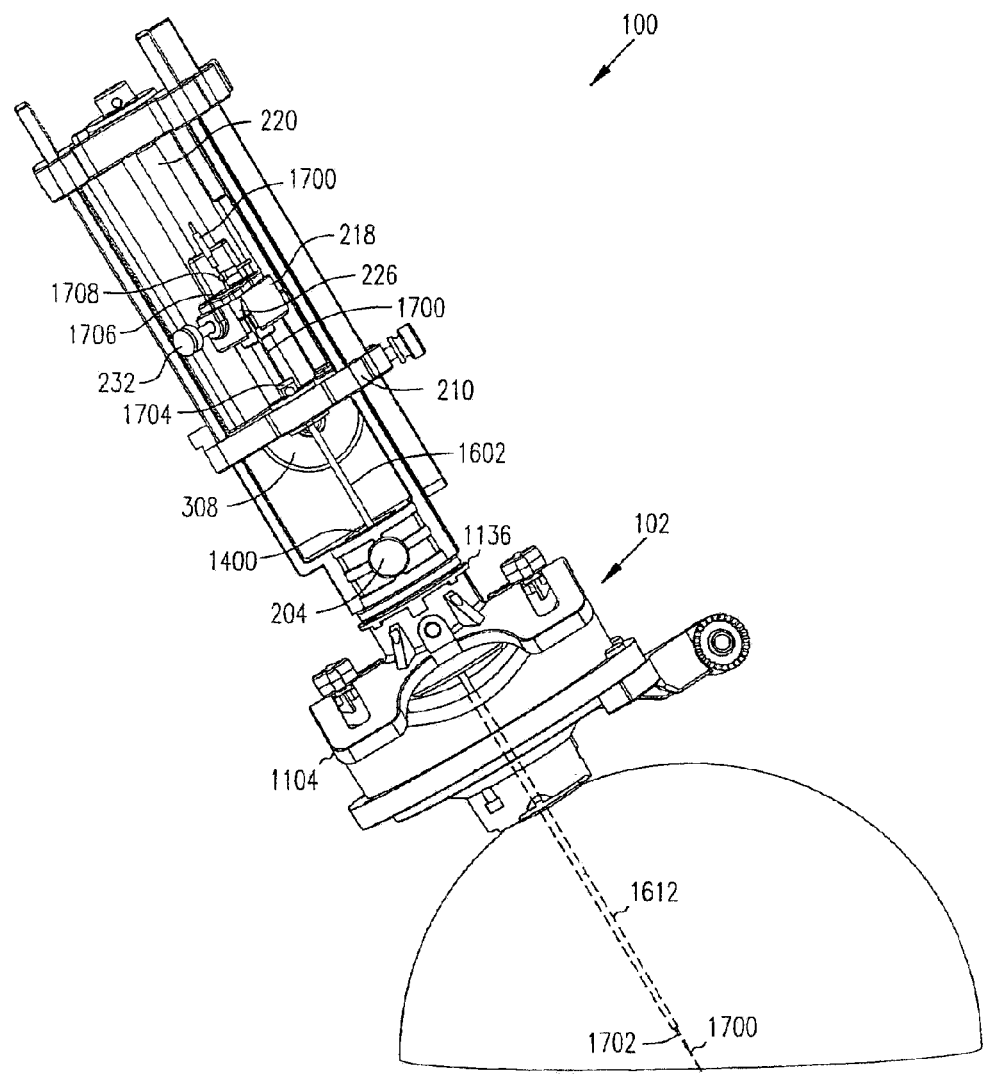

FIG. 19 is a perspective view showing the normalizing stage, guide tube stop, guide tube, spacer tube, instrument, instrument guide, trajectory guide, and instrument immobilizer coupled to the skull.

Figure 20:
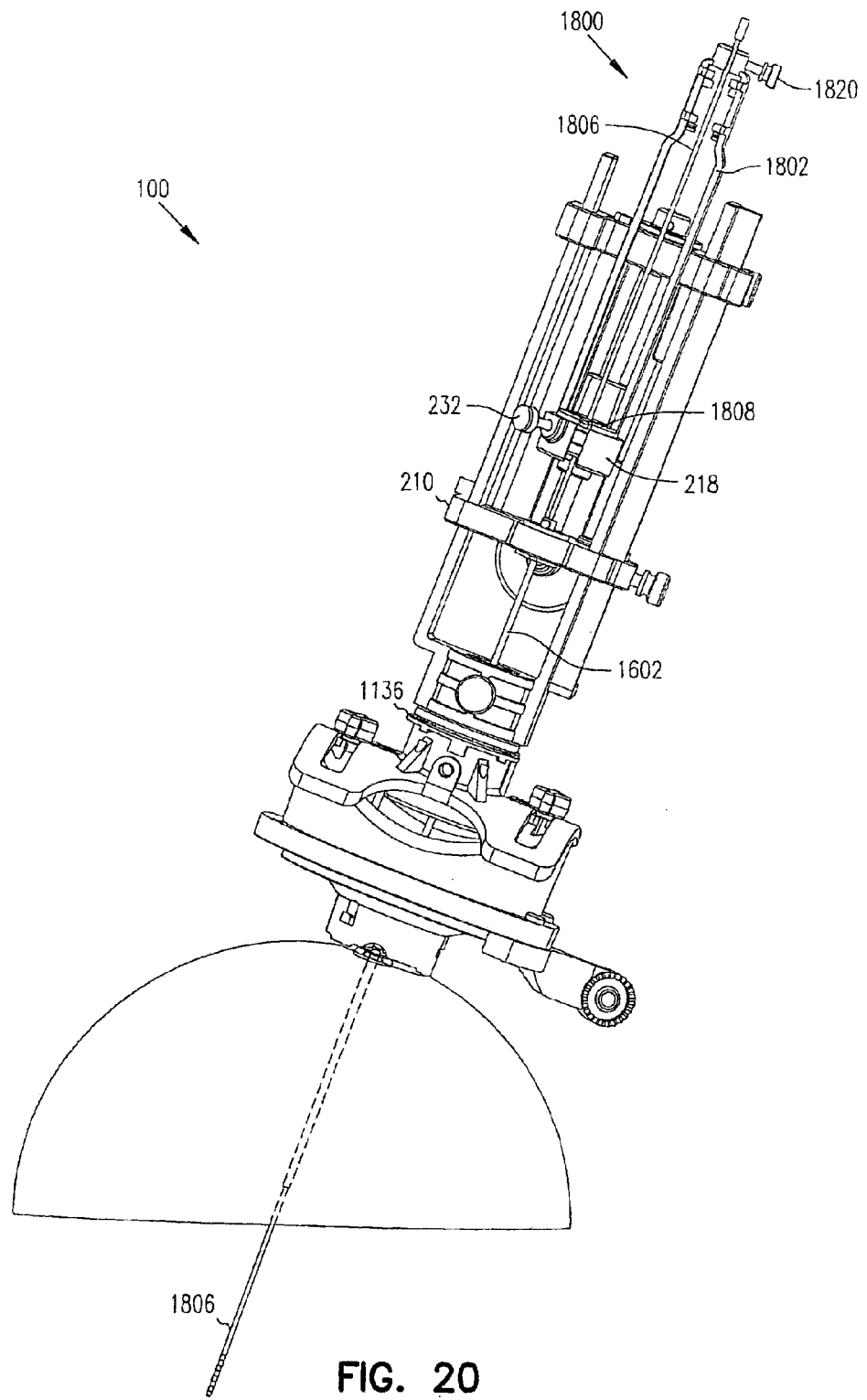

FIG. 20 is a perspective view showing the normalizing stage, guide tube stop, guide tube, bracket, instrument, instrument guide, trajectory guide, and instrument immobilizer coupled to the skull.

Figure 21:
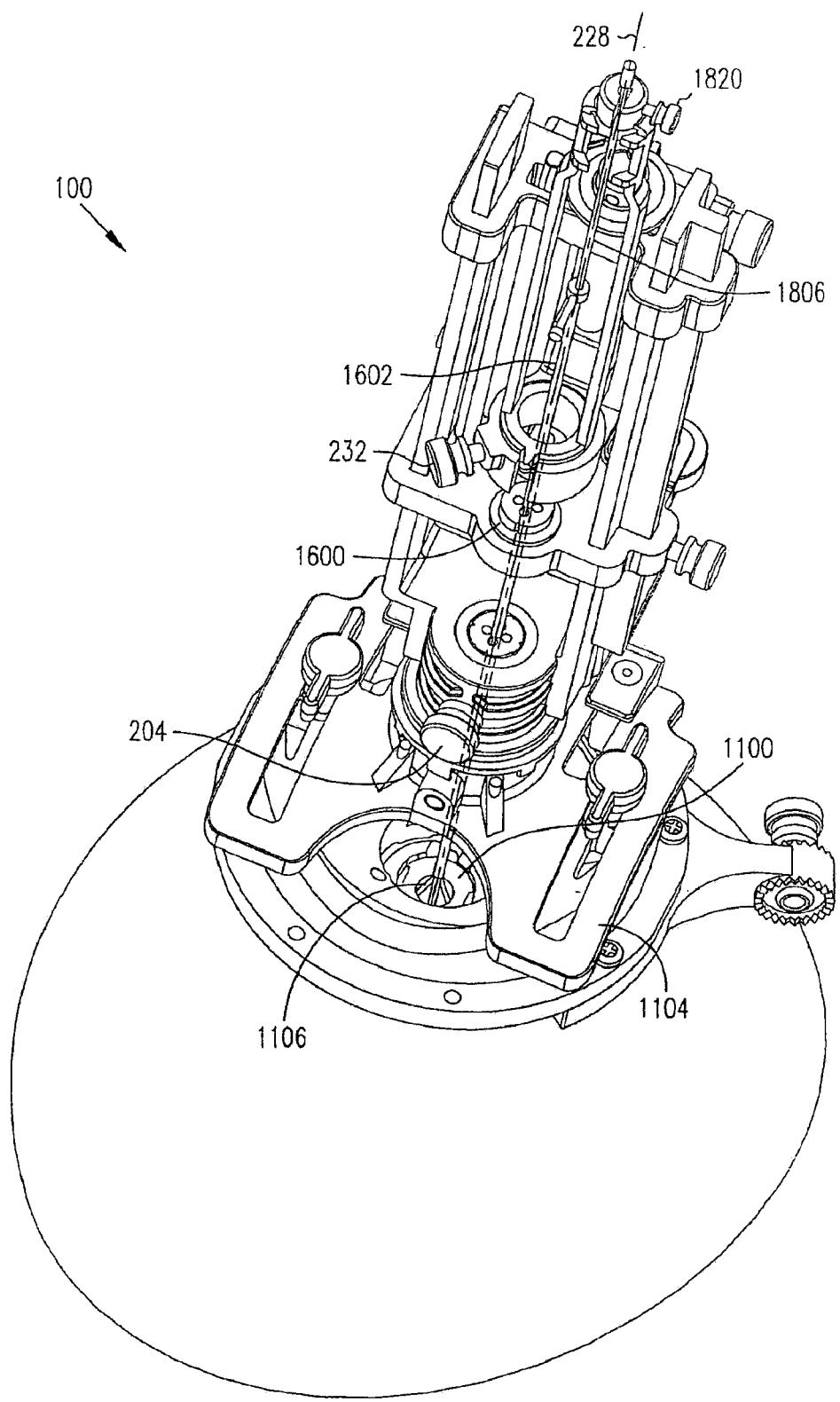

FIG. 21 is a perspective view showing the normalizing stage, bracket, instrument guide, instrument immobilizer, trajectory guide, instrument, guide tube stop, and guide tube in an intermediate position.

Figure 22:
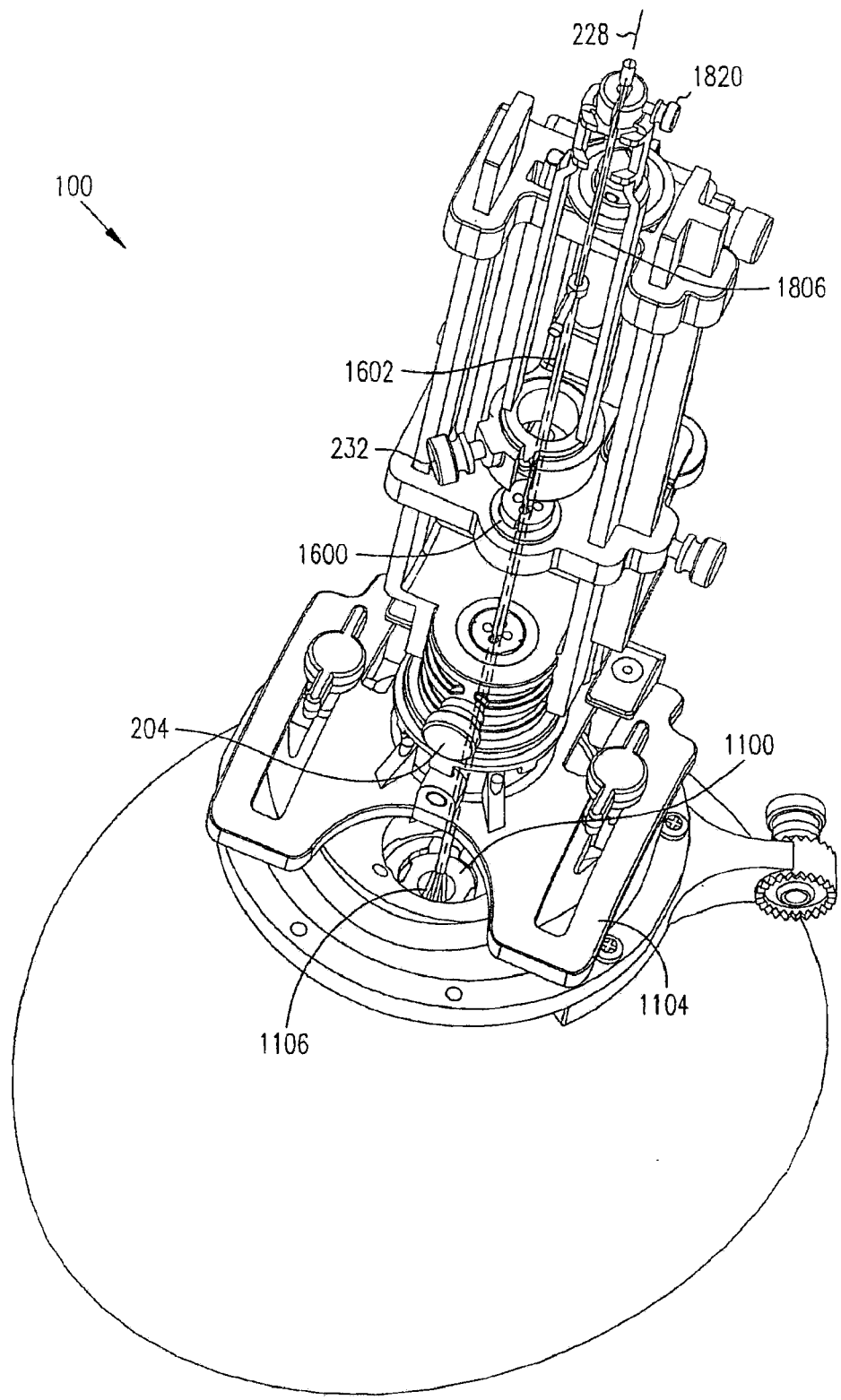

FIG. 22 is a perspective view showing the normalizing stage, bracket, instrument guide, guide tube stop, guide tube, trajectory guide, instrument, and the instrument immobilizer engaged to the instrument.

Figure 23:
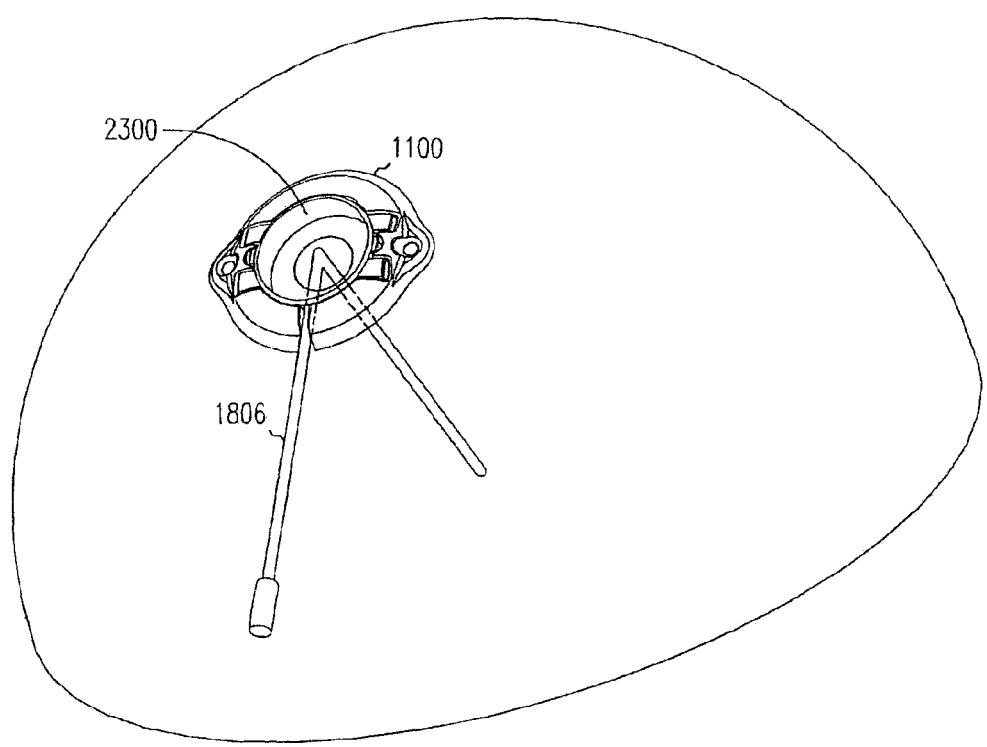

FIG. 23 is a perspective view showing the instrument immobilizer, an instrument bent over, and a cap engaged to the instrument immobilizer.

Figure 24:
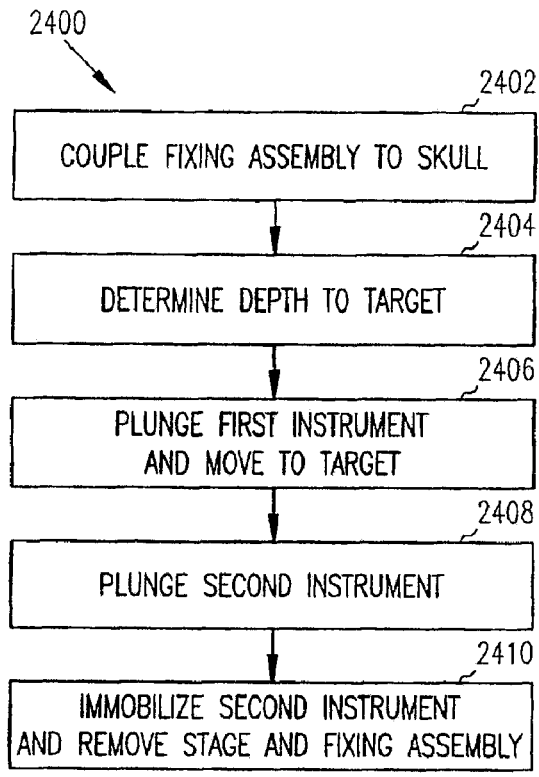

FIG. 24 is a block diagram showing generally an example for using a normalizing stage apparatus and attendant devices.

Figure 25:
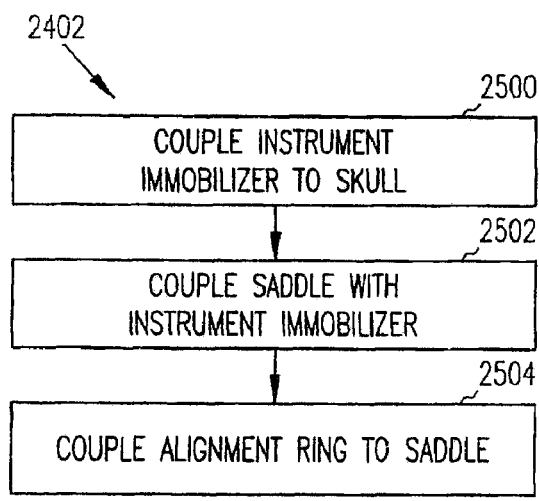

FIG. 25 is a block diagram showing in more detail an example for coupling a fixing assembly to the skull.

Figure 26:
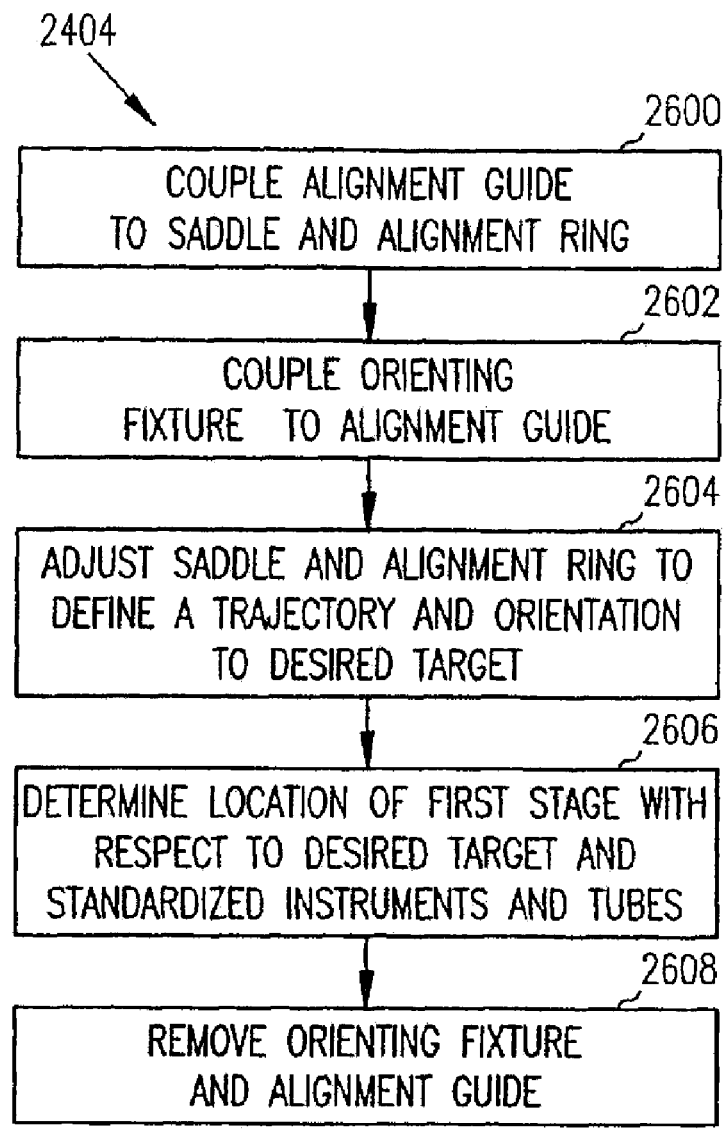

FIG. 26 is a block diagram showing in more detail an example for determining a position of the moveable stage of the normalizing stage apparatus relative to a desired target area.

Figure 27:
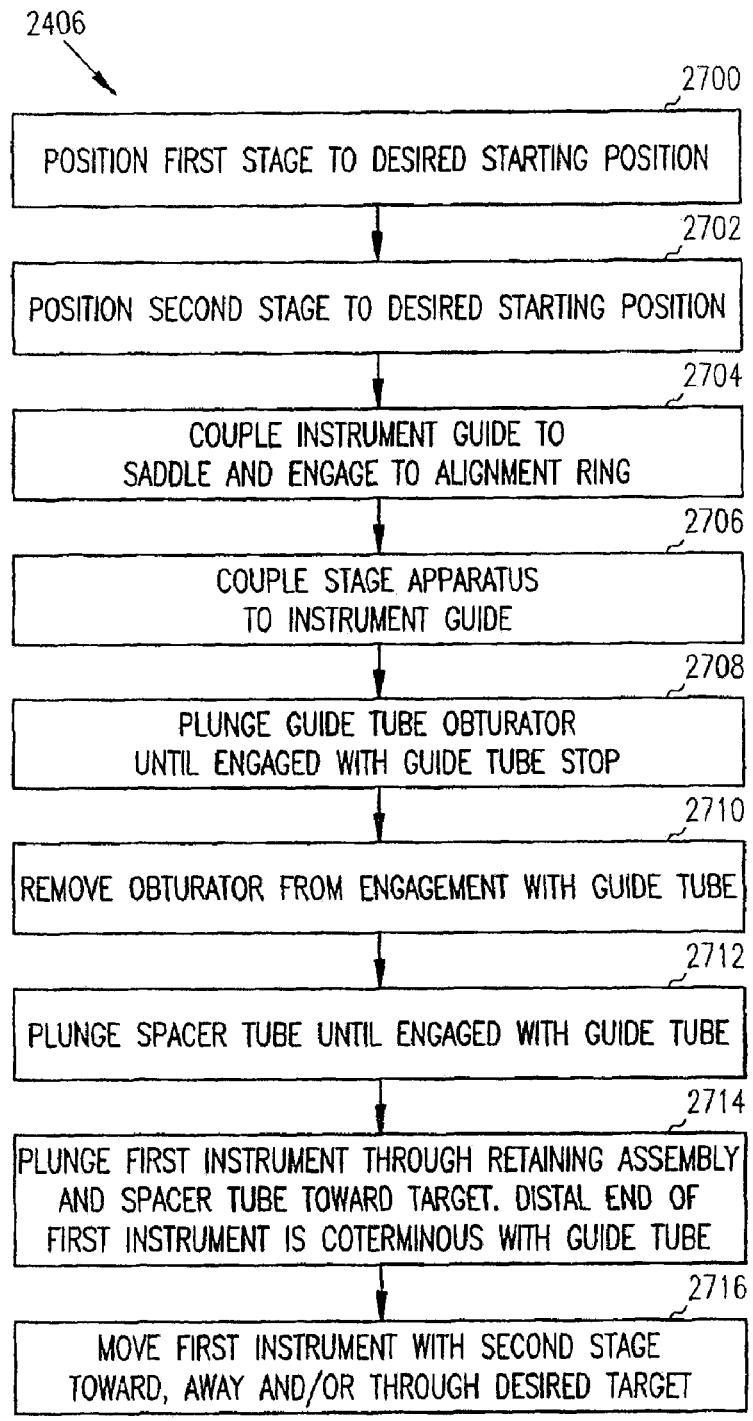

FIG. 27 is a block diagram showing in more detail an example for plunging and advancing an instrument to the desired target area.

Figure 28:
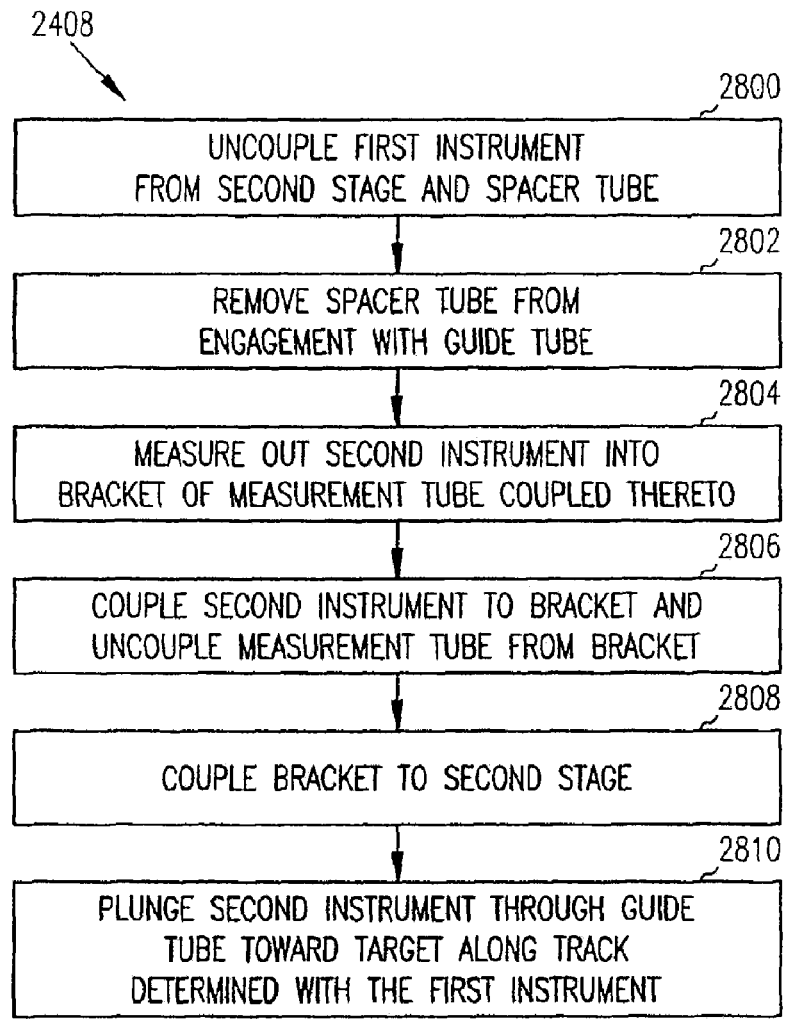

FIG. 28 is a block diagram showing in more detail an example for plunging another instrument to the desired target area.

Figure 29:
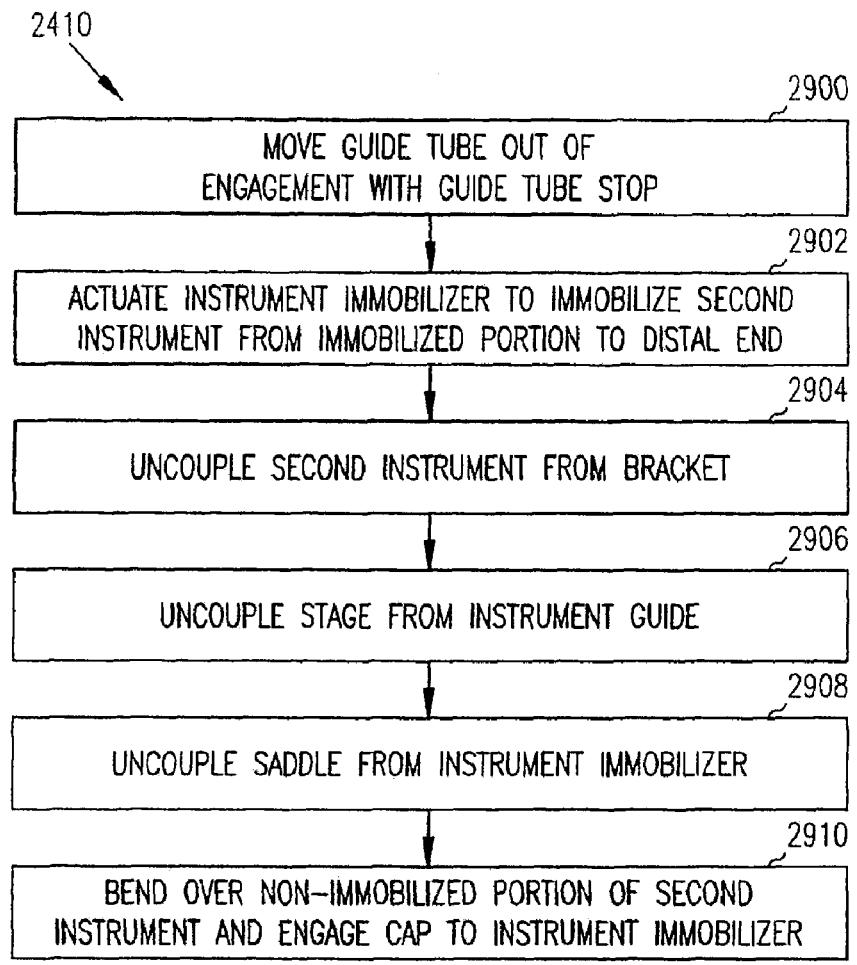

FIG. 29 is a block diagram showing in more detail an example for immobilizing the other instrument and removing the normalizing stage apparatus and fixing assembly.

Corresponding reference numerals indicate corresponding parts throughout the several views of the drawings.

DETAILED DESCRIPTION

Example embodiments will now be described more fully with reference to the accompanying drawings.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated references(s) should be considered supplementary to that of this documents; for irreconcilable inconsistencies, the usage in this document controls.

Figure 1:
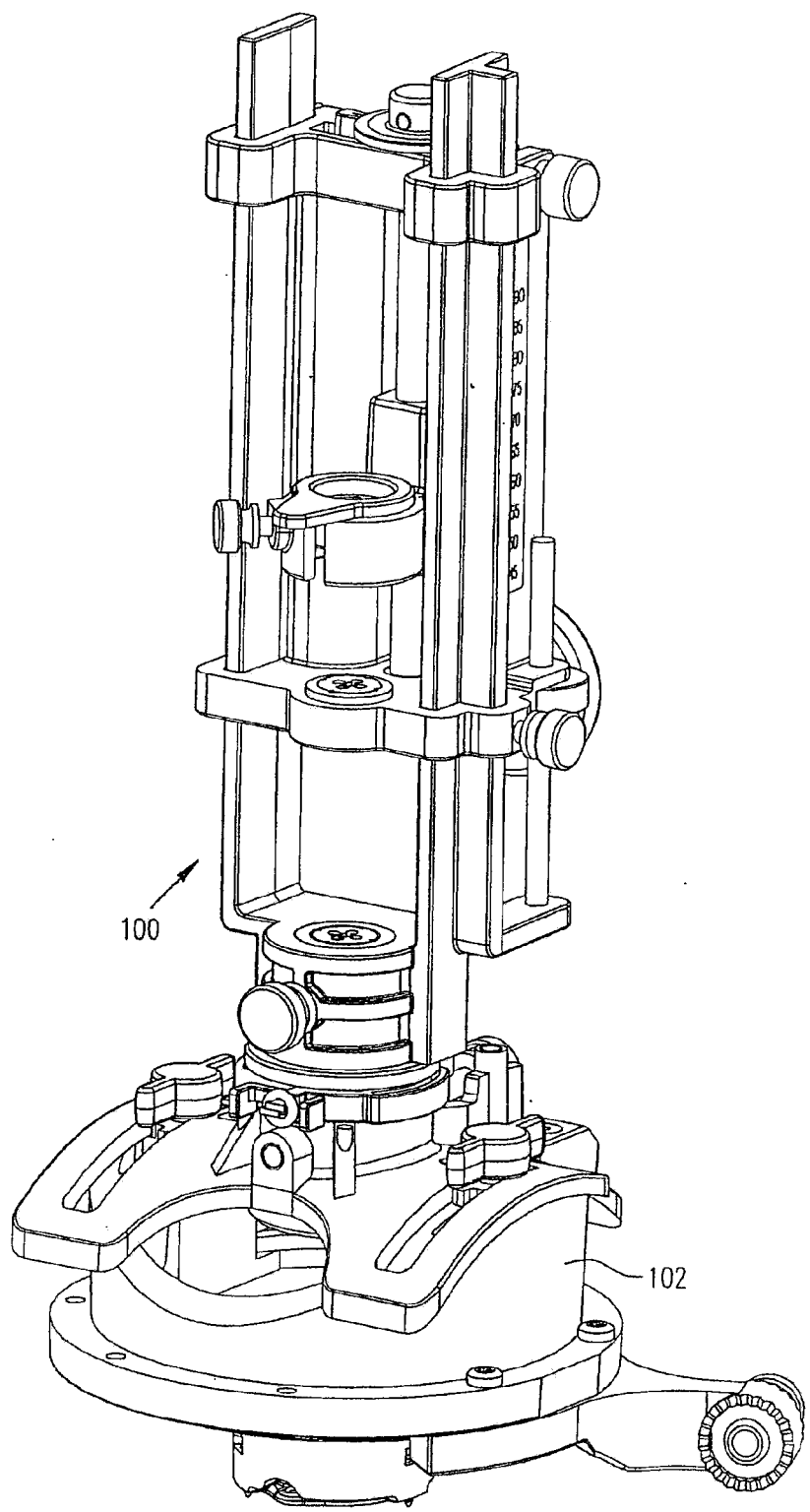
FIG. 1 is a perspective view illustrating one embodiment of a normalizing stage and trajectory guide.

FIG. 1 is a perspective view illustrating generally a normalizing stage apparatus 100 for positioning an instrument using a stage positioned at a known desired (e.g., predetermined) distance from a target. In one example, the target is a location in a brain. The normalizing stage apparatus 100 is coupled to a patient through a fixture assembly 102, sometimes referred to as a trajectory guide. The fixture assembly 102 is operable to position the normalizing stage 100 in a desired orientation to provide a fixable desired trajectory to the target.

Figure 2:
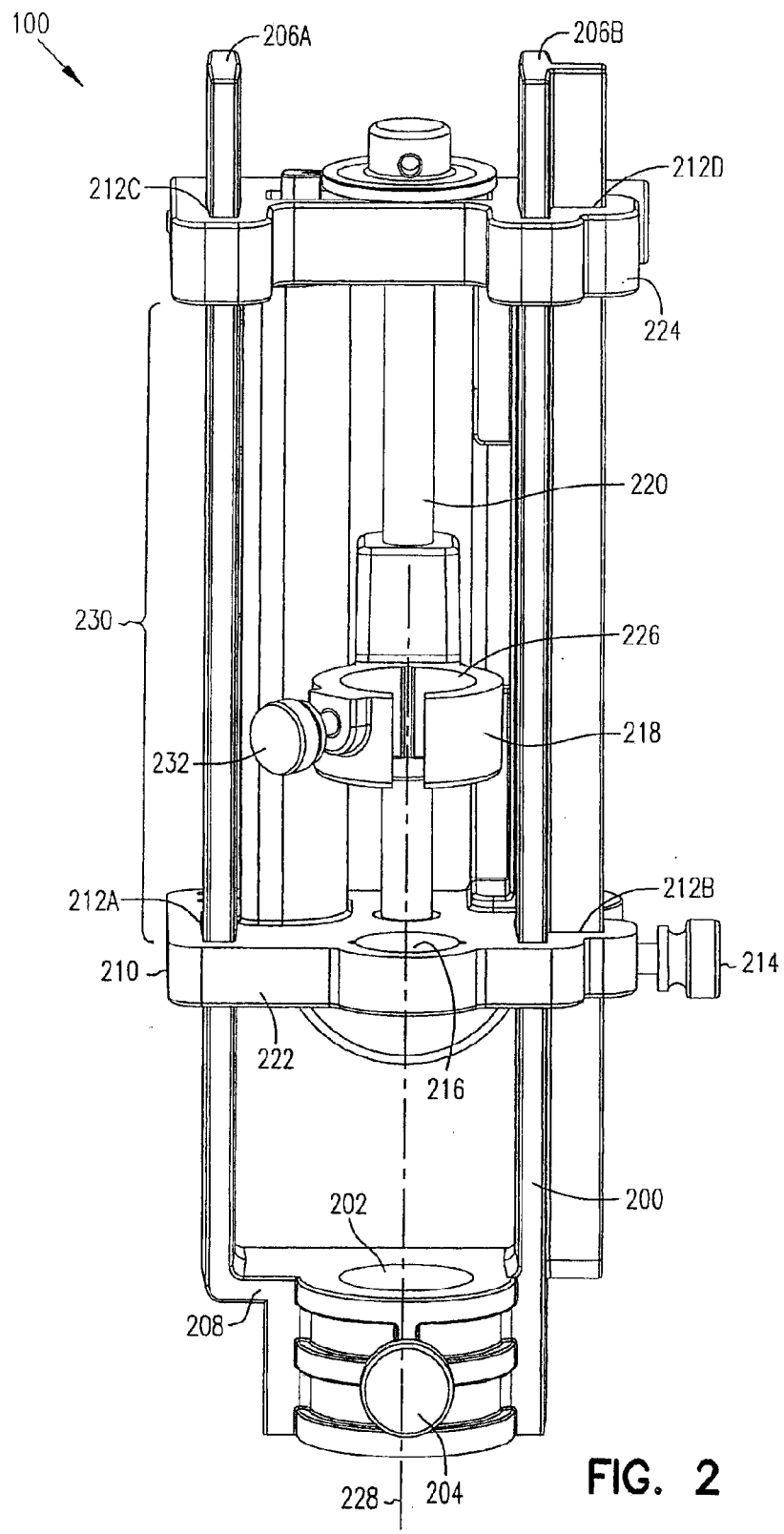
FIG. 2 is a perspective view of one embodiment of the normalizing stage.

FIG. 2 is a front perspective view of a portion of the normalizing stage 100, which includes a base 200. In this example, an inner surface of the base 200 defines a socket 202, for an instrument guide (described below). A thumb screw 204 or other fixation devices extends through the base 200 and into the socket 202, in this example. The thumb screw 204 is operable to engage an instrument guide and fixedly couple the normalizing stage 100 to the instrument guide. The base 200 further includes guide rails 206A, 206B that extend from a lower portion 208. The longitudinal axis of the socket 202 defines a trajectory 228. The guide rails 206A, 206B are substantially parallel to the trajectory 228 defined by the socket 202. In this example, one of the guide rails 206B has a "T" cross section and the remaining guide rail 206A has an approximately rectangular cross section. In another example, the guide rails 206A, 206B both have approximately rectangular cross sections or other geometries that allow for slidable movement along the guide rails 206A, 206B.

A first stage 210 is coupled to the guide rails 206A, 206B. In this example, the first stage 210 includes a lower portion 222 and upper portion 224. The first stage 210 includes four guide rail lumens, two guide rail lumens 212A, 212B extend through the lower portion 222 and another two guide rail lumens 212C, 212D extend through the upper portion 224. The guide rail lumens 222 are dimensioned and configured to slidably couple with the guide rails 206A, 206B. This enables movement of the first stage 210 along the trajectory 228 defined by the socket 202. Additionally, the span 230 between the upper guide rail lumens 212C, 212D and lower guide rail lumens 212A, 212B aids in preventing unwanted lateral or rotational translation of the stage 210 with respect to the trajectory 228. In other words, the sliding relationship of the guide rails 206A, 206B to the guide rail lumens 212A, B, C, D of the first stage 210 constrains lateral movement of the first stage with respect to the trajectory 228, while allowing movement along the trajectory. A thumb screw 214 or other fixation device extends through a portion of the first stage 210 and into the guide rail lumens 212B. The thumb screw 214 is operable to engage one of the guide rails 206A, 206B and immobilize the first stage with respect to the base 200. The first stage 210 also includes a lumen 216. The lumen 216 is substantially aligned with the socket 202. When the first stage 210 is advanced along the trajectory 228 the lumen 216 remains aligned with the trajectory 228.

Figure 3:
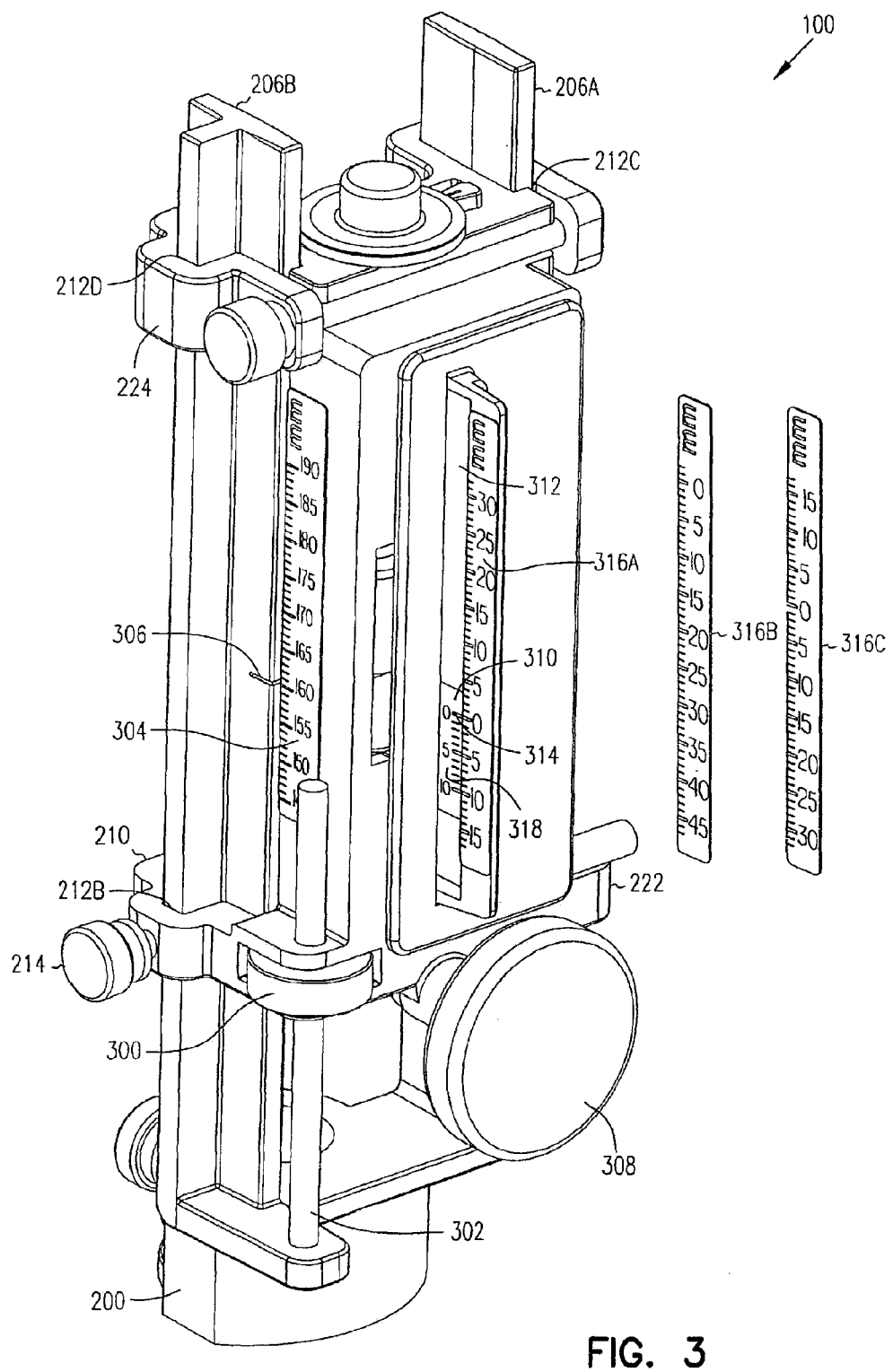
FIG. 3 is another perspective view of one embodiment of the normalizing stage.

FIG. 3 is a rear perspective view of the same portion of the normalizing stage 100 including three scales 316A-C. A first stage actuator 300, comprising a knob in this example, is coupled to the first stage 210. In this example, a stationary screw 302 is coupled to the base 200. In this embodiment, the stationary screw 302 extends through and is coupled to the first stage actuator 300. The stationary screw 302 is also coupled to the first stage 210. In this example, the stationary screw 302 is substantially parallel to the trajectory 228 (FIG. 2). The first stage actuator 300 is operable to advance the first stage 210 along the trajectory 228 by rotating the actuator 300. The first stage actuator 300 includes threads on an inner surface which engage corresponding threads of the stationary screw 302. The stationary screw 302 is long enough to enable a desired position of the first stage 210 with respect to the desired target of substantially all subjects into which an instrument is to be introduced.

In this embodiment a scale 304 is provided, such as along a side of the first stage 210 near a guide rail 206B. The scale 304 is graduated to indicate a range of positions of the first stage 210 with respect to a desired target. A reference mark 306 on a guide rail 206B is positioned to cooperatively indicate, with the graduated scale 304 on the first stage 210, the position of the first stage with respect to the target.

Referring again to FIG. 2, a second stage 218 is movably coupled to the first stage 210. In one example, the second stage 218 is coupled to the first stage 210 by a screw 220 or the like. The screw 220 extends between the lower portion 222 and upper portion 224 of the first stage 210 and is rotatably coupled to each. The second stage 220 includes a lumen having inner threads engaging the threads for screw 220. Additionally, the second stage 218 includes a retaining assembly orifice 226 dimensioned and configured to couple with a retaining assembly, as described below. In this example, the retaining assembly orifice 226 is a broken ring. In another example, the retaining assembly orifice 226 is defined by a continuous inner surface of the second stage 218. A thumb screw 232 or other fixation device is coupled to and extends through a portion of the second stage 218. The thumb screw 232 is operable to immobilize an instrument extending through the retaining assembly lumen 226.

FIG. 3 is a perspective view of the normalizing stage 100 As shown in the example illustrated in FIG. 3, an actuator knob 308 is coupled to the first stage 210. The actuator knob 308 is connected by cooperative gearing to the screw 220 (FIG. 2), in this example. The knob 308 is thus operable to move the second stage 218 along the screw 220. Additionally in this example, the second stage 218 includes a protrusion 310 which extends from a surface of the second stage through a slot 312 in the first stage 210. The protrusion 310 maintains the alignment of the second stage 218 to the first stage 210 during rotation of the knob 308, which turns the screw 220. Specifically, the slot 312 helps the retaining assembly orifice 226 to remain aligned with the guide tube stop lumen 216 and instrument guide lumen 202.

In the example shown in FIG. 3, the protrusion 310 also includes a reference marking 314. The reference marking 314 indicates the position of an instrument with respect to the standardized distance to target. In one example, a scale 316A-C is included on the first stage 210. The scale 316A-C is disposed adjacent to the slot 312. In one example, the reference marking 314 is read against the scale 316A to determine the position of the instrument with respect to the target. Optionally, the scale 316A and marking 314 show the position of a tip of the instrument with respect to the target. In another example, scale 316B is included on the first stage 210 in place of scale 316A. Scale 316B in cooperation with the marking 314 has the "0" of the scale 316B corresponding to the top of the travel of the second stage 218. Scale 316C, in yet another example, cooperates with marking 314 so the "0" of the scale 316C corresponds to an approach distance remote from the desired target. As a result, when the mark 314 is located at the "0" of the scale 316C the tip of the instrument is positioned a desired (e.g., predetermined) approach distance (e.g. 15 millimeters) from the desired target. In still another example, the scales 316A-C are adjustable (for example, removable and reattachable, such as with an adhesive backing) and is positioned along the slot 312 according to the needs of the physician or technician. The mark 314 is part of a vernier scale 318, in another option, and the vernier scale 318 provides another degree of precision for measuring the distance from the instrument to the desired target.

Figure 4:
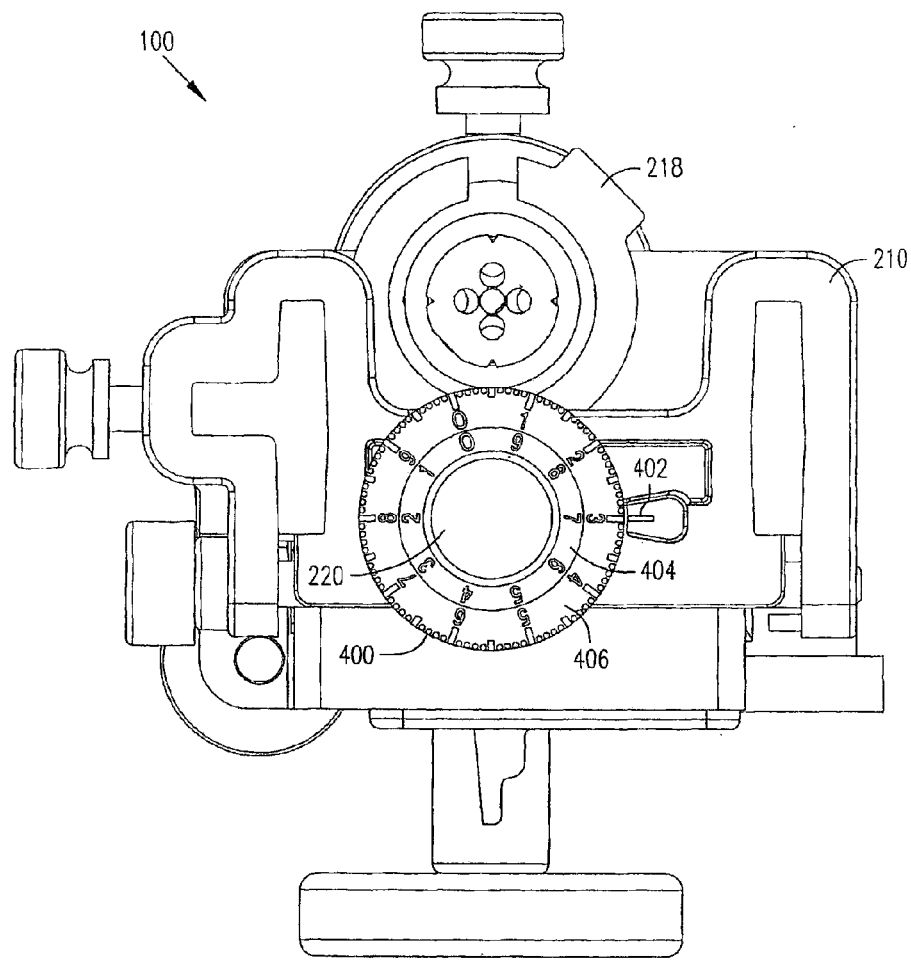
FIG. 4 is a top view of one embodiment of the normalizing stage.

FIG. 4 is a top view of one embodiment of the normalizing stage 100. A circular fine scale 400 is coupled to the top of the screw 220. The screw 220 is threaded. Each rotation of the screw 220 correspond to one rotation of the fine scale 400. In one example, one rotation of the screw 220 moves the second stage 218 by 1 mm toward or away from the target. In this example, the fine scale 400 is graduated so one rotation of the scale indicates 1 mm of advancement, and 0.1 mm and 0.01 mm increments are also indicated. A reference marking 402 is included on the first stage 210 to indicate the position of the second stage 218 when reading the fine scale 400. The scale 400, in one option, includes an inner scale 404 and an outer scale 406. The inner scale 404 is used to measure translation of the second stage 218 from the "0" marking on scale 316A, 316C to a measure above "0" in another option (e.g. from 10.6 millimeters to 10.7 millimeters above "0"). In yet another option, the outer scale 406 is used to measure translation of the second stage 218 from the "0" marking on the scale 316A, 316C to a measure below "0", for instance from 4.0 millimeters to 4.1 millimeters below "0." As a result, the inner scale 404 is used to measure translation of the second stage 218 above "0" and the outer scale 406 is used to measure translation of the second stage 218 below "0."

Figure 5:
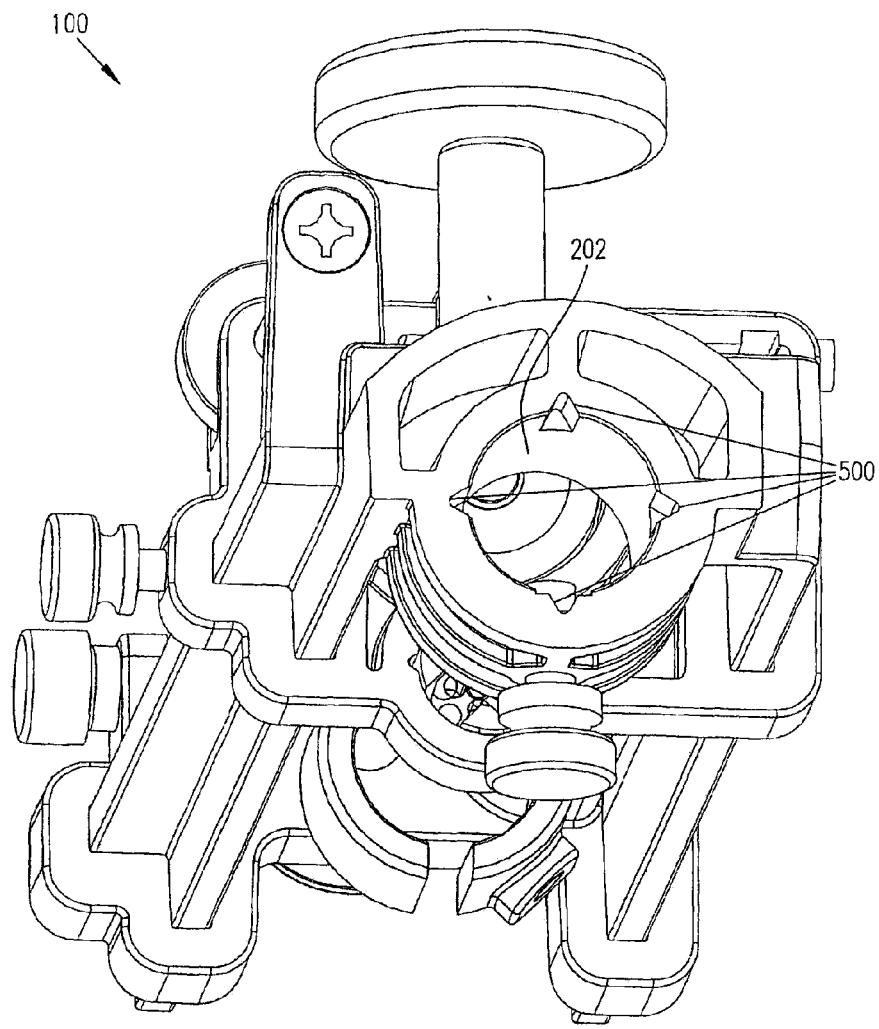
FIG. 5 is a perspective of one embodiment of the normalizing stage.

FIG. 5 is a bottom perspective view of one embodiment of the normalizing stage 100. The socket 202 includes keyed slots 500 or the like within the base 200. When the normalizing stage 100 is coupled to an instrument guide (described below), the surfaces defining the keyed slots 500 engage corresponding keys present on the instrument guide. Unwanted rotation of the normalizing stage 100 is thus prevented with respect to the instrument guide.

Figure 6:
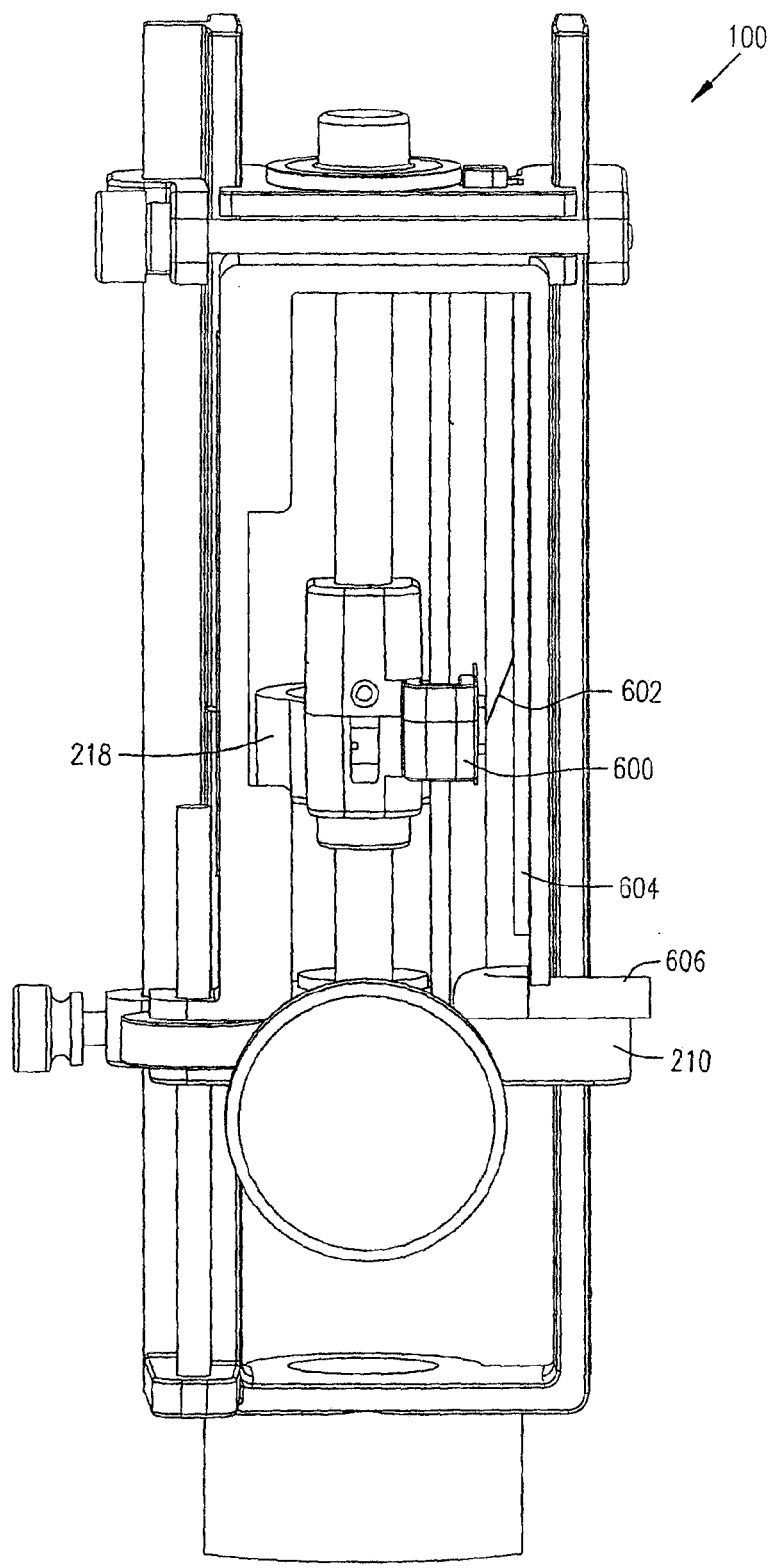
FIG. 6 is a rear view of another embodiment of the normalizing stage having a potentiometer.

FIG. 6 is a rear view of another embodiment of the normalizing stage 100. In this embodiment, the position of the second stage 218 with respect to the first stage 210 is measured by a potentiometer assembly 600. The assembly 600 includes a wiper 602. In this example, the wiper 602 is coupled to the second stage 218. Alternatively, the wiper 602 is coupled to the first stage 210. The wiper 602 electrically contacts and bridges between two elongate resistors 604 physically parallel to one another and coupled to the first stage 210. The resistors 604 are of sufficient length to enable the second stage 218 to advance an instrument toward, away, and/or through a target while still contacting the wiper 602 to measure the position of the second stage 218. In one example, a cable 606 connects the potentiometer assembly 600 to an output device that includes a display screen. The output device displays the location of the second stage 218 according to the position of the wiper 602 with respect to the resistors 604. In another example, the output device displays the location of an instrument with respect to a desired target in a similar manner as with the scales 316A-C (described above). In an alternate example, the resistors 604 are coupled to the second stage 218 and the wiper 602 is coupled to the first stage 210. In another option, supplemental resistors are coupled to the base 200 or the first stage 210 and a supplemental wiper is coupled to the other of the base 200 or the first stage 210. As a result, a potentiometer assembly is used to measure translation of the first stage 210 with respect to the base 200.

Figure 7:
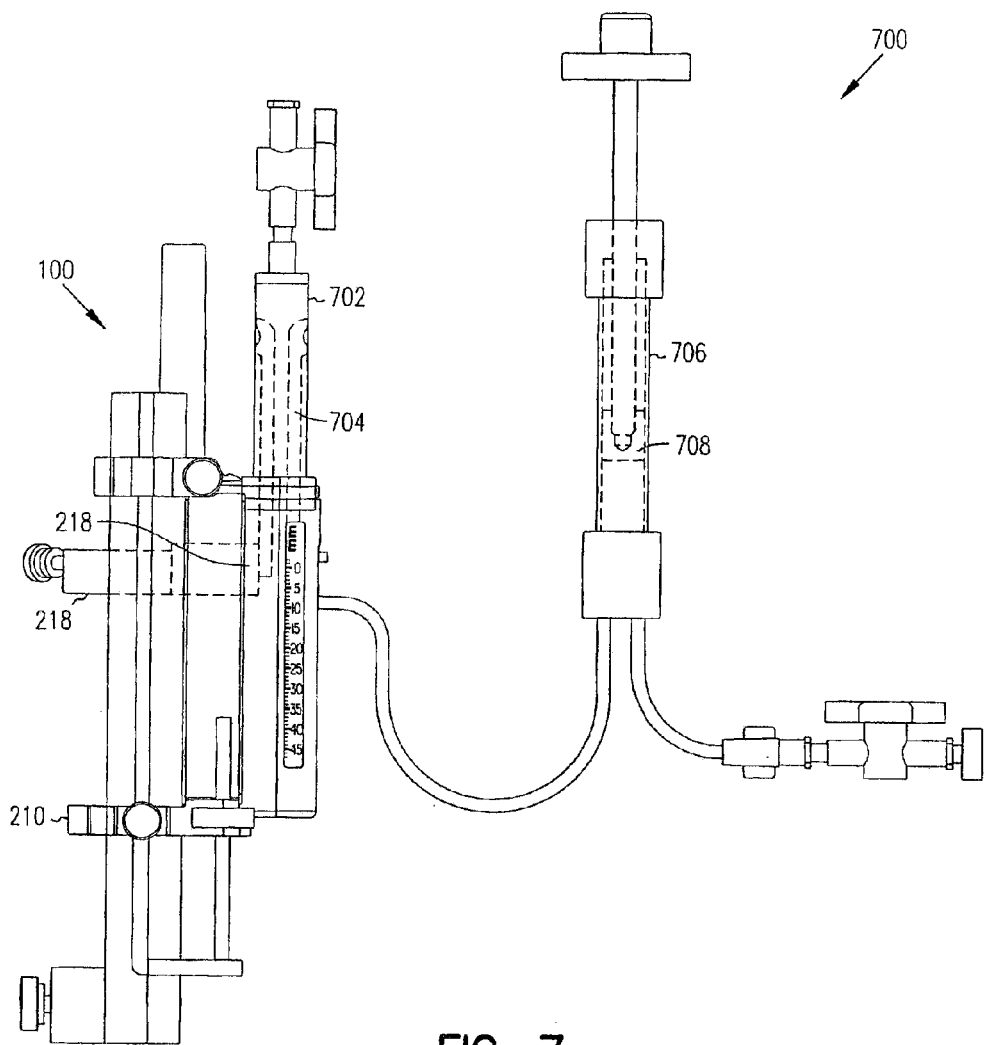
FIG. 7 is a side view of yet another embodiment of the normalizing stage having a hydraulic system.

FIG. 7 illustrates a side view of another embodiment of the normalizing stage 100 that includes a hydraulic system 700. The hydraulic system 700 includes, in fluid communication with each other, a hydraulic cylinder 702, hydraulic piston 704, master hydraulic cylinder 706, and master hydraulic piston 708. The master hydraulic cylinder 706 and piston 708 are operable to actuate the hydraulic cylinder 702 and piston 704. In one example, the hydraulic cylinder 702 and piston 704 move the second stage 218 with respect to the first stage 210.

Figure 8A:
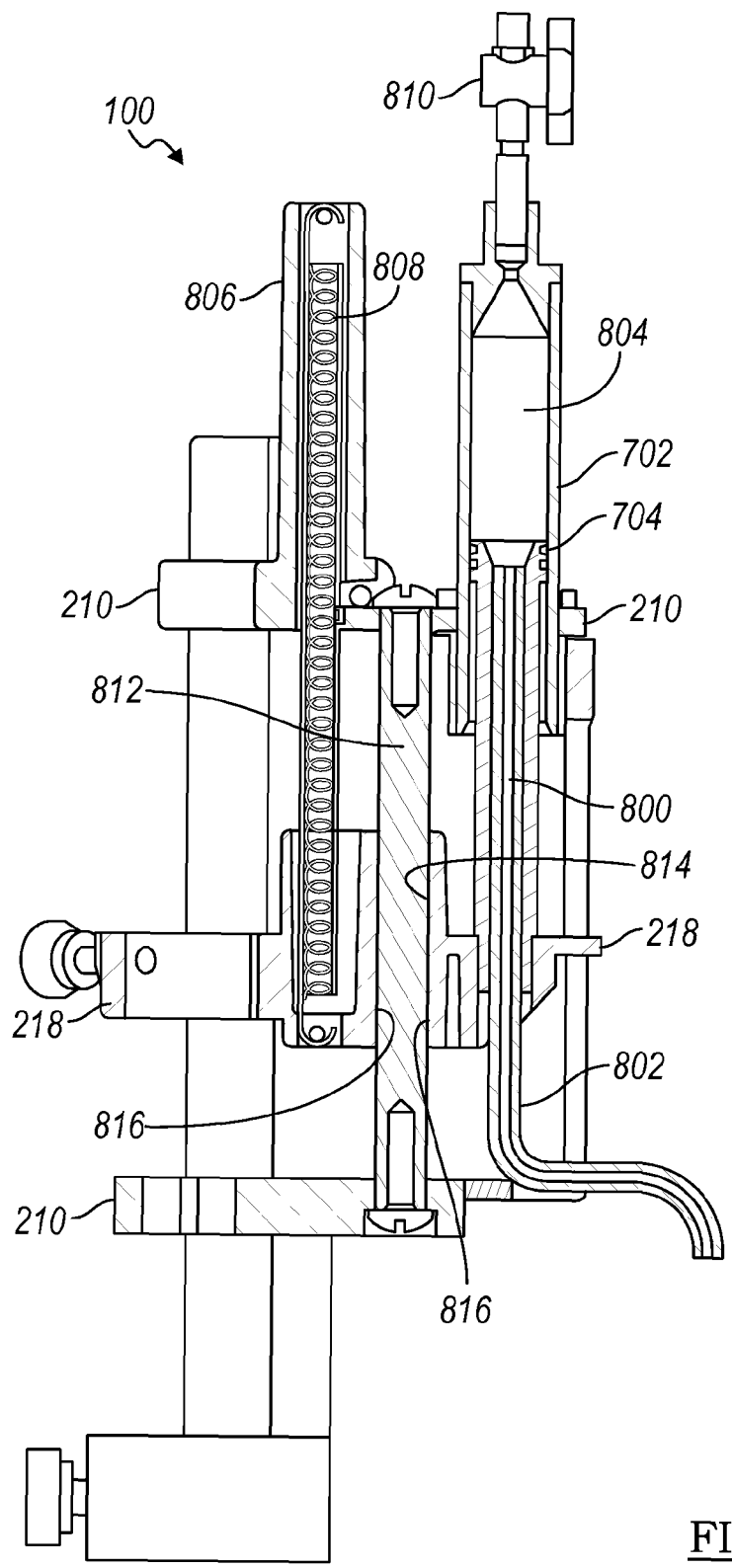
FIG. 8A is a sectional view of yet another embodiment of the normalizing stage.

FIG. 8A is a cross section view of the hydraulic embodiment of the normalizing stage 100. In this example, the hydraulic cylinder 702 is mounted to the first stage 210 and the hydraulic piston 704 is mounted to the second stage 218 (or vice versa). In this example, the hydraulic piston 704 is coupled to the second stage 218 by a piston tube 800. In one example, a hydraulic line 802 coupled to the master piston 708 (FIG. 7) extends through the piston tube 800 and is coupled substantially adjacent to the hydraulic piston 704. In another example, the hydraulic line 802 is coupled to the piston tube 800 at any location along the length of the piston tube 800. In yet another example, the hydraulic line 802 is coupled to the second stage 218 and in fluid communication through a coupling to the piston tube 800. The inner surface of the hydraulic cylinder 702 and hydraulic piston 704 define a first volume 804. The first volume 804 is increased and decreased by actuation of the master cylinder 706 and master piston 708. Changing the first volume 804 advances the piston 704 inside the cylinder 702, which, in turn, advances the second stage 218.

In the example shown in FIG. 8A, a spring housing 806 is coupled to the first stage 210. In this example, the housing 806 is a tubular structure. A spring 808 or the like is coupled to one end of the housing 806, in one example. The other end of the spring 808 is coupled to the second stage 218. In another example, an elastic material, for example an elastomeric membrane is coupled between the housing 806 and the second stage 218. The spring 808 is in tension and maintains a force on the second stage 218. In other words, the spring 808 pulls the second stage 218 and the hydraulic piston 704 toward the fluid filled end of the hydraulic cylinder 702. The incompressibility of hydraulic fluid in the hydraulic cylinder 702 prevents the spring 808 from undesirably advancing the second stage 218. The spring 808 thus maintains a pressurized hydraulic system 700 by pulling the piston 704 toward the cylinder 702. In this example a stopcock valve 810 or the like is coupled to the hydraulic cylinder 702 and is in fluid communication thereto.

The second stage 218, shown in FIG. 8A, is slidably mounted on and guided by a guide rail 812 associated with the first stage 210. Guide surface 814 of the second stage 218 provides smooth linear motion of second stage 218 along an interface 816 with the guide rail 812. Guide surface 814, in one example is integral with the second stage 218 (FIG. 8A). In another example, guide surface 814 includes a friction-reducing insert or coating made of a bearing material, including but not limited to, TEFLON. Optionally, the coating or insert is coupled along the guide rail 812.

Figure 8B:
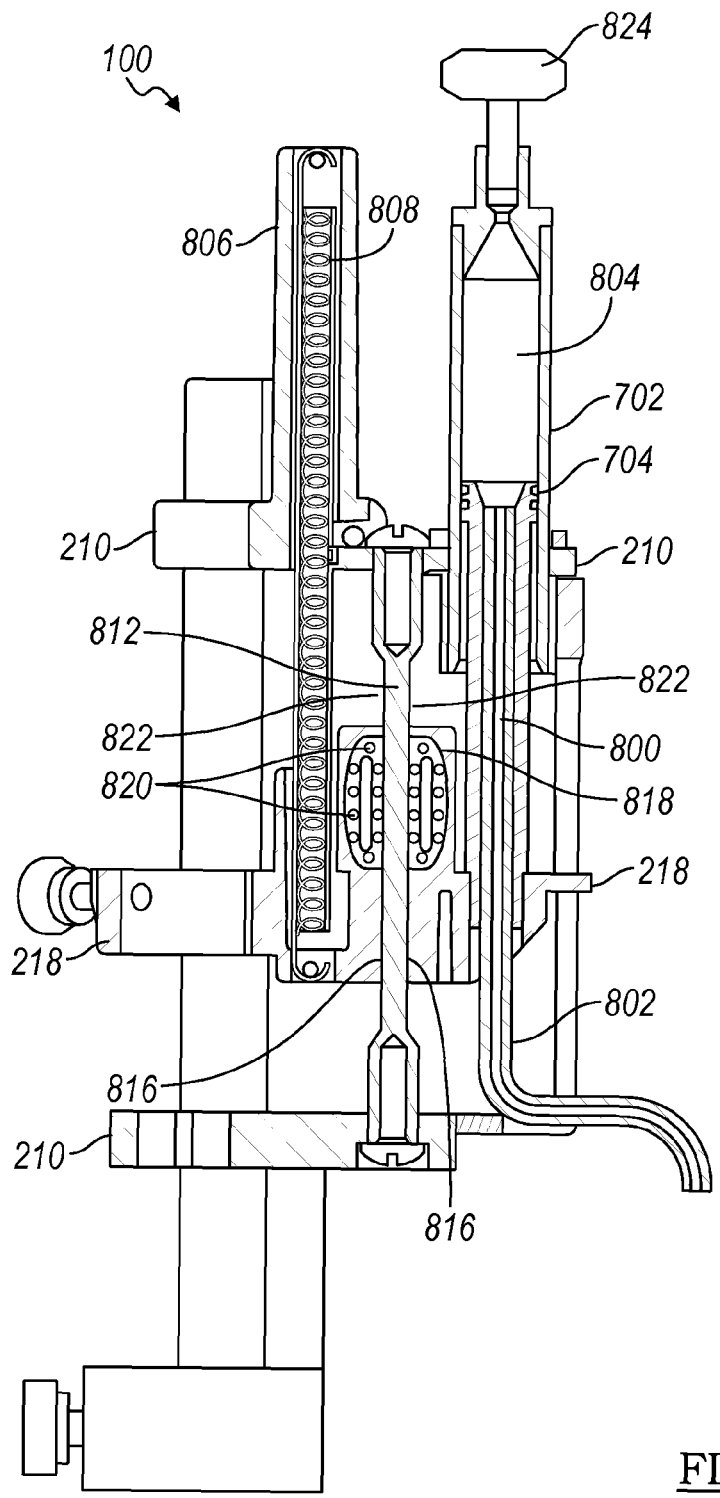
FIG. 8B is a sectional view of a further embodiment of the normalizing stage.

Another example of the normalizing stage 100 is shown in FIG. 8B. The second stage 218 includes at least one recirculating bearing 818 including ball bearings 820. The recirculating bearing 818 is at the interface 816 between the second stage 218 and guide rail 812 and thereby reduces friction first and second stages 210, 218. As shown in FIG. 8B, the recirculating bearing is a linear bearing to permit linear movement along the guide rail 812. In another example, the bearing 818 is a conventional non-circulating type. In yet another example, the recirculating bearing 818 is a flat bearing that rides along the guide rail 812. The guide rail 812 includes at least one groove 822 for receiving the balled bearings 820 of the flat recirculating bearing 818 to align the second stage 218 and thereby prevent undesired rotation of the second stage 218 around the guide rail 812. In still another example, the recirculating bearing 818 is a round bearing having a circular inner perimeter at the interface 816. Optionally, the second stage 218 includes a pair of round recirculating bearings 818 that ride on dual guide rails 812 to prevent undesired rotation of the second stage 218. The bearings 818 substantially reduce friction at the interface 816 thereby facilitating increased responsiveness of the second stage to actuation with the hydraulic actuator (e.g., the master hydraulic cylinder 706 and the master hydraulic piston 708).

In another example, a gas vent 824 is substituted for the valve 810. The gas vent 824 is coupled to the hydraulic cylinder 702 and in fluid communication thereto. When the hydraulic system 700 is filled (as described below) hydraulic fluid fills the volumes defined by the cylinders 702, 706, pistons 704, 708 and the hydraulic line 802. The air or other gas present in these spaces is forced out by introduction of the fluid. The valve 810 or gas vent 824 permits the gases to escape from the hydraulic system 700, but retains the hydraulic fluid therein. While gas permeable, the gas vent 824 is not liquid permeable. In one example, the gas vent 824 is a membrane comprised of polytetrafluoroethylene sold under the trademark TEFLON. In another example, any liquid impermeable membrane that otherwise is gas permeable is used as the gas vent 824.

Figure 8C:
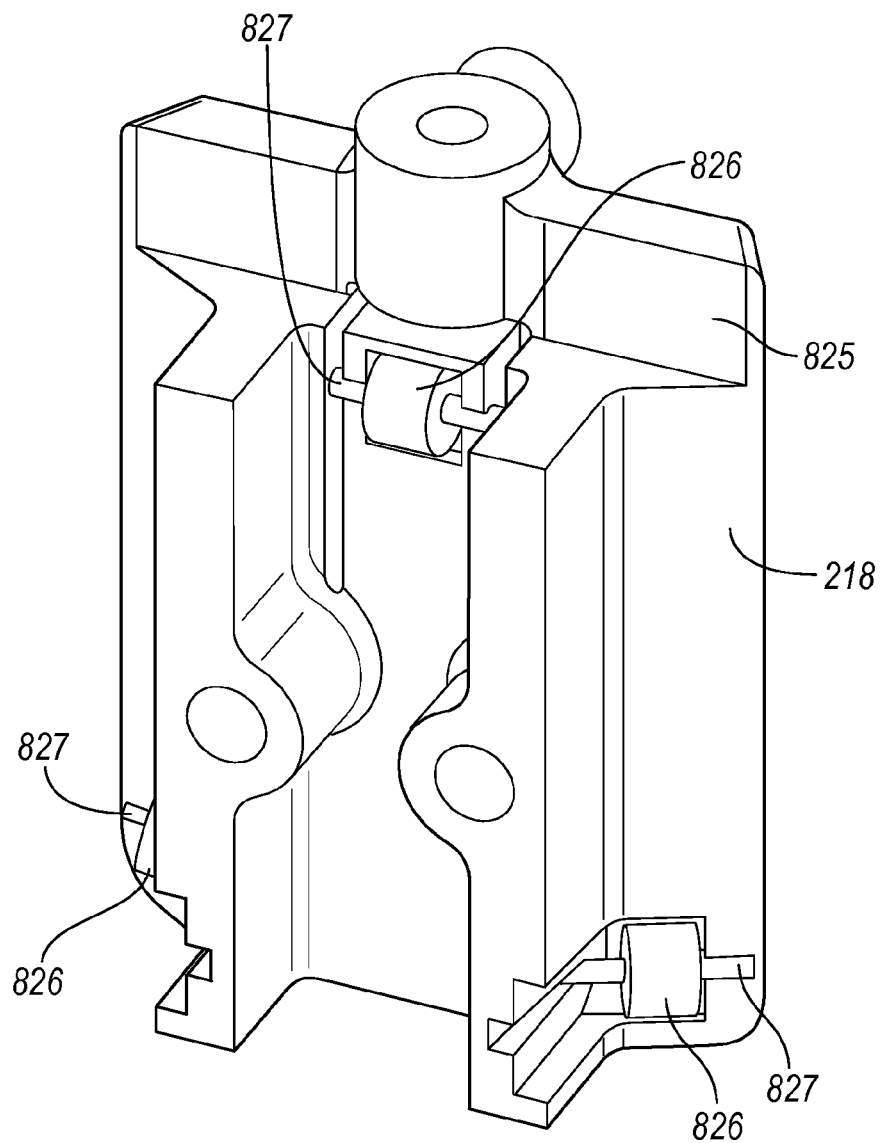
FIG. 8C is a perspective view of an embodiment of the first portion of a second stage.
Figure 8D:
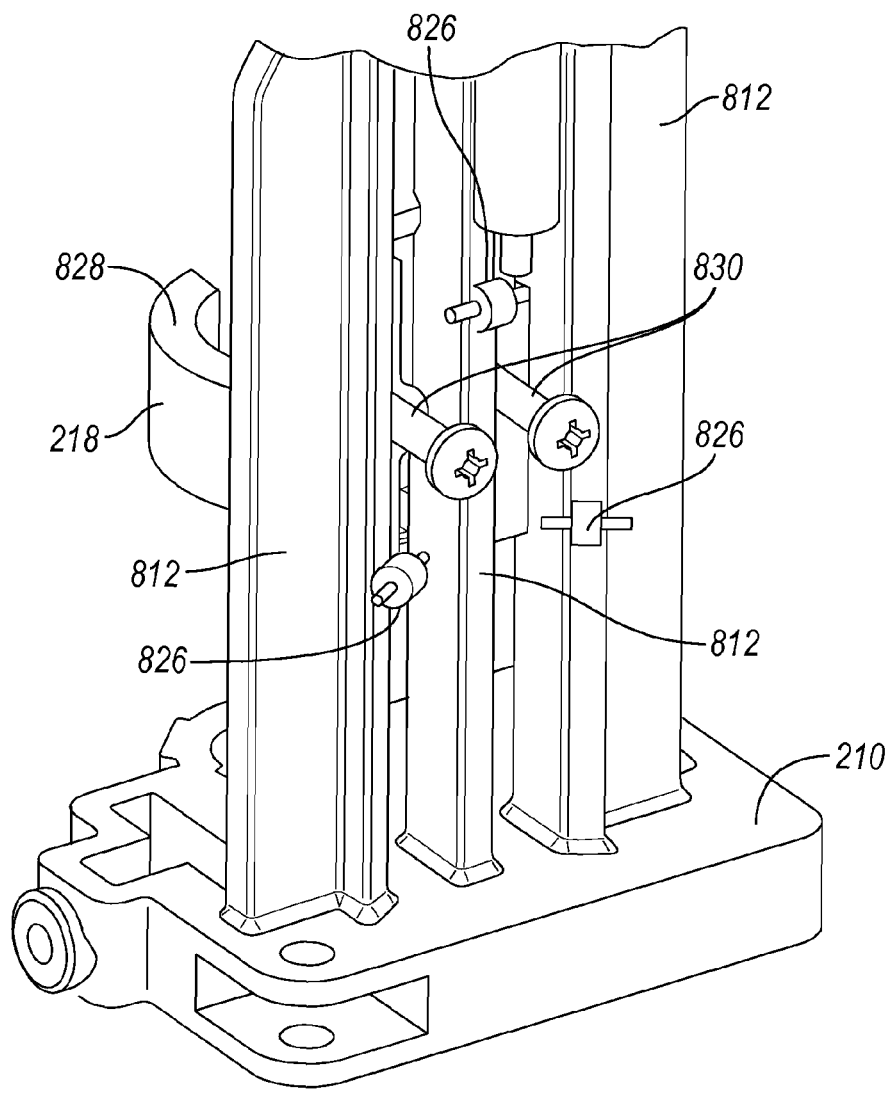
FIG. 8D is a perspective view of one example of a first stage and a second portion of the second stage of the normalizing stage.
Figure 8E:
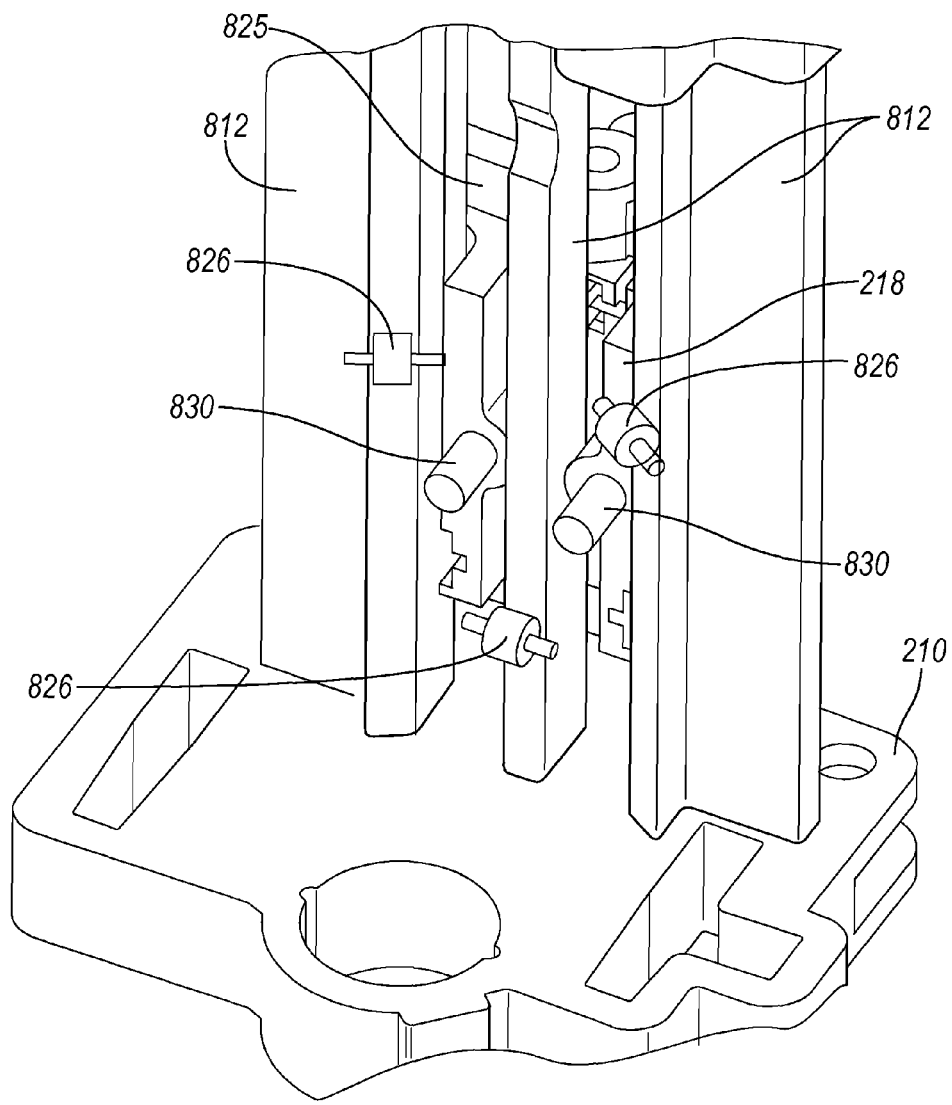
FIG. 8E is a perspective view of one example of the first stage and the first portion of the second stage of the normalizing stage.

FIGS. 8C-E illustrate another example of bearings coupled between the first stage 210 and the second stage 218. One example of a first portion 825 of the second stage 218 including three rollers 826 (e.g., needle rollers) is shown in FIG. 8C. In another example, the second stage 218 includes one or more rollers 826 (e.g., eight needle rollers). The rollers 826 are coupled to the first portion 825 with axles 827 that permit rotation of the rollers 826. The axles 827 have a small diameter to decrease bearing friction between the rollers 826 and the first portion 825. The first portion 825 of the second stage 218 shown in FIG. 8C is sized and shaped to couple along one side of the guide rails 812 (FIGS. 8D, E). Optionally, as shown in FIG. 8D, a second portion 828 of the second stage 218 having rollers 826 (FIG. 8E) is sized and shaped to couple along an opposed side of the guide rails 812 relative to the first portion 825. The first and second portions 825, 828 are coupled together, in one example, with fasteners 830 (FIG. 8D, E) such as screws, rivets, mechanical fittings and the like.

FIGS. 8C-E show one example of how the rollers 826 are arranged around the guide rails 812 to permit linear movement of the second stage 218 with substantially reduced friction. As shown in FIGS. 8D, E the guide rails 812 are sized and shaped to contact the rollers 826 of the first and second portion 825, 828 at angles intended to limit the movement of the second stage 218 to linear movement along the guide rails 812. The first and second portions 825, 828 of the second stage 218 are correspondingly sized and shaped to position the rollers 826 along the angled surfaces of the guide rails 812. Importantly, the arrangement of the rollers 826 allows linear movement of the second stage 218, but otherwise prevents unwanted rotation of the second stage 218 around the guide rails 812. In another example, the guide rails 812 and the first and second portions 825, 828 are sized and shaped in a variety of orientations that cooperate to permit linear movement of the second stage 218 without allowing rotation around the guide rails 812. For example, four rollers are positioned at angles relative to each other around a guide rail. Optionally, additional rollers are provided to enhance reduction of friction while allowing linear movement of the second stage 218 relative to the first stage 210.

Figure 9:
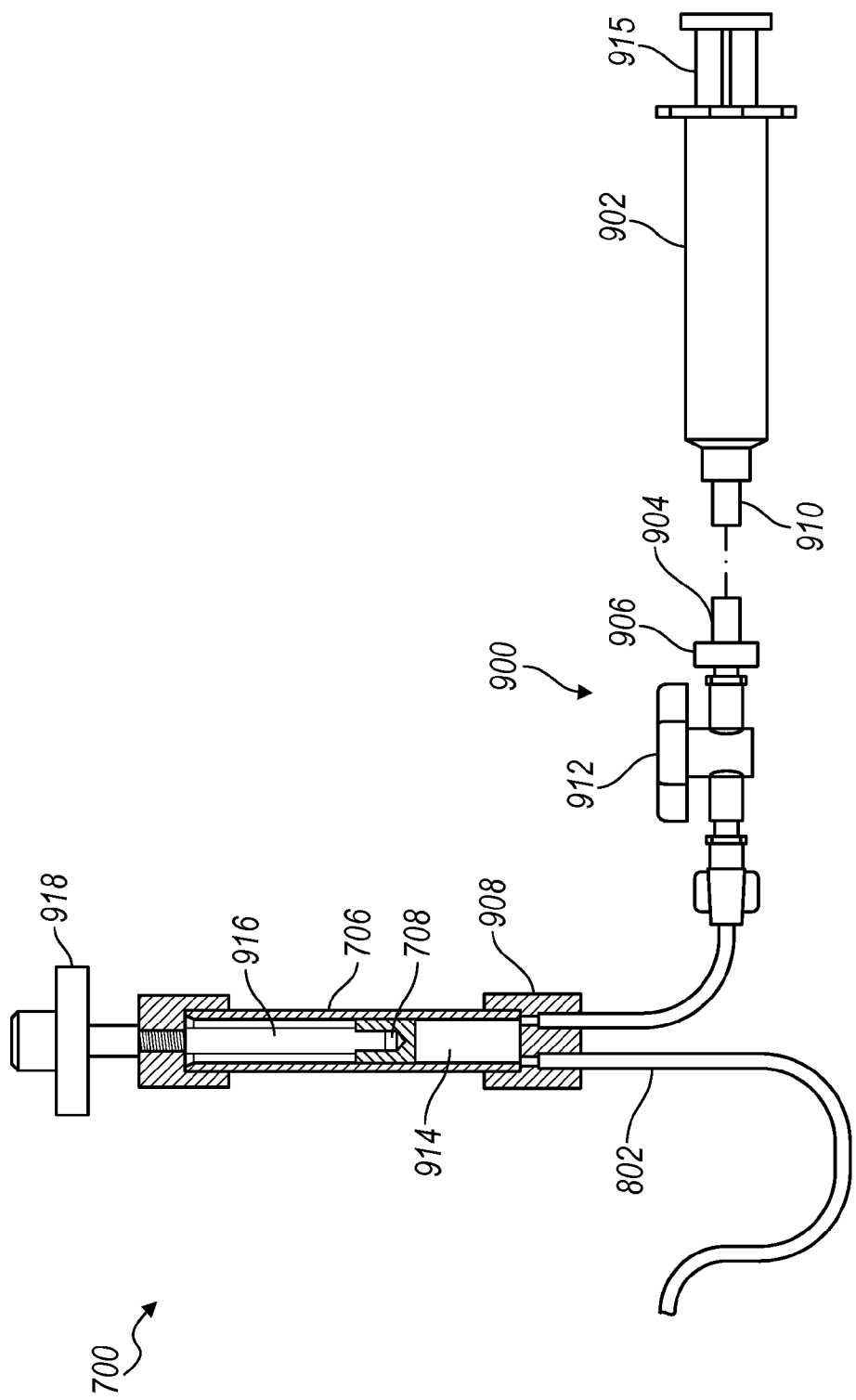
FIG. 9 is a side view illustrating the fluid inlet and syringe used to fill the hydraulic system, as well as the master cylinder and master piston.

FIG. 9 is a side view illustrating a fluid inlet 900 and syringe 902 used to fill the hydraulic system 700. In this example, the fluid inlet 900 is coupled to the master hydraulic cylinder 706 and is in fluid communication thereto through a manifold 908 that includes a portion of the hydraulic line 802, which is also in fluid communication with the master hydraulic cylinder 706. In another example, the fluid inlet 900 is in direct fluid communication with the master hydraulic cylinder 706. The fluid inlet 900 includes a socket 904 and check valve 906. The check valve 906 prevents fluid introduced at the inlet 900 from leaking out at the inlet 900. In the example shown in FIG. 9, a stopcock 912 is coupled to the check valve 906 and in fluid communication thereto. The syringe 902 includes a nozzle 910 dimensioned and configured to snugly couple with the socket 904 of the fluid inlet 900. The syringe 902 is filled with a hydraulic fluid (for example, sterile saline) and the nozzle 910 is inserted into and coupled to the socket 904. The plunger 915 of the syringe 902 is then depressed. This forces the hydraulic fluid from the syringe 902 into the fluid inlet 900 and hydraulic system 700. In one example, the syringe 902 injects enough hydraulic fluid into the system 700 to fill the volume defined by the cylinders 702, 706, pistons 704, 708, and hydraulic line 802 and allow a full range of movement for the second stage 218. In another example, the syringe 902 is filled and used multiple times to fully fill the hydraulic system 700.

The master hydraulic cylinder 706 and master hydraulic piston 708 are shown in FIG. 9. As described above, the master hydraulic piston 708 is coupled to the master hydraulic cylinder 706 to allow slidable movement therebetween. The inner surface of the master cylinder 706 and the master piston 708 define a second volume 914. The second volume is increased and decreased by actuation of a screw 916, a distal end of which is coupled to the master piston 708 and the master cylinder 706. The threaded outer surface of the screw 916 engages a correspondingly threaded inner surface of the master cylinder 706. Rotation of the screw 916 advances the screw, and thus the master piston 708, with respect to the master cylinder 706. A knob 918 is coupled to a proximal end of the screw 916 to enable rotation of the screw. Changing the second volume 914 correspondingly changes the first volume 804 in a substantially inverse manner by moving hydraulic fluid through the hydraulic line 802. In other words, decreasing the second volume 914 similarly increases the first volume 804, and increasing the second volume decreases the first volume in substantially the same way. The screw 916 thus operates to move the second stage 218 through actuation of the master cylinder 706, master piston 708, hydraulic cylinder 702, and hydraulic piston 704.

Figure 10A:
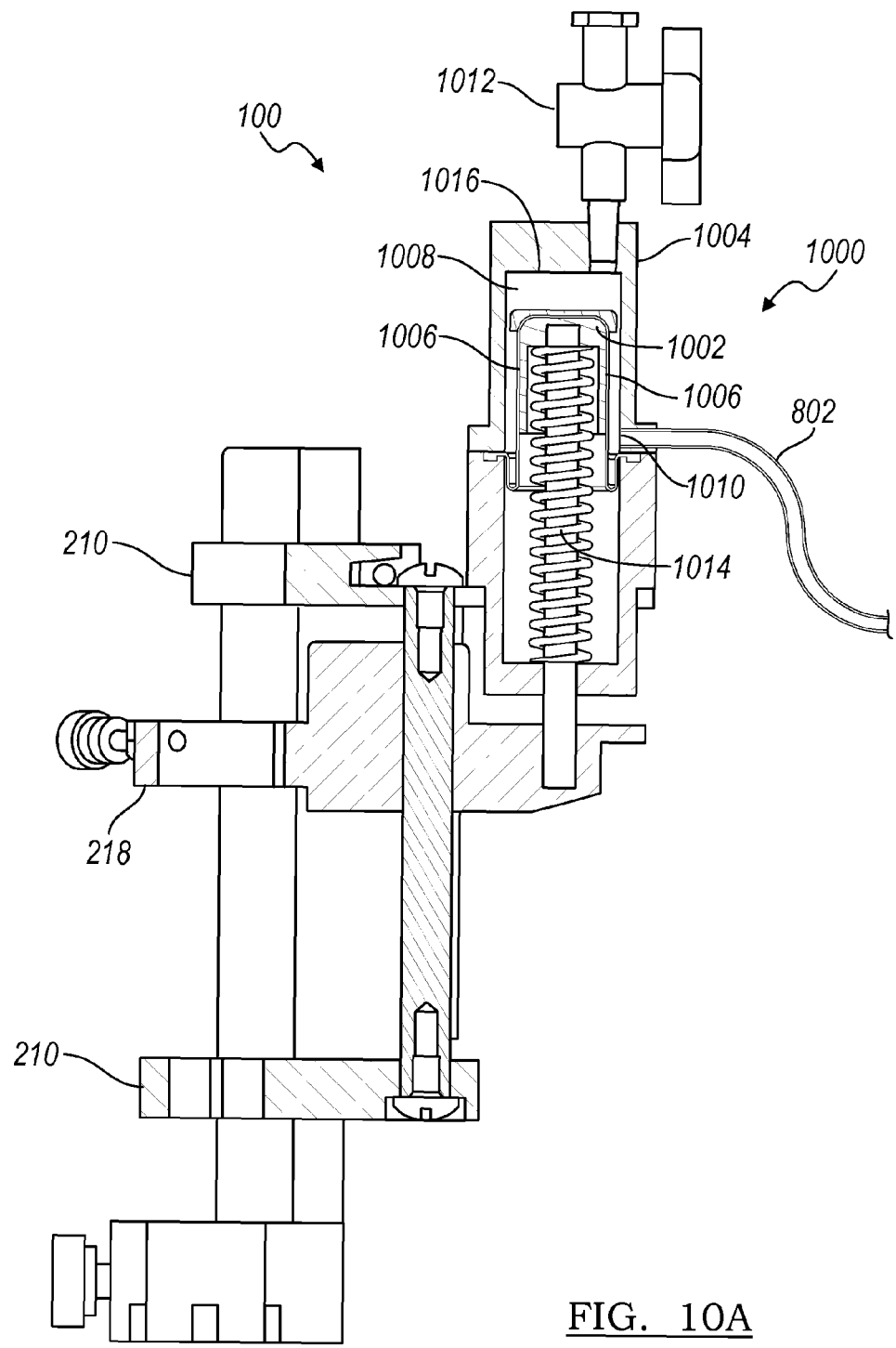
FIG. 10A is a sectional view illustrating an embodiment of a normalizing stage having another hydraulic system.

FIG. 10A is a sectional view of another embodiment of normalizing stage 100 including a rolling diaphragm hydraulic system 1000. In this example, hydraulic system 1000 includes a piston 1002 disposed within a cylinder 1004. In one example, a flexible fluid impermeable membrane 1006 extends from a surface defining the circumference of piston 1002. The membrane 1006 is coupled to the cylinder 1004. The membrane 1006, piston 1002, and cylinder 1004 define a first volume 1008. The first volume 1008 is changed by actuation of the master piston 708 and master cylinder 706 via screw 916 (described above). The flexible membrane 1006 provides a seal between the cylinder 1004 and piston 1002 while one piece moves with respect to the other. In an example, there is sufficient clearance between the cylinder 1004 and piston 1002 for the flexible membrane to fold between the cylinder and piston. In other words, the cylinder 1004 and piston 1002 move without directly contacting one another. Expanding and contracting the first volume 1008 thereby produces substantially little friction between cylinder 1004 and piston 1002. Thus, more accurate and responsive movement of the piston 1002 with respect to the cylinder 1004 is possible.

In one example, a spring 1014 or the like is disposed between piston 1002 and cylinder 1004. The spring 1014 is optionally in compression and maintains a force on the piston 1002 relative to the cylinder 1004. The spring 1014 pushes piston 1002 and, with it, second stage 218 toward the fluid filled end of the cylinder 1004. The incompressibility of hydraulic fluid in the cylinder 1002 prevents the spring 1014 from undesirably moving the second stage 218. The spring 1014 thus maintains a pressurized hydraulic system 1000 by pushing the piston 1002 toward the cylinder 1004.

Figure 10B:
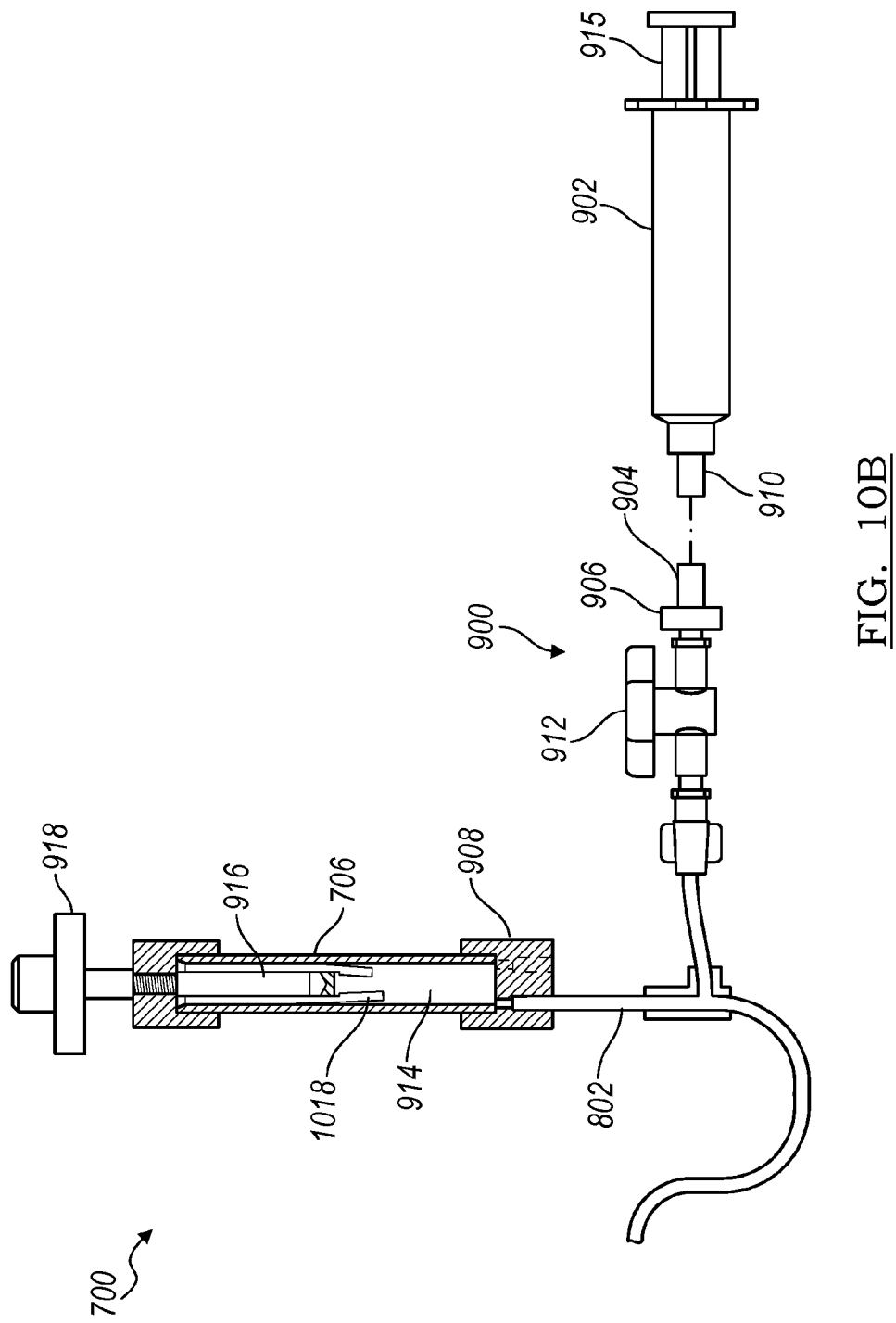

Referring now FIG. 10B, in another example, a flexible liquid impermeable membrane 1018 for a rolling diaphragm extends between the master hydraulic cylinder 706 and master hydraulic piston 708. The master hydraulic piston 708 is coupled to master hydraulic cylinder 706 with a rolling diaphragm similarly to how piston 1002 and cylinder 1004 are coupled in FIG. 10. The rolling diaphragm provided with the flexible membrane 1018 facilitates enhanced movement of the piston 708 relative to the cylinder 706 by reducing friction therebetween. Additionally, the reduced friction provided by the flexible membrane 1018 improves responsiveness between rotation of the knob 918 and movement of the piston 708 thereby enhancing overall responsiveness at the piston 1002 and the cylinder 1004 of the normalizing stage 100 (FIG. 10).

In yet another example shown in FIG. 10B, the syringe 902 and stopcock 912 couple to hydraulic line 802 between hydraulic system 1000 and the master hydraulic system 700. Coupling the fluid inlet 900 provided by the syringe 902 and the stopcock 912 along the line 802 eliminates the need for the manifold 908 (FIG. 9). Additionally, the fluid inlet 900 is in closer communication with the hydraulic system 1000 facilitating easier filling of the system 1000.

An inlet 1010 to the first volume 1008 is provided through the cylinder 1004. The inlet 1010 and the first volume 1008 are in fluid communication with the hydraulic line 802. A stopcock valve 1012 is coupled to the cylinder 1004 and is operable to open or seal the system 1000 for hydraulic fluid filling.

As described in a previous example, a gas vent can be substituted for stopcock valve 1012 in FIG. 10. In this example, as before, air or other gas in first volume 1008 escapes through the gas permeable membrane of the vent. In one example, end surface 1016 of cylinder 1004 is replaced with a suitably-supported gas permeable membrane. Because hydraulic system 1000 is under pressure relative to the surrounding atmosphere (e.g., due to spring 1014), gas or air bubbles are forced out of the hydraulic fluid when they contact the surface of the membrane. The large surface area and direct path at the end surface 1016 facilitate the escape of gas or air from within the hydraulic system 1000. In this way, hydraulic system 1000 easily fills completely with incompressible hydraulic fluid (e.g., sterile saline). In another example, both hydraulic system 1000 and the master hydraulic system 700 include gas vents as just described.

The position of the second stage 218 relative to the first stage 210, in one example including the hydraulic systems 700, 1000, is measured with a potentiometer, such as potentiometer assembly 600 (described above). The potentiometer assembly 600 provides accurate and precise indications of the second stage 218 position with respect to the first stage 210. In another example, the potentiometer assembly 600 indicates the position of an instrument with respect to the desired target (as described above). The potentiometer assembly 600 allows for direct measurement of movement of the second stage 218 relative to the first stage 210. The potentiometer assembly 600 overcomes measurement error due to lag or hysteresis caused by deformability of the materials used in the hydraulic systems 700, 1000. Measurement error typically appears when measuring the position of the hydraulic pistons 704, 1002 relative to the hydraulic cylinders 702, 1002 by translation of the master piston 708 relative to the master cylinder 706. The potentiometer assembly 600 also overcomes measurement error caused by friction in the hydraulic systems 700, 1000, for instance between the hydraulic cylinders 702, 706, 1004 and hydraulic pistons 704, 708, 1002. Measurement error is overcome by directly measuring the translation of the second stage 218 relative to the first stage 210 with the potentiometer assembly 600.

FIG. 11A is an exploded view of a portion of the fixture assembly 102. An instrument immobilizer 1100 is coupled to the surface of a skull 1102 around a burr hole in the skull 1102. In this example, the instrument immobilizer 1100 is coupled to the surface of the skull 1102 by bone screws extending through the immobilizer and into the skull. The immobilizer 1100 further includes a retaining piece 1106. The retaining piece 1106 is operable to engage and immobilize a portion of an instrument (described below). Additional examples of instrument immobilizers are shown in PCT Patent Application No. PCT/US03/28966 filed on Sep. 17, 2003, which is assigned to the assignee of the present patent application, and which is incorporated by reference herein in its entirety.

Additionally, in this example, a saddle assembly 1104 is coupled to the instrument immobilizer 1100 and aligned with an orthogonal 1134 axis through a center of the instrument immobilizer 1100. Specifically, a base ring 1108 is coupled to the instrument immobilizer 1100. In one example, the saddle assembly 1104 is initially aligned with the orthogonal axis 1134, but coupled to the skull surface 1102. The orthogonal axis 1134 is substantially orthogonal to the surface of the skull 1102. The saddle assembly 1104 further includes a cylindrical sectional tower base 1110 that is dimensioned and configured to couple with the base ring 1108 to allow rotation therebetween. A saddle slide 1112 is coupled to the tower base 1110. Thumbscrews 1114 or the like extend through slots 1116 of the saddle slide 1112 and the tower base 1110. The thumbscrews 1114 engage blocks 1118 disposed adjacent to the base ring 1108. The blocks 1118 engage a lip of the base ring 1108. The saddle slide 1112 is operable to move in an arcuate motion with respect to the tower base 1110. In other words, the saddle slide 1112 rotates by rotating the tower base 1110 with respect to the base ring 1108 and sweeps an arc by moving the saddle slide 1112 with respect to the tower base 1110. The saddle slide 1112 and the tower base 1110 are fixed in place by tightening of the thumbscrews 1114, which pulls the blocks 1118 against the base ring 1108, the base ring 1108 is pulled against the tower base 1110, and the tower base is pulled against the saddle slide.

The saddle assembly 1104 also includes a guide lumen 1120 having a saddle trajectory that passes through the base ring 1108 and the instrument immobilizer 1100. The guide lumen 1120 is dimensioned and configured to interchangeably retain alignment guides and instrument guides (described below). A thumbscrew 1122 or other fixation device extends through a wall of a cylindrical portion of the saddle slide 1112 that defines the guide lumen 1120. The thumbscrew 1122 is operable to engage and retain an alignment guide or instrument guide having a portion disposed within the guide lumen 1120. The saddle slide 1112 is positionable to orient the saddle trajectory in various orientations available with the above described arcuate and rotational movement. One example of the saddle assembly 1104 is further described in U.S. patent application Ser. No. 10/671,913, filed on Sep. 25, 2003, which is assigned to the assignee of the present application and which is incorporated by reference herein in its entirety. Additional examples of saddles are shown in U.S. patent application Ser. No. 09/828,451, filed on Apr. 6, 2001, which is assigned to the assignee of the present patent application, and which is incorporated by reference herein in its entirety.

FIG. 11A also illustrates an alignment ring 1136 including tabs 1138. The tabs 1138 are sized and shaped to engage with a rack 1140 including, for instance teeth 1142. The teeth 1142, in one example, are spaced around the rack 1140 at 4 degree intervals. The tabs 1138 deform with rotation of the alignment ring 1136 relative to the rack 1140 and snap into the grooves between the teeth 1142 to provide a clicking detent. The alignment ring 1136, in another example, is thus incrementally positionable around the rack 1140.

The alignment ring 1136 is sized and shaped to fit around the wall of the upwardly protruding cylindrical portion of the saddle slide 1112 that defines the guide lumen 1120. Clamps 1144 extend from the alignment ring 1136, in another example. The rack 1140 projects radially, in yet another example, from the cylindrical portion of the saddle slide 1112 and defines a lip. The clamps 1144 are sized and shaped to engage with the lip and secure the alignment ring 1136 to the saddle slide 1112 with inwardly extending hooks 1146, for example. The clamps 1144 deform as the hooks 1146 are pressed over the rack 1140. The clamps 1144 assume the undeformed shape when the alignment ring 1136 is pressed onto the rack 1140 and hooks 1146 disengage from the rack 1140 and engage against the lip to secure the alignment ring 1136 to the saddle slide 1112. An inner surface of the alignment ring 1136 defines grooves 1132 dimensioned and configured to receive keyed teeth from an alignment guide or instrument guide (both described below). In one example, the grooves 1132 are positioned every 45 degrees about the inner surface of the alignment ring 1136.

FIG. 11B illustrates another example of an alignment ring 1124 includes two semi-circular portions 1126. Each semi-circular portion 1126 is dimensioned and configured to fit around the wall of the upwardly protruding cylindrical portion of the saddle slide 1112 that defines the guide lumen 1120. This wall includes an inward turned lip dimensioned and configured to engage a groove present in each semicircular portion 1126. In one example, the lip and grooves have cooperatively engaged teeth, spaced approximately every 6 degrees of the 360 degree cylindrical wall. The semicircular portions 1126 are coupled to one another, such as with elastic bands 1128. The ends of the semicircular portions 1126 have pinching surfaces 1130 that extend from the semicircular portions 1126. Each pair of pinching surfaces 1130 is near one of the elastic bands 1128 on opposing sides of the elastic band 1128. Pressure applied to opposed pinching surfaces 1130 stretches the elastic band 1128 and separates the semi-circular portions 1126. In this way the pinching surfaces 1130 are operable to spread the semicircular portions 1126 apart and allow rotational movement of the alignment ring 1124 with respect to the saddle slide 1112. An inner surface of the alignment ring 1124 defines grooves 1132 dimensioned and configured to receive keyed teeth from an alignment guide or instrument guide (both described below). In one example, the grooves 1132 are positioned every 45 degrees about the inner surface of the alignment ring 1124.

FIG. 12 shows an exploded view of the fixture assembly 102 including the saddle assembly 1104, alignment ring 1136, a centered alignment guide 1200, and an orienting fixture 1202. The centered alignment guide 1200 includes a base 1204 and an alignment pin 1206 coupled to the base. In this example, the alignment pin 1206 is centrally aligned with the base 1204 such that when the centered alignment guide 1200 is inserted into the lumen 1120 of the saddle assembly 1104, the pin 1206 is centered within the lumen 1120 to define the saddle trajectory. The centered alignment guide 1200 is immobilized within the lumen 1120 by thumbscrew 1122 or the like. In one example, the centered alignment guide 1200 includes keyed teeth 1208. The keyed teeth 1208 are dimensioned and configured to cooperatively engage the surfaces defining the grooves 1132 of the alignment ring 1136. This prevents undesired rotation between the saddle assembly 1104 and the centered alignment guide 1200. In one example, the keyed teeth 1208 are disposed around the circumference of the centered alignment guide 1200 at approximately 45 degree intervals. In one example, the centered alignment guide 1200 includes a flange 1210 that partially or completely circles a circumferential portion of the alignment guide 1200. The flange 1210 engages the upper surface of the cylindrical wall of the saddle slide 1112 that defines the guide lumen 1120. As a result, only the base 1204 is within the guide lumen 1120 when the centered alignment guide 1200 is coupled to the saddle assembly 1104.

The orienting fixture 1202 is coupled to the alignment pin 1206. In one example, a thumbscrew 1212 or other fixation device extends through a portion of the centered alignment guide base 1204 toward the alignment pin 1206. The thumbscrew 1212 is operable to engage and retain the orienting fixture 1202 against the alignment pin 1206. In one example, the orienting fixture 1202 is remotely detectable such as by remote positioning systems using infrared (IR) light detection. Such detection uses a number of detectable objects on the orienting fixture 1202. Examples of such objects include reflective structures or light emitting diodes (LED's) included on the orienting fixture 1202. In another embodiment, the remote detection of the detectable objects uses a tissue imaging method. Suitable tissue imaging methods include, but are not limited to: magnetic resonance imaging (MRI); computed tomography (CT); ultrasound imaging; etc. In one example, the orienting fixture 1202 is used to locate and display the saddle trajectory on an image-guided surgical (IGS) computer workstation. In another example, the orienting fixture 1202 is used to compute the distance to a target in the brain from the orienting fixture. One suitable orienting fixture 1202 is the StealthFighter™, manufactured by Medtronic Inc. of Minneapolis, Minn.

In another example, the flange 1210 of alignment guide 1200 includes an alignment window 1214. The alignment window 1214, in one example, is a notch, opening or the like in the flange 1210. The alignment ring 1136 includes markings 1216, for instance alpha-numerical markings. Through cooperative engagement of the keyed teeth 1208 with the grooves 1132 (described above) the alignment window 1214 of the alignment guide 1200 reveals at least one marking 1216. The keyed teeth 1208, grooves 1132, alignment window 1214, and the markings 1216 are used cooperatively to position the alignment guide 1200, and thus the orienting fixture 1202, in a desired orientation within the guide lumen 1120. The markings 1216 are positioned around the alignment ring 1136 to correspond, in one example, to the 45 degree increments between the keyed teeth 1208. In another example, an offset alignment guide 1300 (described below) includes an alignment window 1214 similar to that of centered alignment guide 1200. The alignment window 1214 and markings 1216 allow for accurate orientation of instrument lumens within an instrument guide (described below).

FIG. 13 is an exploded view of the fixture assembly 102 including the saddle assembly 1104, alignment ring 1136, an offset alignment guide 1300, and an orienting fixture 1202. The offset alignment guide 1300 is similar to the centered alignment guide 1200 described above, except that its alignment pin 1306 is offset from its central axis. The alignment pin 1306 is parallel to the central axis of the cylindrical base 1204 but offset therefrom. When the offset alignment guide 1300 is coupled to the saddle assembly 1104, the pin 1306 defines a saddle trajectory offset from the center of the guide lumen 1120. Multiple combinations of saddle trajectories are available with adjustments of the alignment ring 1136 and/or the offset alignment guide 1300. In one example, the offset alignment guide 1300 is repositioned within the alignment ring 1136 with teeth 1208 at 45 degree increments around the 360 degree circle defined by the alignment ring 1136. In another example, the alignment ring 1136 is rotated according to cooperatively engaged teeth (described above) incrementally spaced every 4 degrees and disposed within the inner groove of the alignment ring 1136 and lip of the saddle slide 1112. In yet another example, the offset alignment guide 1300 is adjusted according to the teeth 1208 spaced every 45 degrees as well as the cooperatively engaged teeth between the alignment ring 1136 and the saddle slide 1112 to achieve additional saddle trajectories.

In another example, the flange 1210 of alignment guide 1300 includes an alignment window 1214 as described above regarding alignment guide 1200. The alignment ring 1136 includes markings, for instance alpha-numerical markings 1216. The keyed teeth 1208, grooves 1132, alignment window 1214, and the markings 1216 are used cooperatively to position the alignment guide 1300 in a desired orientation within the guide lumen 1120.

FIG. 14 is a partial sectional and exploded view of the fixture assembly 102 including the saddle assembly 1104, alignment ring 1136, and a centered instrument guide 1400. In this example, the centered instrument guide 1400 includes a first portion 1402 and a second portion 1404. The second portion 1404 is coupled to the saddle assembly 1104 and immobilized by thumbscrew 1122. Like the alignment guides 1200 and 1300, the centered instrument guide 1400 includes keyed teeth 1406 dimensioned and configured to cooperatively engage the surfaces defining the grooves 1132 of the alignment ring 1136. Relative rotation between the centered instrument guide 1400 and the saddle assembly 1104 is prohibited by the relationship of the keyed teeth 1406 to the surfaces defining the grooves 1132 and by the tabs 1138 on the alignment ring 1136 that engage corresponding teeth 1142 around the guide lumen 1120. In one example, a flange 1408 is disposed substantially between the first portion 1402 and second portion 1404. In another example, the flange 1408 is included in the first portion 1402 or second portion 1404. The flange 1408 extends from and surrounds all or a portion of the centered instrument guide 1400. The flange 1408 engages the upper surface of the alignment ring 1136 so only the second portion 1404 is within the guide lumen when the centered instrument guide 1400 is coupled to the saddle assembly 1104.

In this example, a multilumen insert 1412 is disposed within a passage 1414 defined by an inner surface of the centered instrument guide 1400. The multilumen insert 1412 is dimensioned and configured to snugly couple with the inner surface. Instrument lumens 1416 are arranged in a pattern within the insert 1412. In this example, a central lumen 1416 extends substantially through the insert 1412 along a central axis of the insert 1412. Four additional instrument lumens 1416 are disposed around the central lumen 1416 at 90 degree intervals. In another example, the instrument lumens 1416 are disposed in a different configuration within the insert 1412, for example, in a pentagonal pattern or a three by three matrix of lumens 1416. Each instrument lumen 1416 is dimensioned and configured to slidably couple with a guide tube (described below) while constraining lateral movement of the guide tube. In one example, the instrument lumens 1416 are defined by a single inner surface of the multi lumen insert 1412. In other words, the lumens 1416 are furrows interconnected within the insert 1412. In another example, the instrument lumens 1416 are separate and distinct lumens extending through the insert 1412.

The first portion 1402 of centered instrument guide 1400 includes proximally accessible keyed teeth 1418. The keyed teeth 1418 are disposed around the centered instrument guide 1400. In one example, the keyed teeth 1418 are disposed at 90 degree intervals around the guide 1400. In this example, the keyed teeth 1418 and the first portion 1402 are dimensioned and configured to couple with the normalizing stage apparatus 100. The keyed teeth 1418 engage with corresponding slots 500 (See FIG. 5) on the normalizing stage base 200 to prohibit undesirable relative rotation between the normalizing stage apparatus 100 and the centered instrument guide 1400. The offset instrument guide (described below) also includes keyed teeth dimensioned and configured to couple with the normalizing stage base 200 and prohibit undesirable rotation between the normalizing stage apparatus 100 and the offset instrument guide.

In one example, the instrument guide 1400 includes at least one alignment window 1420 within the flange 1408. The alignment window 1420 is sized and shaped to reveal markings 1216 on the alignment ring 1136 when the instrument guide 1400 is coupled to the alignment ring 1136. In one example, the instrument guide 1400 is positioned on the alignment ring 1136 so the alignment window 1420 reveals the same marking 1216 determined with the alignment guide 1200. The keyed teeth 1406 are disposed within the grooves 1132 of the alignment ring 1136 to orient the instrument guide 1400 on the alignment ring 1136. The instrument lumens 1416 are oriented in the instrument guide 1400 so matching of the marking 1216 exposed in the alignment window 1214 (alignment guide) to the marking 1216 exposed in the alignment window 1420 (instrument guide) positions the instrument lumens 1416 in the desired orientation. The orienting fixture 1202 is used to obtain the desired orientation of the instrument guide 1400 including the instrument lumens 1416. As a result, if the markings 1216 exposed in the alignment window 1420 are the same as those in alignment window 1214 the instrument lumens 1416 are in the desired orientation.

In another example, the instrument guide 1400 includes a skirt 1422. The skirt 1422 extends downwardly with respect to the flange 1408 and is sized and shaped to snugly coupled around the alignment ring 1136. Coupling of the skirt 1422 around the alignment ring 1136 substantially prevents rotation of the alignment ring 1132 because the skirt 1422 pins the tabs 1138 against the rack 1140. As a result, the tabs 1138 are unable to deform and move around the teeth 1142. The skirt 1422 secures the instrument guide 1400 in a desired orientation determined, for example with the markings 1216 and the alignment window 1420 (described above).

FIG. 15 is a partial sectional and exploded view of the fixture assembly 102 including the saddle assembly 1104, alignment ring 1136, and an offset instrument guide 1500. The offset instrument guide 1500 is similar to the centered instrument guide 1400. In this example, the offset instrument guide 1500 includes a first portion 1502 and a second portion 1504. In a similar manner to the offset alignment guide 1300, the offset instrument guide 1500 is positionable to define multiple trajectories. The offset instrument guide 1500 is adjusted with positioning of the guide 1500 within the alignment ring 1136 to engage teeth 1406 with grooves 1132 and positioning of the alignment ring 1136 using tabs 1138 and corresponding teeth 1142 on the rack 1140 of the saddle slide 1112.

FIG. 16A shows an exploded view of the normalizing stage apparatus 100, a guide tube stop 1600, a guide tube 1602, and an obturator 1604. The guide tube stop 1600 is dimensioned and configured so its cylindrical outer surface fits snugly in the cylindrical inner surface that defines the guide tube stop lumen 216. In this example, a guide tube stop flange 1606 on the guide tube stop 1600 engages an upper lip of a surface that defines the lumen 216 of the first stage 210. In one example, guide tube lumens 1608 are arranged in a pattern within the guide tube stop 1600. In this example, a central lumen 1608 extends through the guide tube stop 1600 along a central axis of the guide tube stop 1600. Four additional guide tube lumens 1608 are disposed around the central lumen 1608 at 90 degree intervals. In another example, the guide tube lumens 1608 are disposed in a different configuration through the guide tube stop 1600, for example, in a pentagonal pattern or a three by three matrix of lumens 1608. In yet another example, the guide tube stop 1600 includes an outer ring having the flange 1606 and an insert dimensioned and configured to fit therein. The insert includes a pattern of guide tube lumens 1608. Different patterns of lumens 1608 are available in different inserts, which may be packaged together (and with any other components such as the normalizing stage) and sold as a kit. The instrument lumens 1608 are dimensioned and configured to slidably couple with the guide tube 1602 while constraining lateral movement of the guide tube 1602. In one example, the guide tube stop lumen 216 is keyed to the guide tube stop 1600. Such keying permits alignment of the pattern of lumens 1608 with the pattern of instrument lumens 1416 of the multi lumen insert 1412.

The guide tube 1602 snugly slides into one of the lumens 1608 of the guide tube stop 1600. In this example, a guide tube flange 1610 is substantially adjacent a proximal end of the guide tube 1602, and extends partially or completely around the guide tube 1602. The flange 1610 engages the upper surface of the guide tube stop 1600 when the guide tube 1602 is plunged through the guide tube stop 1600. This prevents the guide tube 1602 from sliding through the guide tube stop 1600. In this example, the guide tube 1602 is of a predetermined length, such that a physician or technician could use an "off the shelf" guide tube for a procedure with the normalizing stage with any patient. The guide tube distal end 1612 is plunged until the flange 1610 engages the guide tube stop 1600, in one example. When the first stage 210 is positioned at the proper distance to target and the flange 1610 has engaged the guide tube stop 1600, the distal end 1612 is substantially adjacent to the desired target. In one example, the distal end 1612 is then offset by a desired known distance from the target, for example 15 millimeters. In another example, the distal end 1612 is offset from the target a smaller increment according to the desires of the physician.

When initially plunging the guide tube 1602 the obturator 1604 is included within the guide tube. The obturator 1604 has an outer surface dimensioned and configured to slidably couple with the inner surface of the guide tube 1602. In this example, the obturator 1604 has a length substantially similar to the guide tube 1602. The distal ends of the obturator 1604 and guide tube 1602 define a blunt distal surface that prevents coring of the brain or other tissue. Near a proximal end of the obturator 1604 is an obturator flange 1616 that extends partially or completely around its circumference. The flange 1616 engages the upper surface of the guide tube 1602 when the obturator 1604 is within the guide tube. This prevents the obturator 1604 from sliding through the guide tube 1602.

FIG. 16B is an exploded view of one example of a guide tube stop 1620. The guide tube stop 1620 includes an outer ring 1622 sized and shaped so its cylindrical outer surface fits snugly in the cylindrical inner surface that defines the guide tube stop lumen 216 (FIGS. 2 and 16A). As described above for guide tube stop 1600, the outer ring 1622 of the guide tube stop 1620 includes a flange 1606 radially extending from the outer ring 1622. The flange 1606 engages an upper lip of a surface that defines the lumen 216 of the first stage 210. An inner surface 1624 of the outer ring 1622 defines at least two grooves 1626 sized and shaped to slidably couple with the guide tube 1602 (FIG. 16B).

The guide tube stop 1620 includes a rocker 1628 sized and shaped to fit within the outer ring 1622. The rocker 1628 includes at least two grooves 1630 sized and shaped to slidably couple with the guide tube 1602. The rocker 1628 further includes, in one example a projection 1632 extending toward the grooves 1626 of the outer ring 1622. The projection 1632 is operable to engage against the inner surface 1624 of the outer ring 1622 in one example. In another example, the projection 1632 engages against the guide tube 1602 disposed between the rocker 1628 and the inner surface 1624 to substantially immobilize the guide tube 1602. The rocker 1628 includes, optionally, a stud 1634. The stud 1634, in one example, is sized and shaped to extend at least partially through a notch 1636 in the outer ring 1622. The stud 1634 is engaged by a thumbscrew 1638 (FIGS. 16A, 16B) that extends through a portion of the first stage 210 and into the lumen 216. The thumbscrew 1638 is operable to move the rocker 1628 by engaging the stud 1634. The rocker, in one example, moves toward the grooves 1626 of the outer ring 1622 and/or rotates around the stud 1634 so the projection 1632 engages against the outer ring inner surface 1624 or the guide tube 1602.

In another example, the guide tube stop 1620 includes a seat 1640 sized and shaped to fit between the inner surface 1624 including the grooves 1626 and the surface of the rocker 1628 that defines the grooves 1630. In one example, the seat 1640 includes legs 1642 sized and shaped to extend through the outer ring 1622. The legs 1642 include detents 1644 substantially adjacent to the free ends of the legs 1642. In another example, detents 1644 engage against the inner surface 1624 of the outer ring 1622 during insertion of the legs 1642 into the outer ring 1622. The legs 1642 correspondingly deform and snap into their original orientations once the detents 1644 exit the outer ring 1622. The detents 1644 securely couple the seat 1640 to the outer ring 1622. In another example, the detents 1644 cooperate with an upper surface 1646 of the seat 1640 to securely couple and retain the rocker 1628 and the seat 1640 within the outer ring 1622. In yet another example, the detents 1644 securely couple the seat 1640 to the outer ring and allow translational movement of the seat 1640 within the outer ring 1622.

The legs 1642 of the seat 1640 cooperate with the grooves 1630 of the rocker 1628 and the grooves 1626 of the outer ring 1622 to form the guide tube lumens 1608 (FIG. 16A). In one example, the projection 1632 of the rocker 1628 cooperates with the inner surface 1624 of the outer ring 1622 to define the central guide tube lumen 1608. In another example, the guide tube lumens 1608 are aligned with the pattern 1648 extending through the upper surface 1646.

When assembled, the guide tube stop 1620 operates to pass at least one guide tube 1602 through one of the guide tube lumens 1608. In one example, the guide tube lumens 1608 are sized and shaped so the guide tube 1602 is slidably coupled with the guide tube stop 1620. In another example, the guide tube lumens 1608 of the guide tube stop 1620 are aligned with the instrument lumens 1416 in the instrument guides 1400, 1500 (FIGS. 14 and 15) using corresponding keys and recesses included on the first stage 210 and the guide tube stop 1620. In yet another example, the thumbscrew 1638 is turned to clamp the guide tube stop around the guide tube 1602 and substantially immobilize the guide tube 1602 (described below). Immobilizing the guide tube 1602 substantially prevents undesirable movement of the guide tube 1602 such as during exchange of instruments when the instruments are drawn through the guide tube 1602.

In one example, the cooperative relationship of the rocker 1628 with the outer ring 1622 and the seat 1640 facilitates clamping of the guide tube 1602 in any of the guide tube lumens 1608. In one example, a guide tube 1602 is inserted through the pattern 1648 into the guide tube lumens 1608. The thumb screw 1638 is operated to engage the stud 1634 and move the rocker 1628 toward the grooves 1626 of the outer ring 1622. Where the guide tube 1602 is disposed within one of the guide tube lumens 1608 between the rocker 1628 and the seat 1640, the rocker 1628 moves until the opposing surfaces defining the grooves 1630 and the legs 1642 engage against and securely clamp around the guide tube 1602. In another example, the guide tube 1602 is disposed between the projection 1632 and the inner surface 1624 substantially adjacent to the grooves 1626. The rocker 1628 moves toward the inner surface 1624 and clamps the guide tube 1602 between the projection 1632 and the inner surface 1624. In one example, the rocker 1628 pivots around the stud 1634 to engage and clamp the guide tube 1602. In yet another example, the guide tube 1602 is disposed between the legs 1642 and the grooves 1626. The rocker 1628 moves and engages against the seat 1640. The seat 1640 moves with the rocker 1628 toward the grooves 1626. The guide tube 1602 is clamped between the legs 1642 and the inner surface 1624 defining the grooves 1626. The guide tube stop 1620 is thereby operable to clamp and immobilize the guide tube 1602, including multiple guide tubes 1602, in any of the guide tube lumens 1608.

FIG. 17 is a perspective view of the normalizing stage 100 arranged for advancing a first instrument 1700, for example a recording electrode. In this example, the guide tube stop 1600 is coupled to the first stage 210, as described above. The guide tube 1602 extends through the guide tube stop 1600 and the first stage 210. The guide tube flange 1610 prevents the guide tube 1602 from sliding completely through the guide tube stop 1600. A spacer tube 1702 is positioned within the guide tube 1602 and is dimensioned and configured to slidably couple with the inner surface of the guide tube 1602. The spacer tube 1702 includes a spacer tube flange 1704 extending partially or completely about its proximal circumference. The flange 1704 engages the upper surface of the guide tube 1602 when the spacer tube 1702 is within the guide tube 1602 and prevents the spacer tube from sliding through the guide tube 1602.

The first instrument 1700 is fed through the spacer tube 1702 toward the target. The spacer tube 1702 constrains lateral movement of the first instrument 1700. Therefore, the first instrument moves along the trajectory 228 defined by the socket 202 (or parallel to the trajectory 228 when using an offset lumen 1608) because the guide tube 1602 and spacer tube 1702 are aligned with that trajectory 228. A portion of the first instrument 1700 is immobilized within a retaining assembly 1706 that is coupled to the second stage 218 within the retaining assembly orifice 226. The thumbscrew 232 tightens the retaining assembly around the first instrument 1700. The retaining assembly 1706 immobilizes the portion of the first instrument 1700 with respect to the second stage 218. As a result, translation of the second stage 218 correspondingly translates the first instrument 1700 within the spacer tube 1702 and guide tube 1602.

FIG. 18 is a front view of a bracket assembly 1800 including a bracket 1802, a measurement tube 1804, and a second instrument 1806, for example a stimulation electrode. In this example, the bracket has a distal collar base 1808 dimensioned and configured to snugly couple with the second stage 218 within the retaining assembly orifice 226. A measurement tube lumen extends through the collar base 1808 at the distal end of the bracket 1802. The measurement tube lumen is dimensioned and configured to couple with a measurement tube 1812. The measurement tube 1812 extends from a proximal end 1814 to a distal end 1816. The proximal end 1814 is coupled to the bracket 1802 at the bracket proximal end against retaining prongs 1818. In this example, four prongs 1818 extend from each side of the bracket 1802. The inner surfaces of the prongs couple with the proximal end 1814 of the measurement tube 1812. In another example, additional or fewer prongs 1818 are included with the bracket 1802. In yet another example, each side of the bracket 1802 is dimensioned and configured to couple with the measurement tube 1812. In this example, the proximal end of the bracket 1802 immobilizes a portion of the second instrument 1806 with a thumbscrew 1820 or the like that extends through one side of the bracket into a furrow 1822 carrying the second instrument. The thumbscrew 1820 is rotated until one end engages the second instrument 1806 and immobilizes the instrument 1806 against the opposing side of the bracket 1802.

The measurement tube 1812 is used to calibrate the operating length of the second instrument 1806. The second instrument 1806 is positioned within the measurement tube 1812 and immobilized by the thumbscrew 1820 so a distal end of the second instrument is substantially coterminous with the distal end 1816 of the measurement tube. The calibration of the second instrument 1806 length with respect to the measurement tube 1812 allows the distal end of the second instrument to plunge to the target area determined with the first instrument (described below). Additionally, the bracket 1802 provides additional instrument length for the guide tube 1602 to advance along, as described below. The measurement tube 1812 eliminates the need for measuring out the second instrument 1806 thereby simplifying the determination of the second instrument 1806 length.

Operation of the Normalizing Stage Assembly with Centered Alignment Guides and Centered Instrument Guides In one example of operation, a burr hole is cut into the skull of the patient. As shown in FIG. 11, the instrument immobilizer 1100 is coupled to the skull around the burr hole. In an example, the instrument immobilizer 1100 is coupled to the skull with bone screws. Then, the saddle assembly 1104 is coupled to the instrument immobilizer 1100, such as by screws extending through the base ring 1108. The alignment ring 1136 is disposed around the cylindrical wall defining the guide lumen 1120. The alignment ring 1136 engages the inward turned lip of the saddle slide 1112, as described above. As shown in FIG. 12, the centered alignment guide 1200 is disposed within the guide lumen 1120. The centered alignment guide keyed teeth 1208 engage the corresponding grooves 1132 of the alignment ring 1136. The engagement of the keyed teeth 1208 to the grooves 1132 and the engagement of the alignment ring 1136 to the rack 1140 of the saddle slide 1112 prevents unwanted rotation between the centered alignment guide 1200 and the saddle assembly 1104.

The orienting fixture 1202, illustrated in FIG. 12, is coupled to the alignment pin 1206. In this example, the alignment guide thumbscrew 1212 immobilizes the orienting fixture 1202 between the thumbscrew and the alignment pin 1206. The saddle assembly 1104 is then adjusted rotationally, arcuately, or both to define a trajectory to a desired target of the brain. The orientation fixture 1202 is used to display the trajectory on an IGS workstation during the adjustment. Once the desired trajectory is obtained thumbscrews 1114 are tightened on the saddle assembly 1104 to prevent further rotational and arcuate motion of the saddle assembly 1104. The alignment guide 1200 and alignment ring 1136 are rotated around guide lumen 1120. In one example, the tabs 1138 and teeth 1142 of the rack 1140 cooperatively engage for rotation of the alignment guide 1200 and the alignment ring 1136 at clicking increments (e.g. 4 degree increments). A marking 1216 is revealed through the alignment window 1214. The alignment guide 1200 and alignment ring 1136 are rotated so the marking 1216 and thereby the alignment guide 1200 coupled to the alignment ring 1136 are in a desired orientation (e.g., an anterior-to-posterior orientation of a skull). As a result, the pattern of instrument lumens 1416 (See FIG. 14) will be in the same desired orientation when the instrument guide 1400 is coupled to the alignment ring 1136 (described below).

Alignment of the alignment guide 1200 and the alignment ring 1136 to the desired orientation is done visually in one example. In another example, an IGS workstation is used to measure rotation of the alignment guide 1200 and the alignment ring 1136 and to determine when the desired orientation is achieved. The orienting fixture 1202 is keyed to the alignment guide 1200 in this example, to align the orienting fixture 1202 with respect to the alignment guide 1200.

The relative location of the orienting fixture 1202 is also used by the IGS workstation to determine the proper location of the first stage 210 with respect to the desired target area, and proper lengths of instruments 1700, 1806, and the guide tube 1602, obturator 1604 and spacer tube 1702. In one example, the IGS workstation determines the initial position of the first stage 210 with respect to the target area. The first stage 210 is moved with respect to the base 200 and the position of the first stage 210 relative to the target area is determined with, for instance, the scale 304 and reference mark 306 (described below)

FIG. 19 is a perspective view illustrating the fixture assembly 102, normalizing stage assembly 100, and a first instrument 1700. The orienting fixture 1202 and the centered alignment guide 1200 have been removed from the saddle assembly 1104. The centered instrument guide 1400 is then coupled to the saddle assembly 1104 in a similar manner to the centered alignment guide 1200. The centered instrument guide 1400 is coupled to the alignment ring 1136 so the same marking 1216 used to position the alignment guide 1200 and the alignment ring 1136 is revealed in the alignment window 1420. The centered instrument guide 1400 is thereby positioned in the desired orientation determined with the alignment guide 1200 and the orientation fixture 1202 (described above). Revealing the same marking 1216 ensures proper positioning of the instrument guide 1400 and the corresponding instrument lumens 1416 to the desired orientation.

The first stage actuator 300 (FIG. 3) is turned to initially adjust the first stage 210 to substantially coincide with the desired distance as determined with the orienting fixture 1202. The scale 304 and reference mark 306 are used to measure the position of the first stage 210 with respect to the desired target area. If necessary, the second stage 218 is adjusted with the actuator knob 308 to a desired starting position. In one example, the starting position for the second stage 218 is read from the scales 316A-C, attached to the first stage 210, and a reference marking 314, attached to a protrusion 310 extending from the second stage 218. In another example, the position of the second stage 218 is determined with the potentiometer assembly 600.

In one example, the stages 210, 218 are adjusted before coupling the normalizing stage apparatus 100 to the centered instrument guide 1400. In another example, the adjustments are made after coupling the normalizing stage 100 to the centered instrument guide 1400. Keyed teeth 1418 on the centered instrument guide 1400 engage with corresponding slots 500 within the socket 202 of the base 200. The keyed teeth 1418 and slots 500 prevent relative rotation between the centered instrument guide 1400 and the normalizing stage assembly 100. Thumbscrew 204 is tightened to securely couple the normalizing stage 100 to the centered instrument guide 1400.

In FIG. 16A, the guide tube 1602 and obturator 1604 are coupled to each other, so the obturator is disposed within the guide tube 1602 and the obturator flange 1616 engages the upper surface of the guide tube. The guide tube distal end 1612 and obturator distal end 1614 define a blunt surface. Both the guide tube 1602 and obturator 1604 are of a standard length that is factored into the function used to determine the position of the first stage 210 with the orienting fixture 1202 (FIG. 12). The guide tube 1602 and obturator 1604 are plunged through a guide tube lumen 1608 within the guide tube stop 1600. The guide tube flange 1610 engages the guide tube stop 1600 to prevent unwanted advancement of the guide tube 1602 beyond the guide tube stop 1600. The guide tube 1602 and obturator 1604 also extend through the centered instrument guide 1400, specifically, one of the instrument guide lumens 1416. In this example, because the first stage 210 is adjusted to substantially coincide with the distance measurement described above, the distal ends of the standard length guide tube 1602 and obturator 1604, are substantially adjacent to the desired target when plunged. In one example, these distal ends are offset a desired approach distance from the target, for example, 15 millimeters. In another example, the physician offsets the distal ends a desired approach distance.

After plunging of the guide tube 1602 and obturator 1604, the obturator 1604 is removed from the guide tube 1602, such as by grasping the obturator flange 1616 by hand or with a tool such as a forceps to lift the obturator 1604 out of the guide tube 1602.

After removal of the obturator 1604, the spacer tube 1702 (FIG. 17) is then inserted into the guide tube 1602 until the spacer tube flange 1704 engages the upper surface of the guide tube 1602. The spacer tube 1702 has a length substantially similar to that of the guide tube 1602. As a result, the distal end of the spacer tube 1702 is substantially adjacent to the distal end of the guide tube 1602.

As shown in FIG. 17, the retaining assembly 1706 is then inserted into the retaining assembly lumen 226 of the second stage 218. The first instrument 1700 is fed through the retaining assembly 1706 and into spacer tube 1702. In this example, the thumbscrew 232 is rotated to tighten the retaining assembly 1706 around the first instrument 1700. The first instrument 1700 is of a standard predetermined length, for such an off the shelf instrument 1700. In one example, the first instrument 1700 is a recording electrode with a flange 1708 at its proximal end to engage an upper surface of the retaining assembly 1706. The distance between a distal end of the instrument and the flange is a standard predetermined length. The first stage 210 and second stage 218 are initially positioned to take into account the distance to the desired target and the predetermined lengths of the instruments and tubes (described above). As a result, the distal end of the standard length first instrument 1700, when plunged with the flange 1708 engaged to the retaining assembly 1706, is substantially adjacent to the distal end of the guide tube 1602 and the distal end of the spacer tube 1702. The distal end of the first instrument 1700 and the distal end of the guide tube 1602 are substantially adjacent to the desired target or are offset from the desired target area some distance, for example, 15 millimeters, as described above.

In this example, a physician or technician then operates actuator knob 308 to move the second stage 218 and first instrument 1700 coupled thereto along the screw 220. The distal end of the first instrument 1700 is moved toward, away or through the desired target, as desired. In one example, the relative position of the distal end of the first instrument 1700 with respect to the desired target area is read from the scale 316A with reference marking 314. In another example, the relative position of the first instrument 1700 is read from the reference marking 402 against the fine scale 400 (FIG. 4) coupled to the screw 220. In still another example, the relative position of the first instrument 1700 is measured with a potentiometer assembly 600, as described above. In another embodiment the hydraulic system 700 is used to move the second stage 218 through actuation of the master piston 708 with respect to the master cylinder 706.

If the physician is satisfied with the track of the first instrument 1700 to the desired target, a second instrument 1806 is substituted (described below). If the physician is not satisfied with the track of the first instrument 1700 (for example, a blood vessel blocks advancement of the first instrument 1700) it is retracted away from the target. The retaining assembly 1706 is loosened through thumbscrew 232, and the first instrument 1700 is removed from the normalizing stage assembly 100. The retaining assembly 1706 is then removed from the second stage 218. The guide tube 1602 and spacer tube 1702 are then removed from the guide tube stop 1600. The physician may then plunge another guide tube 1602 and obturator 1604 in an adjacent guide tube lumen 1608. The process described above is then substantially repeated for the new track created by the guide tube 1602 in the adjacent lumen 1608.

Operation of the Normalizing Stage Assembly with Offset Alignment Guides and Offset Instrument Guides Alternatively, the physician removes the entire normalizing stage assembly 100, and the centered instrument guide 1400. An offset alignment guide 1300 (FIG. 13) is coupled to the saddle assembly 1104. In another example, the physician uses the offset alignment guide 1300 from the beginning instead of the centered alignment guide 1200, if so desired. The keyed teeth 1214 of the offset alignment guide 1300 and the corresponding grooves 1132 on the alignment ring 1136 make the offset guide 1300 positionable at 45 degree increments (FIG. 11). Additionally, the offset alignment guide 1300 is positionable at 4 degree increments through actuation of alignment ring 1136 around the rack 1140. The orienting fixture 1202, illustrated in FIG. 12, is coupled to the alignment pin 1306. In this example, the alignment guide thumbscrew 1212 immobilizes the orienting fixture 1202 between the thumbscrew and the alignment pin 1306.

The saddle assembly 1104 is then adjusted rotationally and/or arcuately, to define a trajectory to a desired target of the brain. Once the physician is initially satisfied with the trajectory of the saddle assembly 1104 and offset alignment guide 1300 coupled thereto, thumbscrews 1114 are tightened on the saddle assembly 1104 to prevent further rotational and arcuate motion of the saddle 1104. The location of the orienting fixture 1202 with respect to the desired target is detected through the imaging methods described above. The relative location of the orienting fixture 1202 is used to determine the desired location of the first stage 210 with respect to the target. An IGS work station, for example, takes into account the lengths of standardized "off the shelf" instruments 1700, 1806, and the guide tube 1602, obturator 1604 and spacer tube 1702.

The alignment guide 1300 and alignment ring 1136 are rotated around guide lumen 1120 as described above with the alignment guide 1200. A marking 1216 is revealed through the alignment window 1214. The alignment guide 1300 and alignment ring 1136 are rotated so the marking 1216 and thereby the alignment guide 1300 coupled to the alignment ring 1136 are in a desired orientation (e.g., an anterior-to-posterior orientation of a skull). As a result, the pattern of instrument lumens 1416 (See FIG. 15) will be in the same desired orientation when the instrument guide 1500 is coupled to the alignment ring 1136 (described below). Aligning of the alignment guide 1300 and the alignment ring 1136 to the desired orientation is done, for instance, visually or with an IGS workstation as described above for alignment guide 1200.

The orienting fixture 1202 and the offset alignment guide 1300 are removed from the saddle assembly 1104. The offset instrument guide 1500 is coupled to the saddle assembly 1104 in the same orientation as was the offset alignment guide 1300. In one example, the offset instrument guide 1500 is coupled to the alignment ring 1136 so the same marking 1216 used to position the alignment guide 1300 and the alignment ring 1136 is revealed in the alignment window 1420. The offset instrument guide 1500 is thereby positioned in the desired orientation determined with the alignment guide 1300 and the orientation fixture 1202 (described above). Revealing the same marking 1216 ensures proper positioning of the instrument guide 1500 and the corresponding instrument lumens 1416 to the desired orientation.

The first stage actuator 300 is turned to initially adjust the first stage 210 to substantially coincide with the distance determined with the orienting fixture 1202. The scale 304 and reference mark 306 are used to measure the position of the first stage 210 with respect to the desired target. If necessary, the second stage 218 is adjusted with the actuator knob 308 to a desired starting position. In one example, the starting position for the second stage 218 is read from one of the scales 316A-C, attached to the first stage 210, and a reference marking 314, attached to a protrusion 310 extending from the second stage 218. In another example, the position of the second stage 218 is determined with the potentiometer assembly 600 (FIG. 6) coupled between the second stage 218 and the first stage 210.

The normalizing stage apparatus 100 is coupled to the offset instrument guide 1500 (See FIG. 15). In this example, the adjustments to the stages 210, 218 are performed before coupling the normalizing stage apparatus 100 to the offset instrument guide 1500. In another example, the adjustments are made after coupling the normalizing stage 100 to the offset guide 1500. Keyed teeth 1510 on the offset guide 1500 engage with corresponding slots 500 within the socket 202 of the base 200. This prevents relative rotation between the offset instrument guide 1500 and the normalizing stage assembly 100. Thumbscrew 204 is tightened to securely couple the normalizing stage 100 to the offset instrument guide 1500.

The obturator 1604 is inserted into the guide tube 1602 until the obturator flange 1616 engages the upper surface of the guide tube 1602. The guide tube distal end and obturator distal end define a blunt surface. Both the guide tube 1602 and obturator 1604 are of a standard length that is factored into the function used to determine the position of the first stage 210 with the orienting fixture 1202. The guide tube 1602 and obturator 1604 are plunged together through a guide tube lumen 1608 within the guide tube stop 1600 until the guide tube flange 1610 engages the guide tube stop 1600. The guide tube 1602 and obturator 1604 also extend through the offset instrument guide 1500, specifically, one of the instrument guide lumens 1416. In this example, because the first stage 210 is adjusted to substantially coincide with the distance measurement described above, the distal ends of the standard length guide tube 1602 and obturator 1604, are substantially adjacent to the desired target area when plunged. In one example, the distal ends are offset from the target a desired approach distance, for example, 15 millimeters. In another example, the physician offsets the distal ends a desired approach distance from the target.

After plunging of the guide tube 1602 and obturator 1604, the obturator 1604 is removed from the guide tube 1602. The spacer tube 1702 is inserted into the plunged guide tube 1602 until the spacer tube flange 1704 engages the upper surface of the guide tube 1602. The spacer tube 1702 has a length substantially similar to that of the guide tube 1602 so the distal end of the spacer tube 1702, when inserted, is substantially adjacent to the distal end 1612 of the guide tube 1602.

FIG. 19 is a perspective view of the normalizing stage apparatus 100 showing the relation of the first instrument 1700 to the normalizing stage apparatus 100. Operation of the normalizing stage apparatus 100 with the illustrated centered instrument guide 1400 is substantially similar to operation with the offset instrument guide 1500. The retaining assembly 1706 is coupled to the second stage 218 and within retaining assembly orifice 226 after removal of the obturator 1604. The first instrument 1700 is then fed through the retaining assembly 1706 in the second stage 218 and into spacer tube 1702. In this example, the thumbscrew 232 is rotated to tighten the retaining assembly 1706 around the first instrument 1700. The first instrument 1700 is of a standard length. In one example, the first instrument 1700 is a recording electrode. In this example, the recording electrode has a distal end, and a flange 1708 disposed at its proximal end to engage an upper surface of the retaining assembly 1706. The distance between the distal end of the instrument 1700 and the flange 1708 is a standard length. The first stage 210 and second stage 218 are initially positioned with respect to the desired target. The positioning of the first stage 210 and second stage 218 takes into account the lengths of the standardized (off the shelf) instruments and tubes (described above). As a result, the distal end of the standard length first instrument 1700, when plunged with the flange 1708 engaged to the retaining assembly 1706, is substantially adjacent to the distal end 1612 of the guide tube 1602 and the distal end of the spacer tube 1702. In one example, the distal end of the first instrument 1700 and the distal end of the guide tube 1602 are substantially adjacent to the desired target. In another example, the distal end 1612 and distal end of the first instrument 1700 are offset from the desired target some distance, for example, 15 millimeters, as described above.

In this example, a physician or technician then turns actuator knob 308 to move the second stage 218, and first instrument 1700 coupled thereto, along the screw 220. The distal end of the first instrument 1700 is moved toward, away or through the desired target area as desired. In one example, the relative position of the distal end of the first instrument 1700 with respect to the desired target is read from the scale 316A with reference marking 314. In another example, the relative position of the first instrument 1700 distal end is read on the scale 316 with respect to the distal end of the guide tube 1602. In yet another example, the relative position of the first instrument 1700 is read from the reference marking 402 against the fine scale 400 (FIG. 4) coupled to the screw 220. In still another example, the relative position of the first instrument 1700 is measured with a potentiometer assembly 600, as described above. In another embodiment the hydraulic system 700 is used to move the second stage 218 through actuation of the master piston 708 with respect to the master cylinder 706.

If the physician is satisfied with the track of the first instrument 1700 to the desired target, a second instrument 1806 is substituted (described below). If the physician is not satisfied with the track of the first instrument 1700 (for example, a blood vessel blocks advancement of the first instrument 1700) it is retracted away from the target. The retaining assembly 1706 is loosened through thumbscrew 232, and the first instrument is removed from the normalizing stage assembly 100. The retaining assembly 1706 is then removed from the second stage 218. The guide tube 1602 and spacer tube 1702 are then removed from the guide tube stop 1600. The physician may then plunge another guide tube 1602 and obturator 1604 in an adjacent guide tube lumen 1608. The process described above is then substantially repeated for the new track created by the guide tube 1602 in the adjacent lumen 1608. In another example, the physician adjusts the position of the offset instrument guide 1500 through actuation of the alignment ring 1136. In one example, adjustment of the guide 1500 position also requires use of the offset alignment guide 1300 to redetermine the relative position of the first stage 210 with respect to the target area and standardized instruments and tubes. In still another example, the physician removes the offset instrument guide 1500 and uses a centered alignment guide 1200 and centered instrument guide 1400 to make another track to the desired target area.

Operation of the Normalizing Stage Assembly with the Second Instrument

FIG. 20 is a perspective view showing the normalizing stage apparatus 100, bracket assembly 1800, and the second instrument 1806. Before coupling of the bracket 1802 to the normalizing stage apparatus, the bracket assembly 1800 is used to measure out the length for the second instrument 1806. The measurement tube 1804 (FIG. 18) is coupled to the bracket 1802 so the tube is disposed within the measurement tube lumen 1810 and the proximal end 1814 of the tube is coupled to the bracket by the retaining prongs 1818. The second instrument 1806 is fed into the measurement tube 1804 until the distal end of the second instrument is substantially coterminous with the distal end 1816 of the measurement tube (FIG. 18). A portion of the second instrument 1806 is immobilized by thumbscrew 1820 that engages the second instrument 1806 against the opposing side of the bracket 1802. The measurement tube is then uncoupled from the bracket 1802. The retaining assembly 1706 is uncoupled from the second stage 218, and the spacer tube 1702 is removed from engagement with the guide tube 1602 in a similar manner as the obturator 1604. The bracket 1802 is coupled to the second stage within the retaining assembly orifice 226. In this example, the retaining assembly orifice 226 includes a slot and the bracket collar base 1808 includes a key dimensioned and configured to cooperatively engage the surface defining the slot. The thumbscrew 232 is tightened to securely couple the bracket 1802 to the second stage. The slot and key relationship determines the orientation of the bracket 1802 relative to the second stage 218. The second instrument 1806 is then fed, distal end first, through the guide tube 1602 and plunged toward the target along the track determined with the first instrument 1700.

The bracket 1802 provides a constant offset distance between the second stage 218 and the bracket proximal end where the second instrument 1806 is coupled. This constant offset distance is reflected in the additional length of the second instrument 1806 over the first instrument 1700. The constant offset allows the distal end of the second instrument 1806 to plunge to the location determined with the first instrument 1700. In other words, when plunging the second instrument 1806, the normalizing stage apparatus 100, specifically first stage 210 and second stage 218, are in the positions determined with the first instrument 1700. The second instrument 1806 thus plunges so the distal end of the instrument is substantially adjacent to the prior location of the first instrument 1700 distal end.

A perspective view of the normalizing stage apparatus 100, the second instrument 1806, the guide tube 1602, and the instrument immobilizer 1100 is shown in FIGS. 21 and 22. The second instrument 1806 is disposed within the guide tube 1602. To remove the guide tube 1602 and leave the second instrument 1806 at the desired location, the guide tube 1602 is moved out of engagement with the guide tube stop 1600. The guide tube 1602 is advanced along the second instrument 1806 which is slidably coupled thereto. As shown in FIG. 21, the guide tube 1602 is moved at least until the distal end of the guide tube is above the instrument immobilizer 1100. The retaining piece 1106 is then moved into engagement against the second instrument 1806 to immobilize the instrument between the retaining piece and the opposing surface of the instrument immobilizer 1100, as shown in FIG. 22. The second instrument 1806 is substantially immobilized between the instrument immobilizer 1100 and the distal end of the second instrument 1806. Additionally, the distal end of the second instrument 1806 is located at the desired target location along the track determined with the first instrument 1700.

The thumbscrew 1820 is loosened to release the second instrument 1806 from engagement to the bracket 1802. In this example, the thumbscrew 204 is loosened to allow uncoupling of the normalizing stage assembly 100 from the instrument guide (1600 or 1500). The saddle assembly 1104 is uncoupled from the instrument immobilizer 1100 by loosening screws extending therebetween, in one example. In another example, the saddle assembly 1104 is uncoupled from the instrument immobilizer 1100 while the normalizing stage assembly 100 is still coupled to the saddle assembly 1104. In yet another example, the second instrument 1806 is pulled through an orifice between the saddle slide 1112 and the tower base 1110 to uncouple the second instrument from the normalizing stage assembly 100. The saddle assembly 1104 and normalizing stage assembly 100 are then easily uncoupled from the instrument immobilizer 1100 and the second instrument 1806 is not otherwise disturbed. The second instrument 1806 is left engaged to the instrument immobilizer with the distal end at the desired target.

FIG. 23 is a perspective view showing the instrument immobilizer 1100, the second instrument 1806, and a cap 2300. The portion of the second instrument 1806 outside of the skull and beyond the instrument immobilizer 1100 is bent over, and the cap 2300 is engaged to the instrument immobilizer. In this example, the cap is elastic and deforms to snugly engage with the instrument immobilizer 1100 and retain the second instrument 1806 in its orientation.

Techniques for Using a Normalizing Stage Apparatus

FIG. 24 is a block diagram illustrating generally, by way of example, but not by way of limitation, examples of certain techniques for using a normalizing stage, such as the normalizing stage apparatus 100 of FIG. 1. The normalizing stage, in this example, includes a base, a first stage moveably coupled to the base and operable to move with respect to the base, and a second stage moveably coupled to the first stage and operable to move with respect to the first stage and the base. The techniques disclosed herein need not be carried out in the exact order illustrated in the block diagrams of FIGS. 24-29. At 2402, a fixing assembly is coupled to the body. In this example, the fixing assembly is coupled to the skull. At 2404, the relative position of the normalizing stage with respect to a desired target, the instruments, and other equipment (described above) is determined. A first instrument is plunged and advanced to the target at 2406. In this example, the first instrument is a recording electrode. At 2408, a second instrument is plunged to the target area. In this example, the second instrument is a stimulation electrode. At 2410, the second instrument is immobilized and the normalizing stage and fixing assembly are removed.

FIG. 25 is a more detailed block diagram illustrating techniques for coupling the fixing assembly to the skull 2402. At 2500, an instrument immobilizer is coupled to the skull. In this example, the instrument immobilizer is coupled around a burr hole in the skull. A saddle is coupled to the instrument immobilizer at 2502. In this example, the saddle is aligned with a trajectory defined by the instrument immobilizer. At 2504, an alignment ring, such as the alignment ring 1136 in FIG. 11, is coupled to the saddle.

FIG. 26 is a more detailed block diagram illustrating techniques for determining the relative position of the normalizing stage with respect to the desired target area, the instruments, and other equipment 2404. At 2600, an alignment guide is coupled to the saddle and engaged to the alignment ring. In one example, the alignment guide is an embodiment such as centered alignment guide 1200. The alignment guide includes an alignment pin aligned with the longitudinal axis of the alignment guide. In another example, the alignment guide includes an alignment pin parallel to, and offset from, the longitudinal axis of the alignment guide. At 2602, an orienting fixture, such as orienting fixture 1202, is coupled to the alignment guide. In one example, the orienting fixture is coupled to the alignment pin of the alignment guide. At 2604, the saddle and the alignment ring are adjusted to determine a trajectory and orientation to the desired target. In this example, the saddle is adjusted rotationally and/or arcuately. The location of a first stage of the normalizing stage is determined with respect to the desired target, standardized (off the shelf) instruments, and tubes used to plunge the instruments, at 2606. In this example, the location of the first stage is determined with imaging of the orienting fixture. At 2608, the orienting fixture and alignment guide are uncoupled and removed.

FIG. 27 is a more detailed block diagram illustrating techniques for plunging the first instrument and advancing it toward the target area 2406. At 2700, the first stage is positioned to the desired starting position determined in 2404 (described above). At 2702, the second stage is positioned to a desired starting position. In one example, the second stage is not adjusted because it is already calibrated to a starting position and is moveably coupled to the first stage. In this example, the second stage moves correspondingly with the first stage as the first stage is moved. At 2704, an instrument guide is coupled to the saddle and engages with the alignment ring. In one example, the instrument guide has at least one instrument guide lumen aligned with the longitudinal axis of the instrument guide, as described with centered instrument guide 1400 above. In another example, the instrument guide includes at least one instrument guide lumen parallel to, and offset from, the longitudinal axis of the instrument guide. In yet another example, the offset instrument guide lumen has substantially the same alignment as the alignment pin of the offset alignment guide (described above). At 2706, the normalizing stage is coupled to the instrument guide. In this example, the normalizing stage has a base that defines a trajectory, and the trajectory is parallel to the longitudinal axis of the instrument guide. In another example, the trajectory of the normalizing base is aligned with the longitudinal axis of the instrument guide. At 2708, a standard length (usable off the shelf) guide tube and standard length (also usable off the shelf) obturator are plunged together through a guide tube stop coupled to the first stage of the normalizing stage until engaged to the guide tube stop. In this example, the obturator is coupled with the guide tube so the distal ends of the guide tube and obturator define a blunt surface. The obturator is removed from engagement with the guide tube at 2710. At 2712, a standard length off the shelf spacer tube is plunged through the guide tube stop, specifically the guide tube, until engaged with the guide tube. In this example, the guide tube, obturator, and spacer tube include flanges that engage surfaces, for example the guide tube stop, and prevent further plunging of the guide tube, obturator and/or spacer tube. At 2714, the first instrument is plunged through a retaining assembly coupled to the second stage and the spacer tube toward the target. Because of the positioning of the first stage 2700 (and second stage 2702 if necessary), the first instrument distal end is coterminous with the distal end of the guide tube when plunged. At 2716, the first instrument is moved toward, away and/or through the desired target. In this example, the first instrument is moved outside of the guide tube and toward the target area.

FIG. 28 is a more detailed block diagram illustrating techniques for plunging the second instrument 2408. At 2800, the first instrument is uncoupled and removed from the second stage retaining assembly and the spacer tube. At 2802, the spacer tube is removed from engagement with the guide tube. In this example, the spacer tube is removed from the guide tube. At 2804, a length of the second electrode is measured with a bracket (for example, bracket 1802) and measurement tube (e.g. measurement tube 1804) coupled to the bracket. In this example, the second instrument is fed through the measurement tube and the portion of the bracket coupled to the measurement tube. The second instrument is coupled to the bracket and the measurement tube is uncoupled from the bracket at 2806. At 2808, the bracket is coupled to the second stage of the normalizing stage. In this example, the retaining assembly is uncoupled from the second stage and the bracket coupled in its place. At 2810, the second instrument is plunged through the guide tube toward the target along the track determined with the first instrument.

FIG. 29 is a more detailed block diagram illustrating techniques for immobilizing the second instrument and removing the stage and fixing assembly 2410. At 2900, the guide tube is moved out of engagement with the guide tube stop. In this example, the guide tube is advanced upward relative to the second stage along the second instrument. At 2902, the instrument immobilizer (for example, instrument immobilizer 1100) is actuated to immobilize a portion of the second instrument from the instrument immobilizer to the distal end of the second instrument at the target. In one example, the instrument immobilizer includes a retaining piece 1106 (FIG. 11) that is actuated to engage the second instrument and immobilize it against the instrument immobilizer. At 2904, the second instrument is uncoupled from the bracket. In one example, the bracket is uncoupled and removed from the second stage. The normalizing stage is removed from the instrument guide at 2906. At 2908, the saddle is uncoupled and removed from the instrument immobilizer. In another example, the normalizing stage is left coupled to the instrument guide and the saddle, and the saddle, instrument guide, and normalizing stage are uncoupled as a single unit from the instrument immobilizer. At 2910, the non-immobilized portion of the second instrument is bent over and a cap is engaged to the instrument immobilizer to further retain the second instrument.

CONCLUSION

The various embodiments of the normalizing stage in this document are presented as illustrative examples, and are not intended to be limiting. The normalizing stage embodiments discussed in this document will be capable of use with a variety of fixture assemblies, including the fixture assemblies discussed above. Additionally, the normalizing stage and the techniques discussed herein are not limited to advancing instruments toward, away or through target locations within a subject's brain. The normalizing stage apparatus and techniques are also applicable to targeting other locations within a subject. Furthermore, the normalizing stage and techniques discussed in this document may also be useful for moving instruments toward, away or through desired target locations within any material.

The normalizing stage described in this document provides a standard distance to a desired target. The standard distance provided with the first stage allows use of standard length, off the shelf, instruments, guide tubes, spacer tubes and obturators. The second stage moves correspondingly with the first stage. Therefore, positioning of the first stage a standard distance from the desired target likewise positions the second stage with respect to the desired target area. Once the first stage is positioned the standard distance from the target, the second stage, moveably coupled to the first stage, moves the standard instrument toward, away and through the target location as desired. In other words, the first stage allows use of off the shelf instruments, tubes and the like, while the second stage moves the off the shelf instruments toward and/or away from the target. Thus the normalizing stage expedites the introduction of instruments to the target location. Additionally, the normalizing stage and the methods for using the same eliminate time-consuming calculations for physicians and/or technicians, for instance, calculations of the instrument, tube and obturator lengths. Moreover, the normalizing stage reduces errors by simplifying the introduction of instruments with standard length instruments, tubes and the like. Error is reduced by removing calculations of instrument lengths and the like from the procedure of use.

Moreover, the normalizing stage is a cost effective disposable unit that can be used for a procedure and disposed afterwards. The normalizing stage and other equipment described in this document are packaged sterile and used at the point of use. Sterile saline is readily available at most hospitals and clinics and is used prior to the procedure to fill the hydraulic examples described above.

It is to be understood that the above description is intended to be illustrative, and not restrictive. For example, the above described embodiments may be used in combination with each other. Many other embodiments will be apparent to those of skill in the art upon reading and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on the objects.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An apparatus for advancing an instrument into a body comprising:
   a base, wherein the base defines a trajectory;
   a first stage moveably coupled to the base, wherein the first stage is moveable along the trajectory;
   a second stage moveably coupled to the first stage along a guide rail extending between the first and second stages, wherein the second stage is moveable relative to the first stage on or parallel to the trajectory and operable to move an instrument coupled thereto with respect to the base and the first stage;
   a plurality of rollers having corresponding axles positioned at different angles to one another around the guide rail; and
   a hydraulic system including:
      a hydraulic cylinder coupled to the first stage;
      a hydraulic piston coupled to the second stage; and
      a hydraulic actuator in fluid communication with the hydraulic cylinder and hydraulic piston, wherein the hydraulic actuator is operable to advance the hydraulic piston with respect to the hydraulic cylinder and move the second stage relative to the first stage.

2. The apparatus of claim 1, wherein the hydraulic actuator includes a master cylinder coupled to a master piston, and the master piston is actuated by a screw coupled between the master piston and master cylinder.

3. The apparatus of claim 1, further comprising a fluid inlet operable to receive hydraulic fluid, wherein the fluid inlet includes a check valve.

4. The apparatus of claim 1, further comprising a liquid impermeable vent coupled to the hydraulic cylinder, wherein the liquid impermeable vent is gas permeable.

5. The apparatus of claim 1, further comprising a spring having first and second ends, the first end attached to a tubular structure supported on and extending from the first stage, the second end attached to the second stage, the spring extending through the tubular structure and through the first stage, such that the spring moves the second stage and the hydraulic piston toward a fluid filled end of the cylinder, wherein the spring operates to pull or push the hydraulic piston toward one end of the hydraulic cylinder and to maintain pressurization in the hydraulic system.

6. The apparatus of claim 1, further comprising a potentiometer coupled between the first stage and the second stage, wherein the potentiometer is operable to measure the movement of the second stage relative to the first stage.

7. An apparatus for advancing an instrument into a body comprising:
   a base defining a trajectory;
   a first stage moveably coupled to the base and along the trajectory;
   a second stage moveably coupled to the first stage and operable to move an instrument with respect to the base and the first stage;
   a hydraulic cylinder and a hydraulic piston coupled relative to the first stage and the second stage, the hydraulic piston attached to the second stage and movable relative to the hydraulic cylinder by movement of the second stage;

a hydraulic actuator in fluid communication with the hydraulic cylinder and hydraulic piston, wherein the hydraulic actuator is operable to move the second stage relative to the first stage;

a tubular structure coupled to the first stage;

a spring having first and second ends, the first end attached to the tubular structure and the second end attached to the second stage, the spring extending through the tubular structure and through the first stage, such that the spring moves the second stage and the hydraulic piston toward a fluid-filled end of the cylinder to maintain pressurization in the hydraulic cylinder; and a bearing coupled between the first stage and the second stage.

8. An apparatus for advancing an instrument into a body comprising:

a first stage;

a second stage moveably coupled to the first stage, wherein the second stage is moveable relative to the first stage on or parallel to a trajectory extending through the first and second stage;

a plurality of rollers coupled to a portion of the second stage;

a guide rail extending between the first and second stages, the guide rail sized and shaped to contact the plurality of rollers at different angles to limit the motion of the second stage to linear motion around the guide rail and prevent rotation of the second stage around the guide rail, a hydraulic cylinder coupled to the first stage;

a hydraulic piston coupled to the second stage; and a hydraulic actuator in fluid communication with the hydraulic cylinder and hydraulic piston, the hydraulic actuator including a master hydraulic cylinder and a master hydraulic piston, wherein the hydraulic actuator is operable to move the second stage relative to the first stage.

9. The apparatus of claim 8, wherein the hydraulic piston is separated from the hydraulic cylinder.

10. The apparatus of claim 8, further comprising a potentiometer coupled between the first stage and the second stage, wherein the potentiometer is operable to measure the movement of the second stage relative to the first stage.

11. The apparatus of claim 8, wherein the hydraulic cylinder, hydraulic piston and the hydraulic actuator are sized and shaped for filling immediately prior to use.

12. The apparatus of claim 8, further comprising a fluid inlet in fluid communication with the hydraulic cylinder, hydraulic piston and the hydraulic actuator, wherein the fluid inlet is sized and shaped to receive hydraulic fluid.

13. The apparatus of claim 8, further comprising a gas permeable vent coupled to the hydraulic cylinder, wherein the gas permeable vent is liquid impermeable.

14. The apparatus of claim 8, further comprising a spring coupled between the first stage and the second stage, wherein the spring operates to pull or push the hydraulic piston toward one end of the hydraulic cylinder and to maintain pressurization in the hydraulic system.

15. The apparatus of claim 8, wherein the hydraulic actuator includes a liquid impermeable membrane extending between the master hydraulic cylinder and the master hydraulic piston.

16. The apparatus of claim 7, wherein the bearing is a roller coupled between the first stage and the second stage.

17. The apparatus of claim 7, wherein the bearing includes a plurality of rollers having corresponding axles positioned at different angles to one another around a guide rail extending between the first and second stages.

18. The apparatus of claim 17, wherein the hydraulic actuator includes a master hydraulic cylinder and a master hydraulic piston and a liquid impermeable membrane extending between the master hydraulic cylinder and the master hydraulic piston.

19. The apparatus of claim 17, further comprising a potentiometer coupled between the first stage and the second stage, wherein the potentiometer is operable to measure the movement of the second stage relative to the first stage.

* * * * *

UNITED STATES PATENT AND TRADEMARK OFFICE
CERTIFICATE OF CORRECTION

PATENT NO. : 7,867,242 B2  Page 1 of 1
APPLICATION NO. : 12/349657
DATED : January 11, 2011
INVENTOR(S) : Matthew Solar et al.

It is certified that error appears in the above-identified patent and that said Letters Patent is hereby corrected as shown below:

Column 32, Line 32, Claim 18
"claim 17" should be -- claim 7 --

Column 32, Line 37, Claim 19
"claim 17" should be -- claim 7 --

Signed and Sealed this
Tenth Day of May, 2011

David J. Kappos
*Director of the United States Patent and Trademark Office*